United States Patent
Costantino et al.

(10) Patent No.: US 9,493,517 B2
(45) Date of Patent: Nov. 15, 2016

(54) CONJUGATES COMPRISING AN ANTIGEN AND A CARRIER MOLECULE

(71) Applicant: Novartis AG, Basel (CH)

(72) Inventors: Paolo Costantino, Siena (IT); Maria Rosaria Romano, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 36 days.

(21) Appl. No.: 13/670,727

(22) Filed: Nov. 7, 2012

(65) Prior Publication Data

US 2013/0189300 A1    Jul. 25, 2013

Related U.S. Application Data

(60) Provisional application No. 61/556,456, filed on Nov. 7, 2011, provisional application No. 61/566,407, filed on Dec. 2, 2011.

(51) Int. Cl.

| | |
|---|---|
| *C07K 14/315* | (2006.01) |
| *A61K 39/095* | (2006.01) |
| *A61K 47/48* | (2006.01) |
| *A61K 39/00* | (2006.01) |

(52) U.S. Cl.
CPC ....... *C07K 14/3156* (2013.01); *A61K 39/0013* (2013.01); *A61K 39/095* (2013.01); *A61K 47/4833* (2013.01); *A61K 2039/6037* (2013.01)

(58) Field of Classification Search
None
See application file for complete search history.

(56) References Cited

U.S. PATENT DOCUMENTS 6,932,971 B2 *   8/2005   Bachmann et al.  ....... 424/193.1

FOREIGN PATENT DOCUMENTS

| WO | WO 02/091998 | * 11/2002 |
| WO | WO-2004/067030 |   8/2004 |
| WO | WO 2009/016515 | *  2/2009 |
| WO | WO-2009/016515 |    2/2009 |

OTHER PUBLICATIONS

Snape, M.D., et al., "Immunogencity of a Tetravalent Meningococcal Glycoconjugate Vaccine in Infants: A Randomized Controlled Trial" J. American Med. Assoc., 299(2): 173-184 (2008).

* cited by examiner

*Primary Examiner* — Oluwatosin Ogunbiyi
(74) *Attorney, Agent, or Firm* — Morrison & Foerster LLP

(57) ABSTRACT

The invention provides a conjugate comprising an antigen and a carrier molecule, wherein the carrier molecule comprises a spr0096 antigen and a spr2021 antigen. spr0096 and spr2021 are *Streptococcus pneumoniae* antigens. The conjugate may be used in a method for raising an immune response in a mammal, the method comprising administering the conjugate to the mammal. Also provided are pharmaceutical compositions, particularly vaccines, comprising the conjugate.

22 Claims, 23 Drawing Sheets

FIG. 1A

| Polysaccharide | Repeat unit |
| --- | --- |
| *Haemophilus influenzae* Type b ("PRP") | →3)-β-D-Rib*f*-(1→1)-D-Ribitol-(5→OPO₃→ |
| *Neisseria meningitidis* | |
| Group A | →6)-α-D-Man*p*NAc(3OAc)-(1→OPO₃→ |
| Group C | →9)-α-D-Neu5Ac(7/8OAc)-(2→ |
| Group W135 | →6)-α-D-Gal*p*-(1→4)-α-D-Neu5Ac(9OAc)-(2→ |
| Group Y | →6)-α-D-Glc*p*-(1→4)-α-D-Neu5Ac(9OAc)-(2→ |
| *Salmonella enterica* Typhi Vi | →)-α-D-Gal*p*NAcA(3OAc)-(1→ |
| *Streptococcus pneumoniae* | |
| Type 1 | →3)-D-AAT-α-Gal*p*-(1→4)-α-D-Gal*p*A(2/3OAc)-(1→3)-α-D-Gal*p*A-(1→ |
| Type 2 | →4)-β-D-Glc*p*-(1→3)-[α-D-Glc*p*A-(1→6)-α-D-Glc*p*-(1→2)]-α-L-Rha*p*-(1→3)-α-L-Rha*p*-(1→3)-β-L-Rha*p*-(1→ |
| Type 3 | →3)-β-D-Glc*p*A-(1→4)-β-D-Glc*p*-(1→ |
| Type 4 | →3β-D-Man*p*NAc-(1→3)-α-L-Fuc*p*NAc-(1→3)-α-D-Gal*p*NAc-(1→4)-α-D-Gal*p*2,3(S)Py-(1→ |
| Type 5 | →4)-β-D-Glc*p*-(1→4)-[α-L-Pne*p*NAc-(1→2)-β-D-Glc*p*A-(1→3)]-α-L-Fuc*p*NAc-(1→3)-β-D-Sug*p*-(1→ |

Type 6B →2)-α-D-Galp-(1→3)-α-D-Glcp-(1→3)-α-L-Rhap-(1→4)-D-Rib-ol-(5→P→
Type 9N →4)-α-D-GlcpA-(1→3)-α-D-Glcp-(1→3)-β-D-ManpNAc-(1→4)-β-D-Glcp-(1→4)-α-D-GlcpNAc-(1→

Type 14 →4)-β-D-Glcp-(1→6)-[β-D-Galp-(1→4)]-β-D-GlcpNAc-(1→3)-β-D-Galp-(1→
Type 18C →4)-β-D-Glcp-(1→4)-[α-D-Glcp(6OAc)-(1→2)][Gro-(1→P→3)]-β-D-Galp-(1→4)-α-D-Glcp-(1→3)β-L-Rhap-(1→

Type 19A →4)-β-D-ManpNAc-(1→4)-α-D-Glcp-(1→3)-α-L-Rhap-(1→P→
Type 19F →4)-β-D-ManpNAc-(1→4)-α-D-Glcp-(1→2)-α-L-Rhap-(1→P→
Type 23F →4)-β-D-Glcp-(1→4)-[α-L-Rhap-(1→2)]-[Gro-(2→P→3)]-β-D-Galp-(1→4)-β-L-Rhap-(1→

*Staphylococcus aureus*
Type 5 →4)-β-D-ManNAcA(3OAc)-(1→4)-α-L-FucNAc-(1→3)-β-D-FucNAc-(1→
Type 8 →3)-β-D-ManNAcA(4OAc)-(1→3)-α-L-FucNAc-(1→3)-β-D-FucNAc-(1→

AAT is 2-acetamido-4-amino-2,4,6-trideoxygalactose, Gro is glycerol, Pne is 2-acetamido-2,6-dideoxyxalose, and P is phosphate in a phosphodiester linkage.

*FIG. 1B*

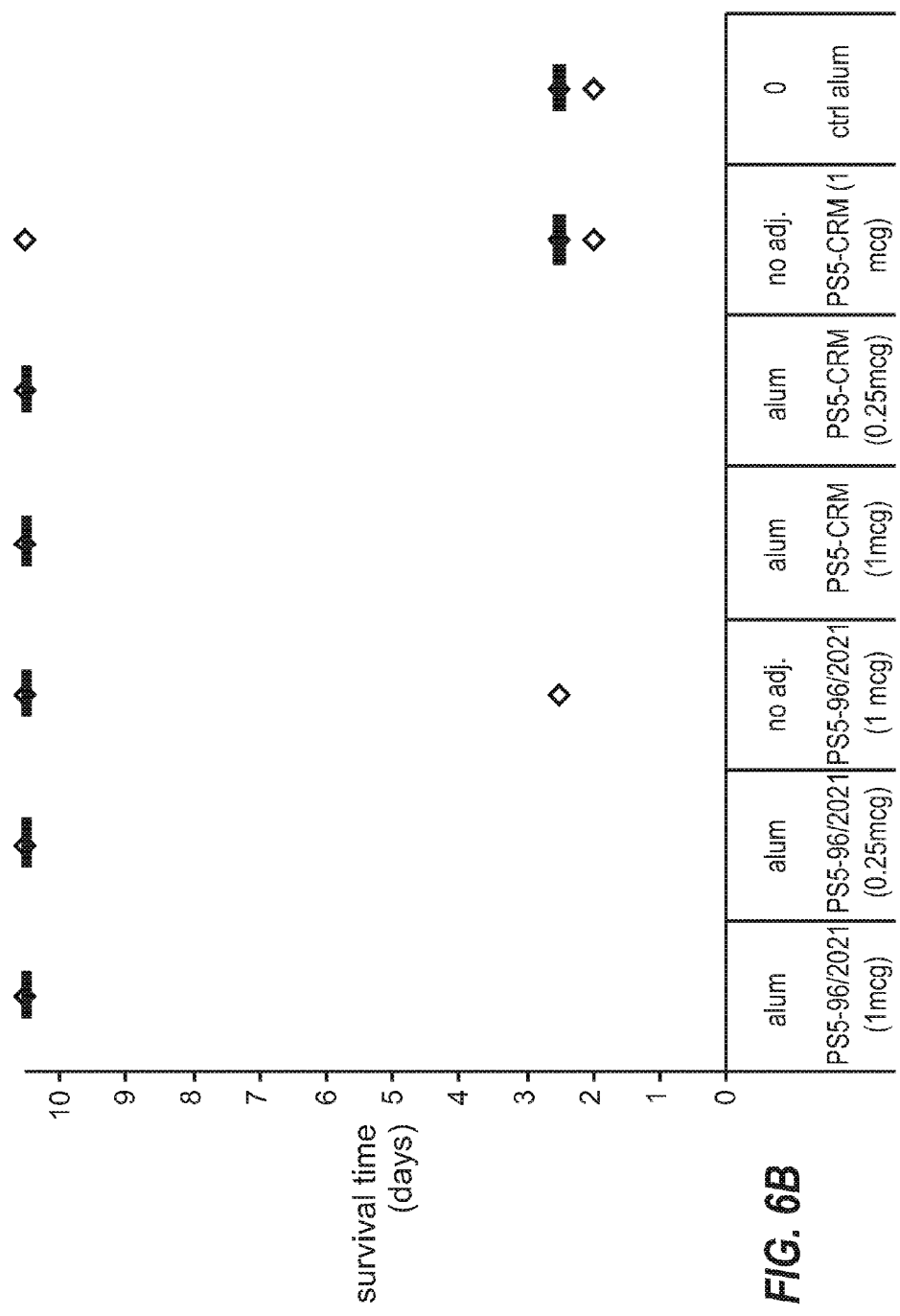

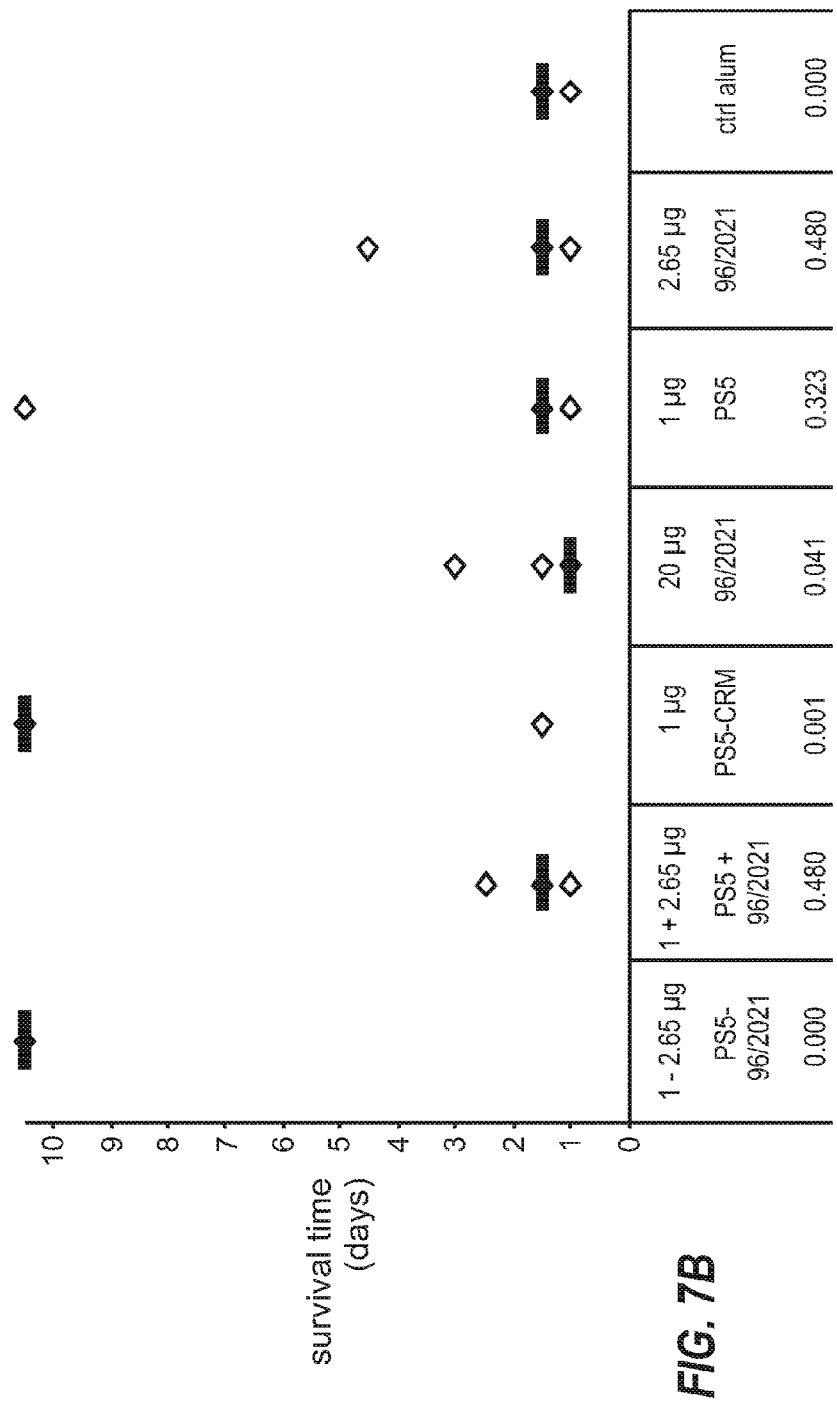

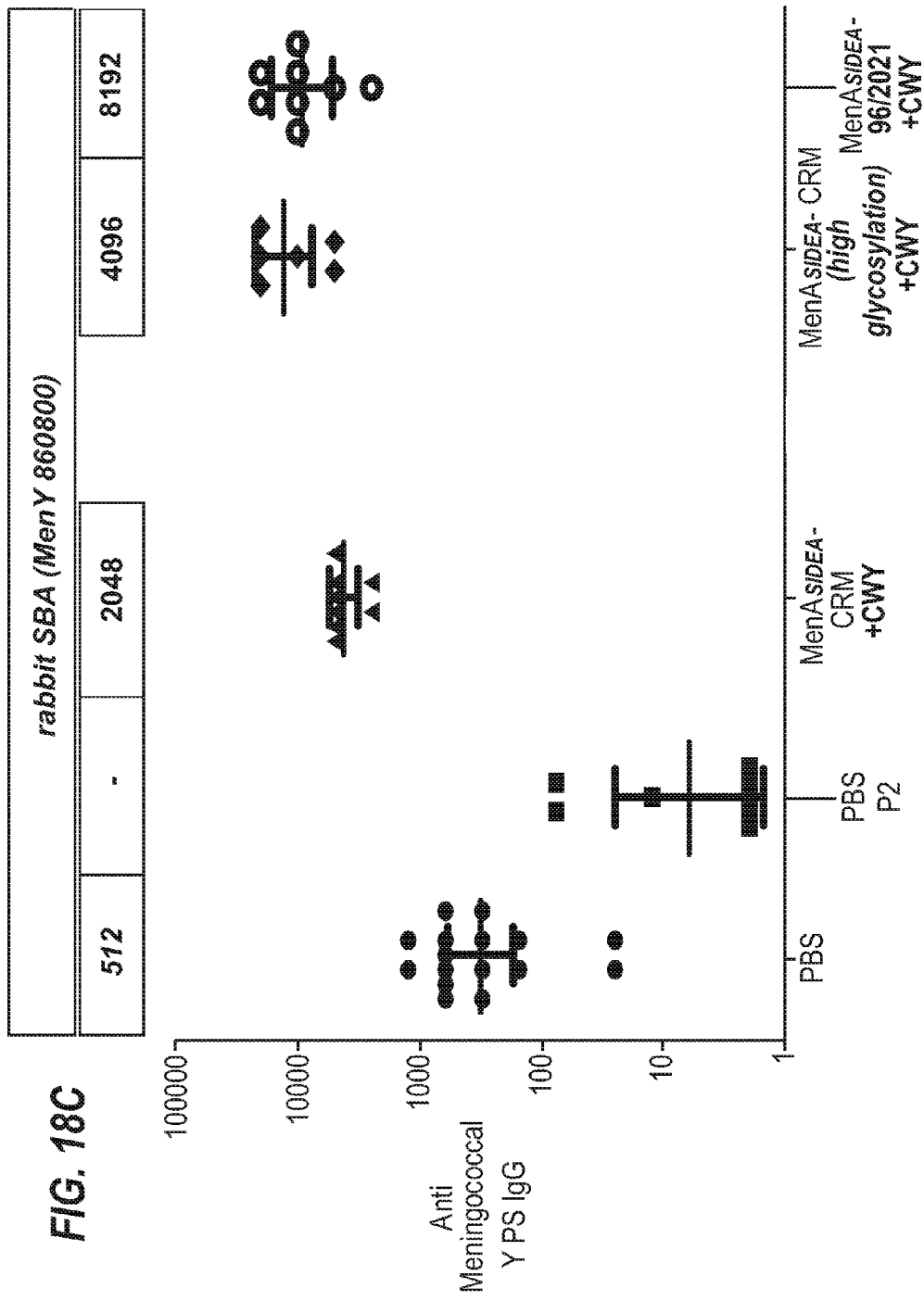

SEQUENCE LISTING

<160> NUMBER OF SEQ ID NOS: 21

<210> SEQ ID NO 1
<211> LENGTH: 167
<212> TYPE: PRT
<213> ORGANISM: Streptococcus pneumoniae

<400> SEQUENCE: 1

Met Lys Ser Ile Thr Lys Lys Ile Lys Ala Thr Leu Ala Gly Val Ala
1               5                   10                  15

Ala Leu Phe Ala Val Phe Ala Pro Ser Phe Val Ser Ala Gln Glu Ser
            20                  25                  30

Ser Thr Tyr Thr Val Lys Glu Gly Asp Thr Leu Ser Glu Ile Ala Glu
        35                  40                  45

Thr His Asn Thr Thr Val Glu Lys Leu Ala Glu Asn Asn His Ile Asp
    50                  55                  60

Asn Ile His Leu Ile Tyr Val Asp Gln Glu Leu Val Ile Asp Gly Pro
65                  70                  75                  80

Val Ala Pro Val Ala Thr Pro Ala Pro Ala Thr Tyr Ala Ala Pro Ala
                85                  90                  95

Ala Gln Asp Glu Thr Val Ser Ala Pro Val Ala Glu Thr Pro Val Val
            100                 105                 110

Ser Glu Thr Val Val Ser Thr Val Ser Gly Ser Glu Ala Glu Ala Lys
        115                 120                 125

Glu Trp Ile Ala Gln Lys Glu Ser Gly Gly Ser Tyr Thr Ala Thr Asn
    130                 135                 140

Gly Arg Tyr Ile Gly Arg Tyr Gly Ser Trp Thr Ala Ala Lys Asn Phe
145                 150                 155                 160

Trp Leu Asn Asn Gly Trp Tyr
                165

<210> SEQ ID NO 2
<211> LENGTH: 195
<212> TYPE: PRT
<213> ORGANISM: Streptococcus pneumoniae

<400> SEQUENCE: 2

Met Lys Ser Ile Thr Lys Lys Ile Lys Ala Thr Leu Ala Gly Val Ala
1               5                   10                  15

Ala Leu Phe Ala Val Phe Ala Pro Ser Phe Val Ser Ala Gln Glu Ser
            20                  25                  30

Ser Thr Tyr Thr Val Lys Glu Gly Asp Thr Leu Ser Glu Ile Ala Glu
        35                  40                  45

Thr His Asn Thr Thr Val Glu Lys Leu Ala Glu Asn Asn His Ile Asp
    50                  55                  60

Asn Ile His Leu Ile Tyr Val Asp Gln Glu Leu Val Ile Asp Gly Pro
65                  70                  75                  80

Val Ala Pro Val Ala Thr Pro Ala Pro Ala Thr Tyr Ala Ala Pro Ala
                85                  90                  95

Ala Gln Asp Glu Thr Val Ser Ala Pro Val Ala Glu Thr Pro Val Val
            100                 105                 110

Ser Glu Thr Val Val Ser Thr Val Ser Gly Ser Glu Ala Glu Ala Lys
        115                 120                 125

Glu Trp Ile Ala Gln Lys Glu Ser Gly Gly Ser Tyr Thr Ala Thr Asn
    130                 135                 140

Gly Arg Tyr Ile Gly Arg Tyr Gln Leu Thr Asp Ser Tyr Leu Asn Gly

```
            145                 150                 155                 160
Asp Tyr Ser Ala Glu Asn Gln Glu Arg Val Ala Asp Ala Tyr Val Ala
                    165                 170                 175
Gly Arg Tyr Gly Ser Trp Thr Ala Ala Lys Asn Phe Trp Leu Asn Asn
                    180                 185                 190
Gly Trp Tyr
        195

<210> SEQ ID NO 3
<211> LENGTH: 392
<212> TYPE: PRT
<213> ORGANISM: Streptococcus pneumoniae

<400> SEQUENCE: 3

Met Lys Lys Lys Ile Leu Ala Ser Leu Leu Ser Thr Val Met Val
1               5                   10                  15

Ser Gln Val Ala Val Leu Thr Thr Ala His Ala Glu Thr Thr Asp Asp
                20                  25                  30

Lys Ile Ala Ala Gln Asp Asn Lys Ile Ser Asn Leu Thr Ala Gln Gln
                35                  40                  45

Gln Glu Ala Gln Lys Gln Val Asp Gln Ile Glu Gln Val Ser Ala
            50                  55                  60

Ile Gln Ala Glu Gln Ser Asn Leu Gln Ala Glu Asn Asp Arg Leu Gln
65                  70                  75                  80

Ala Glu Ser Lys Lys Leu Glu Gly Glu Ile Thr Glu Leu Ser Lys Asn
                85                  90                  95

Ile Val Ser Arg Asn Gln Ser Leu Glu Lys Gln Ala Arg Ser Ala Gln
                100                 105                 110

Thr Asn Gly Ala Val Thr Ser Tyr Ile Asn Thr Ile Val Asn Ser Lys
                115                 120                 125

Ser Ile Thr Glu Ala Ile Ser Arg Val Ala Ala Met Ser Glu Ile Val
            130                 135                 140

Ser Ala Asn Asn Lys Met Leu Glu Gln Gln Lys Ala Asp Lys Lys Ala
145                 150                 155                 160

Ile Ser Glu Lys Gln Val Ala Asn Asn Asp Ala Ile Asn Thr Val Ile
                165                 170                 175

Ala Asn Gln Gln Lys Leu Ala Asp Asp Ala Gln Ala Leu Thr Thr Lys
                180                 185                 190

Gln Ala Glu Leu Lys Ala Ala Glu Leu Ser Leu Ala Ala Glu Lys Ala
                195                 200                 205

Thr Ala Glu Gly Glu Lys Ala Ser Leu Leu Glu Gln Lys Ala Ala Ala
            210                 215                 220

Glu Ala Glu Ala Arg Ala Ala Val Ala Glu Ala Ala Tyr Lys Glu
225                 230                 235                 240

Lys Arg Ala Ser Gln Gln Gln Ser Val Leu Ala Ser Ala Asn Thr Asn
                245                 250                 255

Leu Thr Ala Gln Val Gln Ala Val Ser Glu Ser Ala Ala Pro Val
                260                 265                 270

Arg Ala Lys Val Arg Pro Thr Tyr Ser Thr Asn Ala Ser Ser Tyr Pro
                275                 280                 285

Ile Gly Glu Cys Thr Trp Gly Val Lys Thr Leu Ala Pro Trp Ala Gly
            290                 295                 300

Asp Tyr Trp Gly Asn Gly Ala Gln Trp Ala Thr Ser Ala Ala Ala Ala
305                 310                 315                 320
```

```
Gly Phe Arg Thr Gly Ser Thr Pro Gln Val Gly Ala Ile Ala Cys Trp
            325                 330                 335

Asn Asp Gly Gly Tyr Gly His Val Ala Val Thr Ala Val Glu Ser
            340                 345                 350

Thr Thr Arg Ile Gln Val Ser Glu Ser Asn Tyr Ala Gly Asn Arg Thr
            355                 360                 365

Ile Gly Asn His Arg Gly Trp Phe Asn Pro Thr Thr Ser Glu Gly
370                 375                 380

Phe Val Thr Tyr Ile Tyr Ala Asp
385                 390

<210> SEQ ID NO 4
<211> LENGTH: 366
<212> TYPE: PRT
<213> ORGANISM: Streptococcus pneumoniae

<400> SEQUENCE: 4

Ala Glu Thr Thr Asp Asp Lys Ile Ala Ala Gln Asp Asn Lys Ile Ser
1               5                   10                  15

Asn Leu Thr Ala Gln Gln Gln Glu Ala Gln Lys Gln Val Asp Gln Ile
            20                  25                  30

Gln Glu Gln Val Ser Ala Ile Gln Ala Glu Gln Ser Asn Leu Gln Ala
        35                  40                  45

Glu Asn Asp Arg Leu Gln Ala Glu Ser Lys Leu Glu Gly Glu Ile
    50                  55                  60

Thr Glu Leu Ser Lys Asn Ile Val Ser Arg Asn Gln Ser Leu Glu Lys
65                  70                  75                  80

Gln Ala Arg Ser Ala Gln Thr Asn Gly Ala Val Thr Ser Tyr Ile Asn
                85                  90                  95

Thr Ile Val Asn Ser Lys Ser Ile Thr Glu Ala Ile Ser Arg Val Ala
            100                 105                 110

Ala Met Ser Glu Ile Val Ser Ala Asn Asn Lys Met Leu Glu Gln Gln
        115                 120                 125

Lys Ala Asp Lys Lys Ala Ile Ser Glu Lys Gln Val Ala Asn Asn Asp
    130                 135                 140

Ala Ile Asn Thr Val Ile Ala Asn Gln Gln Lys Leu Ala Asp Asp Ala
145                 150                 155                 160

Gln Ala Leu Thr Thr Lys Gln Ala Glu Leu Lys Ala Ala Glu Leu Ser
                165                 170                 175

Leu Ala Ala Glu Lys Ala Thr Ala Glu Gly Glu Lys Ala Ser Leu Leu
            180                 185                 190

Glu Gln Lys Ala Ala Ala Glu Ala Glu Ala Arg Ala Ala Ala Val Ala
        195                 200                 205

Glu Ala Ala Tyr Lys Glu Lys Arg Ala Ser Gln Gln Ser Val Leu
    210                 215                 220

Ala Ser Ala Asn Thr Asn Leu Thr Ala Gln Val Gln Ala Val Ser Glu
225                 230                 235                 240

Ser Ala Ala Ala Pro Val Arg Ala Lys Val Arg Pro Thr Tyr Ser Thr
                245                 250                 255

Asn Ala Ser Ser Tyr Pro Ile Gly Glu Cys Thr Trp Gly Val Lys Thr
            260                 265                 270

Leu Ala Pro Trp Ala Gly Asp Tyr Trp Gly Asn Gly Ala Gln Trp Ala
        275                 280                 285

Thr Ser Ala Ala Ala Ala Gly Phe Arg Thr Gly Ser Thr Pro Gln Val
    290                 295                 300
```

```
Gly Ala Ile Ala Cys Trp Asn Asp Gly Gly Tyr Gly His Val Ala Val
305                 310                 315                 320

Val Thr Ala Val Glu Ser Thr Thr Arg Ile Gln Val Ser Glu Ser Asn
            325                 330                 335

Tyr Ala Gly Asn Arg Thr Ile Gly Asn His Arg Gly Trp Phe Asn Pro
        340                 345                 350

Thr Thr Thr Ser Glu Gly Phe Val Thr Tyr Ile Tyr Ala Asp
        355                 360                 365

<210> SEQ ID NO 5
<211> LENGTH: 6
<212> TYPE: PRT
<213> ORGANISM: Artificial Sequence
<220> FEATURE:
<223> OTHER INFORMATION: linker

<400> SEQUENCE: 5

Gly Ser Gly Gly Gly Gly
1               5

<210> SEQ ID NO 6
<211> LENGTH: 8
<212> TYPE: PRT
<213> ORGANISM: Artificial Sequence
<220> FEATURE:
<223> OTHER INFORMATION: linker

<400> SEQUENCE: 6

Gly Ser Gly Ser Gly Gly Gly Gly
1               5

<210> SEQ ID NO 7
<211> LENGTH: 5
<212> TYPE: PRT
<213> ORGANISM: Artificial Sequence
<220> FEATURE:
<223> OTHER INFORMATION: linker

<400> SEQUENCE: 7

Ala Ala Ala Leu Glu
1               5

<210> SEQ ID NO 8
<211> LENGTH: 6
<212> TYPE: PRT
<213> ORGANISM: Artificial Sequence
<220> FEATURE:
<223> OTHER INFORMATION: his tag

<400> SEQUENCE: 8

His His His His His His
1               5

<210> SEQ ID NO 9
<211> LENGTH: 555
<212> TYPE: PRT
<213> ORGANISM: Streptococcus pneumoniae

<400> SEQUENCE: 9

Met Val Ser Ala Gln Glu Ser Thr Tyr Thr Val Lys Glu Gly Asp
1               5                   10                  15

Thr Leu Ser Glu Ile Ala Glu Thr His Asn Thr Thr Val Glu Lys Leu
            20                  25                  30
```

```
Ala Glu Asn Asn His Ile Asp Asn Ile His Leu Ile Tyr Val Asp Gln
             35                  40                  45

Glu Leu Val Ile Asp Gly Pro Val Ala Pro Val Thr Pro Ala Pro
 50                  55                  60

Ala Thr Tyr Ala Ala Pro Ala Ala Gln Asp Glu Thr Val Ser Ala Pro
 65                  70                  75                  80

Val Ala Glu Thr Pro Val Val Ser Glu Thr Val Val Ser Thr Val Ser
                 85                  90                  95

Gly Ser Glu Ala Glu Ala Lys Glu Trp Ile Ala Gln Lys Glu Ser Gly
            100                 105                 110

Gly Ser Tyr Thr Ala Thr Asn Gly Arg Tyr Ile Gly Arg Tyr Gln Leu
            115                 120                 125

Thr Asp Ser Tyr Leu Asn Gly Asp Tyr Ser Ala Glu Asn Gln Glu Arg
            130                 135                 140

Val Ala Asp Ala Tyr Val Ala Gly Arg Tyr Gly Ser Trp Thr Ala Ala
145                 150                 155                 160

Lys Asn Phe Trp Leu Asn Asn Gly Trp Tyr Gly Ser Ser Gly Gly
                165                 170                 175

Gly Gly Ala Glu Thr Thr Asp Asp Lys Ile Ala Ala Gln Asp Asn Lys
            180                 185                 190

Ile Ser Asn Leu Thr Ala Gln Gln Glu Ala Gln Lys Gln Val Asp
            195                 200                 205

Gln Ile Gln Glu Gln Val Ser Ala Ile Gln Ala Glu Gln Ser Asn Leu
            210                 215                 220

Gln Ala Glu Asn Asp Arg Leu Gln Ala Glu Ser Lys Lys Leu Glu Gly
225                 230                 235                 240

Glu Ile Thr Glu Leu Ser Lys Asn Ile Val Ser Arg Asn Gln Ser Leu
                245                 250                 255

Glu Lys Gln Ala Arg Ser Ala Gln Thr Asn Gly Ala Val Thr Ser Tyr
            260                 265                 270

Ile Asn Thr Ile Val Asn Ser Lys Ser Ile Thr Glu Ala Ile Ser Arg
            275                 280                 285

Val Ala Ala Met Ser Glu Ile Val Ser Ala Asn Asn Lys Met Leu Glu
290                 295                 300

Gln Gln Lys Ala Asp Lys Lys Ala Ile Ser Glu Lys Gln Val Ala Asn
305                 310                 315                 320

Asn Asp Ala Ile Asn Thr Val Ile Ala Asn Gln Lys Leu Ala Asp
                325                 330                 335

Asp Ala Gln Ala Leu Thr Thr Lys Gln Ala Glu Leu Lys Ala Ala Glu
            340                 345                 350

Leu Ser Leu Ala Ala Glu Lys Ala Thr Ala Glu Gly Glu Lys Ala Ser
            355                 360                 365

Leu Leu Glu Gln Lys Ala Ala Glu Ala Glu Ala Arg Ala Ala Ala
            370                 375                 380

Val Ala Glu Ala Ala Tyr Lys Glu Lys Arg Ala Ser Gln Gln Ser
385                 390                 395                 400

Val Leu Ala Ser Ala Asn Thr Asn Leu Thr Ala Gln Val Gln Ala Val
                405                 410                 415

Ser Glu Ser Ala Ala Pro Val Arg Ala Lys Val Arg Pro Thr Tyr
            420                 425                 430

Ser Thr Asn Ala Ser Ser Tyr Pro Ile Gly Glu Cys Thr Trp Gly Val
            435                 440                 445

Lys Thr Leu Ala Pro Trp Ala Gly Asp Tyr Trp Gly Asn Gly Ala Gln
```

```
                450             455             460
Trp Ala Thr Ser Ala Ala Ala Gly Phe Arg Thr Gly Ser Thr Pro
465                 470                 475                 480

Gln Val Gly Ala Ile Ala Cys Trp Asn Asp Gly Gly Tyr Gly His Val
                    485                 490                 495

Ala Val Val Thr Ala Val Glu Ser Thr Thr Arg Ile Gln Val Ser Glu
                500                 505                 510

Ser Asn Tyr Ala Gly Asn Arg Thr Ile Gly Asn His Arg Gly Trp Phe
            515                 520                 525

Asn Pro Thr Thr Thr Ser Glu Gly Phe Val Thr Tyr Ile Tyr Ala Asp
        530                 535                 540

Ala Ala Ala Leu Glu His His His His His His
545                 550                 555
```

<210> SEQ ID NO 10
<211> LENGTH: 552
<212> TYPE: PRT
<213> ORGANISM: Streptococcus pneumoniae

<400> SEQUENCE: 10

```
Met Ala Glu Thr Thr Asp Asp Lys Ile Ala Ala Gln Asp Asn Lys Ile
1               5                   10                  15

Ser Asn Leu Thr Ala Gln Gln Glu Ala Gln Lys Gln Val Asp Gln
            20                  25                  30

Ile Gln Glu Gln Val Ser Ala Ile Gln Ala Glu Gln Ser Asn Leu Gln
        35                  40                  45

Ala Glu Asn Asp Arg Leu Gln Ala Glu Ser Lys Lys Leu Glu Gly Glu
50                  55                  60

Ile Thr Glu Leu Ser Lys Asn Ile Val Ser Arg Asn Gln Ser Leu Glu
65                  70                  75                  80

Lys Gln Ala Arg Ser Ala Gln Thr Asn Gly Ala Val Thr Ser Tyr Ile
                85                  90                  95

Asn Thr Ile Val Asn Ser Lys Ser Ile Thr Glu Ala Ile Ser Arg Val
            100                 105                 110

Ala Ala Met Ser Glu Ile Val Ser Ala Asn Asn Lys Met Leu Glu Gln
        115                 120                 125

Gln Lys Ala Asp Lys Lys Ala Ile Ser Glu Lys Gln Val Ala Asn Asn
    130                 135                 140

Asp Ala Ile Asn Thr Val Ile Ala Asn Gln Gln Lys Leu Ala Asp Asp
145                 150                 155                 160

Ala Gln Ala Leu Thr Thr Lys Gln Ala Glu Leu Lys Ala Ala Glu Leu
                165                 170                 175

Ser Leu Ala Ala Glu Lys Ala Thr Ala Glu Gly Glu Lys Ala Ser Leu
            180                 185                 190

Leu Glu Gln Lys Ala Ala Glu Ala Glu Ala Arg Ala Ala Ala Val
        195                 200                 205

Ala Glu Ala Ala Tyr Lys Glu Lys Arg Ala Ser Gln Gln Ser Val
    210                 215                 220

Leu Ala Ser Ala Asn Thr Asn Leu Thr Ala Gln Val Gln Ala Val Ser
225                 230                 235                 240

Glu Ser Ala Ala Ala Pro Val Arg Ala Lys Val Arg Pro Thr Tyr Ser
                245                 250                 255

Thr Asn Ala Ser Ser Tyr Pro Ile Gly Glu Cys Thr Trp Gly Val Lys
            260                 265                 270
```

```
Thr Leu Ala Pro Trp Ala Gly Asp Tyr Trp Gly Asn Gly Ala Gln Trp
            275                 280                 285

Ala Thr Ser Ala Ala Ala Gly Phe Arg Thr Gly Ser Thr Pro Gln
    290                 295                 300

Val Gly Ala Ile Ala Cys Trp Asn Asp Gly Gly Tyr Gly His Val Ala
305                 310                 315                 320

Val Val Thr Ala Val Glu Ser Thr Arg Ile Gln Val Ser Glu Ser
            325                 330                 335

Asn Tyr Ala Gly Asn Arg Thr Ile Gly Asn His Arg Gly Trp Phe Asn
            340                 345                 350

Pro Thr Thr Thr Ser Glu Gly Phe Val Thr Tyr Ile Tyr Ala Asp Gly
            355                 360                 365

Ser Gly Ser Gly Gly Gly Val Ser Ala Gln Glu Ser Ser Thr Tyr
    370                 375                 380

Thr Val Lys Glu Gly Asp Thr Leu Ser Glu Ile Ala Glu Thr His Asn
385                 390                 395                 400

Thr Thr Val Glu Lys Leu Ala Glu Asn Asn His Ile Asp Asn Ile His
                405                 410                 415

Leu Ile Tyr Val Asp Gln Glu Leu Val Ile Asp Gly Pro Val Ala Pro
            420                 425                 430

Val Ala Thr Pro Ala Pro Ala Thr Tyr Ala Ala Pro Ala Ala Gln Asp
            435                 440                 445

Glu Thr Val Ser Ala Pro Val Ala Glu Thr Pro Val Val Ser Glu Thr
    450                 455                 460

Val Val Ser Thr Val Ser Gly Ser Glu Ala Glu Ala Lys Glu Trp Ile
465                 470                 475                 480

Ala Gln Lys Glu Ser Gly Gly Ser Tyr Thr Ala Thr Asn Gly Arg Tyr
                485                 490                 495

Ile Gly Arg Tyr Gln Leu Thr Asp Ser Tyr Leu Asn Gly Asp Tyr Ser
            500                 505                 510

Ala Glu Asn Gln Glu Arg Val Ala Asp Ala Tyr Val Ala Gly Arg Tyr
            515                 520                 525

Gly Ser Trp Thr Ala Ala Lys Asn Phe Trp Leu Asn Asn Gly Trp Tyr
    530                 535                 540

Leu Glu His His His His His His
545                 550

<210> SEQ ID NO 11
<211> LENGTH: 1093
<212> TYPE: PRT
<213> ORGANISM: Streptococcus pneumoniae

<400> SEQUENCE: 11

Ile Ala Glu Glu Asp Lys Ala Lys Leu Ala Ile Pro Gly Ser Arg Ile
1               5                   10                  15

Gln Ala Thr Gly Tyr Leu Glu Gly Gln Pro Ile His Ala Thr Leu Val
            20                  25                  30

Val Glu Glu Gly Asn Pro Ala Ala Pro Val Val Pro Thr Val Thr Val
        35                  40                  45

Gly Gly Glu Ala Val Thr Gly Leu Thr Ser Arg Gln Pro Met Gln Tyr
    50                  55                  60

Arg Thr Leu Ser Tyr Gly Ala Gln Leu Pro Glu Val Thr Ala Ser Ala
65                  70                  75                  80

Glu Asn Ala Asp Val Thr Val Leu Gln Ala Ser Ala Ala Asn Gly Met
                85                  90                  95
```

```
Arg Ala Ser Ile Phe Ile Gln Pro Lys Asp Gly Gly Pro Leu Gln Thr
            100                 105                 110

Tyr Ala Ile Gln Phe Leu Glu Ala Pro Lys Ile Ala His Leu Ser
            115                 120                 125

Leu Gln Val Glu Lys Ala Asp Ser Leu Lys Glu Asp Gln Thr Val Lys
            130                 135                 140

Leu Ser Val Arg Ala His Tyr Gln Asp Gly Thr Gln Ala Val Leu Pro
145                     150                 155                 160

Ala Asp Lys Val Thr Phe Ser Thr Ser Gly Glu Gly Val Ala Ile
                    165                 170                 175

Arg Lys Gly Met Leu Glu Leu His Lys Pro Gly Ala Val Thr Leu Asn
                180                 185                 190

Ala Glu Tyr Glu Gly Ala Lys Gly Gln Val Glu Leu Thr Ile Gln Ala
            195                 200                 205

Asn Thr Glu Lys Lys Ile Ala Gln Ser Ile Arg Pro Val Asn Val Val
            210                 215                 220

Thr Asp Leu His Gln Glu Pro Ser Leu Pro Ala Thr Val Thr Val Glu
225                     230                 235                 240

Tyr Asp Lys Gly Phe Pro Lys Thr His Lys Val Thr Trp Gln Ala Ile
                    245                 250                 255

Pro Lys Glu Lys Leu Asp Ser Tyr Gln Ile Phe Glu Val Leu Gly Lys
            260                 265                 270

Val Glu Gly Ile Asp Leu Glu Ala Arg Ala Lys Val Ser Val Glu Gly
            275                 280                 285

Ile Val Ser Val Glu Val Ser Val Thr Thr Pro Ile Ala Glu Ala
            290                 295                 300

Pro Gln Leu Pro Glu Ser Val Arg Thr Tyr Asp Ser Asn Gly His Val
305                     310                 315                 320

Ser Ser Ala Lys Val Ala Trp Asp Ala Ile Arg Pro Glu Gln Tyr Ala
                    325                 330                 335

Lys Glu Gly Val Phe Thr Val Asn Gly Arg Leu Glu Gly Thr Gln Leu
            340                 345                 350

Thr Thr Lys Leu His Val Arg Val Ser Ala Gln Thr Glu Gln Gly Ala
            355                 360                 365

Asn Ile Ser Asp Gln Trp Thr Gly Ser Glu Leu Pro Leu Ala Phe Ala
            370                 375                 380

Ser Asp Ser Asn Pro Ser Asp Pro Val Ser Asn Val Asn Asp Lys Leu
385                     390                 395                 400

Ile Ser Tyr Asn Asn Gln Pro Ala Asn Arg Trp Thr Asn Trp Asn Arg
                    405                 410                 415

Ser Asn Pro Glu Ala Ser Val Gly Val Leu Phe Gly Asp Ser Gly Ile
            420                 425                 430

Leu Ser Lys Arg Ser Val Asp Asn Leu Ser Val Gly Phe His Glu Asp
            435                 440                 445

His Gly Val Gly Ala Pro Lys Ser Tyr Val Ile Glu Tyr Tyr Val Gly
            450                 455                 460

Lys Thr Val Pro Thr Ala Pro Lys Asn Pro Ser Phe Val Gly Asn Glu
465                     470                 475                 480

Asp His Val Phe Asn Asp Ser Ala Asn Trp Lys Pro Val Thr Asn Leu
                    485                 490                 495

Lys Ala Pro Ala Gln Leu Lys Ala Gly Glu Met Asn His Phe Ser Phe
            500                 505                 510
```

-continued

```
Asp Lys Val Glu Thr Tyr Ala Ile Arg Ile Arg Met Lys Ala Asp
            515                 520                 525
Asn Lys Arg Gly Thr Ser Ile Thr Glu Val Gln Ile Phe Ala Lys Gln
530                 535                 540
Val Ala Ala Ala Lys Gln Gly Gln Thr Arg Ile Gln Val Asp Gly Lys
545                 550                 555                 560
Asp Leu Ala Asn Phe Asn Pro Asp Leu Thr Asp Tyr Tyr Leu Glu Ser
                565                 570                 575
Val Asp Gly Lys Val Pro Ala Val Thr Ala Asn Val Ser Asn Asn Gly
            580                 585                 590
Leu Ala Thr Val Val Pro Ser Val Arg Glu Gly Glu Pro Val Arg Val
            595                 600                 605
Ile Ala Lys Ala Glu Asn Gly Asp Ile Leu Gly Glu Tyr Arg Leu His
610                 615                 620
Phe Thr Lys Asp Lys Asn Leu Leu Ser His Lys Pro Val Ala Ala Val
625                 630                 635                 640
Lys Gln Ala Arg Leu Leu Gln Val Gly Gln Ala Leu Glu Leu Pro Thr
                645                 650                 655
Lys Val Pro Val Tyr Phe Thr Gly Lys Asp Gly Tyr Glu Thr Lys Asp
            660                 665                 670
Leu Thr Val Glu Trp Glu Val Pro Ala Glu Asn Leu Thr Lys Ala
            675                 680                 685
Gly Gln Phe Thr Val Arg Gly Arg Val Leu Gly Ser Asn Leu Val Ala
            690                 695                 700
Glu Val Thr Val Arg Val Thr Asp Lys Leu Gly Glu Thr Leu Ser Asp
705                 710                 715                 720
Asn Pro Asn Tyr Asp Glu Asn Ser Asn Gln Ala Phe Ala Ser Ala Thr
                725                 730                 735
Asn Asp Ile Asp Lys Asn Ser His Asp Arg Val Asp Tyr Leu Asn Asp
            740                 745                 750
Gly Asp His Ser Glu Asn Arg Arg Trp Thr Asn Trp Ser Pro Thr Pro
            755                 760                 765
Ser Ser Asn Pro Glu Val Ser Ala Gly Val Ile Phe Arg Glu Asn Gly
770                 775                 780
Lys Ile Val Glu Arg Thr Val Ala Gln Ala Lys Leu His Phe Phe Ala
785                 790                 795                 800
Asp Ser Gly Thr Asp Ala Pro Ser Lys Leu Val Leu Glu Arg Tyr Val
                805                 810                 815
Gly Pro Gly Phe Glu Val Pro Thr Tyr Tyr Ser Asn Tyr Gln Ala Tyr
            820                 825                 830
Glu Ser Gly His Pro Phe Asn Asn Pro Glu Asn Trp Glu Ala Val Pro
            835                 840                 845
Tyr Arg Ala Asp Lys Asp Ile Ala Ala Gly Asp Glu Ile Asn Val Thr
850                 855                 860
Phe Lys Ala Val Lys Ala Lys Val Met Arg Trp Arg Met Glu Arg Lys
865                 870                 875                 880
Ala Asp Lys Ser Gly Val Ala Met Ile Glu Met Thr Phe Leu Ala Pro
                885                 890                 895
Ser Glu Leu Pro Gln Glu Ser Thr Gln Ser Lys Ile Leu Val Asp Gly
            900                 905                 910
Lys Glu Leu Ala Asp Phe Ala Glu Asn Arg Gln Asp Tyr Gln Ile Thr
            915                 920                 925
Tyr Lys Gly Gln Arg Pro Lys Val Ser Val Glu Glu Asn Asn Gln Val
```

```
                        930                 935                 940
Ala Ser Thr Val Val Asp Ser Gly Glu Asp Ser Leu Pro Val Leu Val
945                 950                 955                 960

Arg Leu Val Ser Glu Ser Gly Lys Gln Val Lys Glu Tyr Arg Ile Gln
                965                 970                 975

Leu Thr Lys Glu Lys Pro Val Ser Ala Val Gln Glu Asp Leu Pro Lys
            980                 985                 990

Leu Glu Phe Val Glu Lys Asp Leu Ala Tyr Lys Thr Val Glu Lys Lys
        995                 1000                1005

Asp Ser Thr Leu Tyr Leu Gly Glu Thr Arg Val Glu Gln Glu Gly Lys
    1010                1015                1020

Val Gly Lys Glu Arg Ile Phe Thr Val Ile Asn Pro Asp Gly Ser Lys
1025                1030                1035                1040

Glu Glu Lys Leu Arg Glu Val Val Glu Val Pro Thr Arg Ile Val
                1045                1050                1055

Leu Val Gly Thr Lys Pro Val Ala Gln Glu Ala Lys Lys Pro Gln Val
            1060                1065                1070

Ser Glu Lys Ala Asp Thr Lys Pro Ile Asp Ser Ser Glu Ala Asp Gln
        1075                1080                1085

Thr Asn Lys Ala Gln
    1090
```

<210> SEQ ID NO 12
<211> LENGTH: 128
<212> TYPE: PRT
<213> ORGANISM: Streptococcus pneumoniae

<400> SEQUENCE: 12

```
Met Glu Lys Asp Met Asn Leu Lys Arg Glu Gln Glu Phe Val Ser Gln
1               5                   10                  15

Tyr His Phe Asp Ala Arg Asn Phe Glu Trp Glu Asn Glu Asn Gly Ala
            20                  25                  30

Pro Glu Thr Lys Val Asp Val Asn Phe Gln Leu Leu Gln His Asp Gln
        35                  40                  45

Glu Asn Gln Val Thr Ser Leu Ile Val Ile Leu Ser Phe Met Ile Val
    50                  55                  60

Phe Asp Lys Phe Val Ile Ser Gly Thr Ile Ser Gln Val Asn His Ile
65                  70                  75                  80

Asp Gly Arg Ile Val Asn Glu Pro Asn Glu Leu Asn Gln Glu Glu Val
                85                  90                  95

Glu Thr Leu Ala Arg Pro Cys Leu Asn Met Leu Asn Arg Leu Thr Tyr
            100                 105                 110

Glu Val Thr Glu Ile Ala Leu Asp Leu Pro Gly Ile Asn Leu Glu Phe
        115                 120                 125
```

<210> SEQ ID NO 13
<211> LENGTH: 259
<212> TYPE: PRT
<213> ORGANISM: Streptococcus pneumoniae

<400> SEQUENCE: 13

```
Met Lys Lys Asn Ser Leu Tyr Ile Ile Ser Ser Leu Phe Phe Ala Cys
1               5                   10                  15

Val Leu Phe Val Tyr Ala Thr Ala Thr Asn Phe Gln Asn Ser Thr Ser
            20                  25                  30

Ala Arg Gln Val Lys Thr Glu Thr Tyr Thr Asn Thr Val Thr Asn Val
```

```
            35                  40                  45
Pro Ile Asp Ile Arg Tyr Asn Ser Asp Lys Tyr Phe Ile Ser Gly Phe
 50                  55                  60

Ala Ser Glu Val Ser Val Leu Thr Gly Ala Asn Arg Leu Ser Leu
 65                  70                  75                  80

Ala Ser Glu Met Gln Glu Ser Thr Arg Lys Phe Lys Val Thr Ala Asp
                     85                  90                  95

Leu Thr Asp Ala Gly Val Gly Thr Ile Glu Val Pro Leu Ser Ile Glu
                100                 105                 110

Asp Leu Pro Asn Gly Leu Thr Ala Val Ala Thr Pro Gln Lys Ile Thr
                115                 120                 125

Val Lys Ile Gly Lys Lys Ala Gln Lys Asp Lys Val Lys Ile Val Pro
130                 135                 140

Glu Ile Asp Pro Ser Gln Ile Asp Ser Arg Val Gln Ile Glu Asn Val
145                 150                 155                 160

Met Val Ser Asp Lys Glu Val Ser Ile Thr Ser Asp Gln Glu Thr Leu
                165                 170                 175

Asp Arg Ile Asp Lys Ile Ile Ala Val Leu Pro Thr Ser Glu Arg Ile
                180                 185                 190

Thr Gly Asn Tyr Ser Gly Ser Val Pro Leu Gln Ala Ile Asp Arg Asn
                195                 200                 205

Gly Val Val Leu Pro Ala Val Ile Thr Pro Phe Asp Thr Ile Met Lys
210                 215                 220

Val Thr Thr Lys Pro Val Ala Pro Ser Ser Thr Ser Asn Ser Ser
225                 230                 235                 240

Thr Ser Ser Ser Glu Thr Ser Ser Thr Lys Ala Thr Ser Ser
                245                 250                 255

Lys Thr Asn

<210> SEQ ID NO 14
<211> LENGTH: 141
<212> TYPE: PRT
<213> ORGANISM: Streptococcus pneumoniae

<400> SEQUENCE: 14

Val Ser Ala Gln Glu Ser Ser Thr Tyr Thr Val Lys Glu Gly Asp Thr
 1               5                  10                  15

Leu Ser Glu Ile Ala Glu Thr His Asn Thr Thr Val Glu Lys Leu Ala
                 20                  25                  30

Glu Asn Asn His Ile Asp Asn Ile His Leu Ile Tyr Val Asp Gln Glu
                 35                  40                  45

Leu Val Ile Asp Gly Pro Val Ala Pro Val Ala Thr Pro Ala Pro Ala
 50                  55                  60

Thr Tyr Ala Ala Pro Ala Ala Gln Asp Glu Thr Val Ser Ala Pro Val
 65                  70                  75                  80

Ala Glu Thr Pro Val Val Ser Glu Thr Val Val Ser Thr Val Ser Gly
                 85                  90                  95

Ser Glu Ala Glu Ala Lys Glu Trp Ile Ala Gln Lys Glu Ser Gly Gly
                100                 105                 110

Ser Tyr Thr Ala Thr Asn Gly Arg Tyr Ile Gly Arg Tyr Gly Ser Trp
                115                 120                 125

Thr Ala Ala Lys Asn Phe Trp Leu Asn Asn Gly Trp Tyr
130                 135                 140
```

```
<210> SEQ ID NO 15
<211> LENGTH: 169
<212> TYPE: PRT
<213> ORGANISM: Streptococcus pneumoniae

<400> SEQUENCE: 15

Val Ser Ala Gln Glu Ser Ser Thr Tyr Thr Val Lys Glu Gly Asp Thr
  1               5                  10                  15

Leu Ser Glu Ile Ala Glu Thr His Asn Thr Thr Val Glu Lys Leu Ala
             20                  25                  30

Glu Asn Asn His Ile Asp Asn Ile His Leu Ile Tyr Val Asp Gln Glu
         35                  40                  45

Leu Val Ile Asp Gly Pro Val Ala Pro Val Ala Thr Pro Ala Pro Ala
 50                  55                  60

Thr Tyr Ala Ala Pro Ala Ala Gln Asp Glu Thr Val Ser Ala Pro Val
 65                  70                  75                  80

Ala Glu Thr Pro Val Val Ser Glu Thr Val Val Ser Thr Val Ser Gly
                 85                  90                  95

Ser Glu Ala Glu Ala Lys Glu Trp Ile Ala Gln Lys Glu Ser Gly Gly
             100                 105                 110

Ser Tyr Thr Ala Thr Asn Gly Arg Tyr Ile Gly Arg Tyr Gln Leu Thr
         115                 120                 125

Asp Ser Tyr Leu Asn Gly Asp Tyr Ser Ala Glu Asn Gln Glu Arg Val
130                 135                 140

Ala Asp Ala Tyr Val Ala Gly Arg Tyr Gly Ser Trp Thr Ala Ala Lys
145                 150                 155                 160

Asn Phe Trp Leu Asn Asn Gly Trp Tyr
                165

<210> SEQ ID NO 16
<211> LENGTH: 167
<212> TYPE: PRT
<213> ORGANISM: Streptococcus pneumoniae
<220> FEATURE:
<221> NAME/KEY: misc_feature
<222> LOCATION: 1
<223> OTHER INFORMATION: Xaa is L-homoallylglycine

<400> SEQUENCE: 16

Xaa Lys Ser Ile Thr Lys Lys Ile Lys Ala Thr Leu Ala Gly Val Ala
  1               5                  10                  15

Ala Leu Phe Ala Val Phe Ala Pro Ser Phe Val Ser Ala Gln Glu Ser
             20                  25                  30

Ser Thr Tyr Thr Val Lys Glu Gly Asp Thr Leu Ser Glu Ile Ala Glu
         35                  40                  45

Thr His Asn Thr Thr Val Glu Lys Leu Ala Glu Asn Asn His Ile Asp
 50                  55                  60

Asn Ile His Leu Ile Tyr Val Asp Gln Glu Leu Val Ile Asp Gly Pro
 65                  70                  75                  80

Val Ala Pro Val Ala Thr Pro Ala Pro Ala Thr Tyr Ala Ala Pro Ala
                 85                  90                  95

Ala Gln Asp Glu Thr Val Ser Ala Pro Val Ala Glu Thr Pro Val Val
             100                 105                 110

Ser Glu Thr Val Val Ser Thr Val Ser Gly Ser Glu Ala Glu Ala Lys
         115                 120                 125

Glu Trp Ile Ala Gln Lys Glu Ser Gly Gly Ser Tyr Thr Ala Thr Asn
130                 135                 140
```

```
Gly Arg Tyr Ile Gly Arg Tyr Gly Ser Trp Thr Ala Ala Lys Asn Phe
145                 150                 155                 160

Trp Leu Asn Asn Gly Trp Tyr
                165
```

<210> SEQ ID NO 17
<211> LENGTH: 195
<212> TYPE: PRT
<213> ORGANISM: Streptococcus pneumoniae
<220> FEATURE:
<221> NAME/KEY: misc_feature
<222> LOCATION: 1
<223> OTHER INFORMATION: Xaa is L-homoallylglycine

<400> SEQUENCE: 17

```
Xaa Lys Ser Ile Thr Lys Lys Ile Lys Ala Thr Leu Ala Gly Val Ala
1               5                   10                  15

Ala Leu Phe Ala Val Phe Ala Pro Ser Phe Val Ser Ala Gln Glu Ser
                20                  25                  30

Ser Thr Tyr Thr Val Lys Glu Gly Asp Thr Leu Ser Glu Ile Ala Glu
            35                  40                  45

Thr His Asn Thr Thr Val Glu Lys Leu Ala Glu Asn Asn His Ile Asp
        50                  55                  60

Asn Ile His Leu Ile Tyr Val Asp Gln Glu Leu Val Ile Asp Gly Pro
65                  70                  75                  80

Val Ala Pro Val Ala Thr Pro Ala Pro Ala Thr Tyr Ala Ala Pro Ala
                85                  90                  95

Ala Gln Asp Glu Thr Val Ser Ala Pro Val Ala Glu Thr Pro Val Val
            100                 105                 110

Ser Glu Thr Val Val Ser Thr Val Ser Gly Ser Glu Ala Glu Ala Lys
        115                 120                 125

Glu Trp Ile Ala Gln Lys Glu Ser Gly Gly Ser Tyr Thr Ala Thr Asn
130                 135                 140

Gly Arg Tyr Ile Gly Arg Tyr Gln Leu Thr Asp Ser Tyr Leu Asn Gly
145                 150                 155                 160

Asp Tyr Ser Ala Glu Asn Gln Glu Arg Val Ala Asp Ala Tyr Val Ala
                165                 170                 175

Gly Arg Tyr Gly Ser Trp Thr Ala Ala Lys Asn Phe Trp Leu Asn Asn
            180                 185                 190

Gly Trp Tyr
        195
```

<210> SEQ ID NO 18
<211> LENGTH: 392
<212> TYPE: PRT
<213> ORGANISM: Streptococcus pneumoniae
<220> FEATURE:
<221> NAME/KEY: misc_feature
<222> LOCATION: 1, 15, 140, 150
<223> OTHER INFORMATION: Xaa is L-homoallylglycine

<400> SEQUENCE: 18

```
Xaa Lys Lys Lys Ile Leu Ala Ser Leu Leu Leu Ser Thr Val Xaa Val
1               5                   10                  15

Ser Gln Val Ala Val Leu Thr Thr Ala His Ala Glu Thr Asp Asp
                20                  25                  30

Lys Ile Ala Ala Gln Asp Asn Lys Ile Ser Asn Leu Thr Ala Gln Gln
            35                  40                  45

Gln Glu Ala Gln Lys Gln Val Asp Gln Ile Gln Glu Gln Val Ser Ala
```

```
                    50                  55                  60
Ile Gln Ala Glu Gln Ser Asn Leu Gln Ala Glu Asn Asp Arg Leu Gln
 65                  70                  75                  80

Ala Glu Ser Lys Lys Leu Glu Gly Glu Ile Thr Glu Leu Ser Lys Asn
                 85                  90                  95

Ile Val Ser Arg Asn Gln Ser Leu Glu Lys Gln Ala Arg Ser Ala Gln
            100                 105                 110

Thr Asn Gly Ala Val Thr Ser Tyr Ile Asn Thr Ile Val Asn Ser Lys
        115                 120                 125

Ser Ile Thr Glu Ala Ile Ser Arg Val Ala Ala Xaa Ser Glu Ile Val
    130                 135                 140

Ser Ala Asn Asn Lys Xaa Leu Glu Gln Gln Lys Ala Asp Lys Lys Ala
145                 150                 155                 160

Ile Ser Glu Lys Gln Val Ala Asn Asn Asp Ala Ile Asn Thr Val Ile
                165                 170                 175

Ala Asn Gln Gln Lys Leu Ala Asp Asp Ala Gln Ala Leu Thr Thr Lys
            180                 185                 190

Gln Ala Glu Leu Lys Ala Ala Glu Leu Ser Leu Ala Ala Glu Lys Ala
        195                 200                 205

Thr Ala Glu Gly Glu Lys Ala Ser Leu Leu Glu Gln Lys Ala Ala Ala
    210                 215                 220

Glu Ala Glu Ala Arg Ala Ala Val Ala Glu Ala Ala Tyr Lys Glu
225                 230                 235                 240

Lys Arg Ala Ser Gln Gln Gln Ser Val Leu Ala Ser Ala Asn Thr Asn
                245                 250                 255

Leu Thr Ala Gln Val Gln Ala Val Ser Glu Ser Ala Ala Ala Pro Val
            260                 265                 270

Arg Ala Lys Val Arg Pro Thr Tyr Ser Thr Asn Ala Ser Ser Tyr Pro
        275                 280                 285

Ile Gly Glu Cys Thr Trp Gly Val Lys Thr Leu Ala Pro Trp Ala Gly
    290                 295                 300

Asp Tyr Trp Gly Asn Gly Ala Gln Trp Ala Thr Ser Ala Ala Ala Ala
305                 310                 315                 320

Gly Phe Arg Thr Gly Ser Thr Pro Gln Val Gly Ala Ile Ala Cys Trp
                325                 330                 335

Asn Asp Gly Gly Tyr Gly His Val Ala Val Val Thr Ala Val Glu Ser
            340                 345                 350

Thr Thr Arg Ile Gln Val Ser Glu Ser Asn Tyr Ala Gly Asn Arg Thr
        355                 360                 365

Ile Gly Asn His Arg Gly Trp Phe Asn Pro Thr Thr Ser Glu Gly
    370                 375                 380

Phe Val Thr Tyr Ile Tyr Ala Asp
385                 390

<210> SEQ ID NO 19
<211> LENGTH: 366
<212> TYPE: PRT
<213> ORGANISM: Streptococcus pneumoniae
<220> FEATURE:
<221> NAME/KEY: misc_feature
<222> LOCATION: 114, 124
<223> OTHER INFORMATION: Xaa is L-homoallylglycine

<400> SEQUENCE: 19

Ala Glu Thr Thr Asp Asp Lys Ile Ala Ala Gln Asp Asn Lys Ile Ser
 1               5                  10                  15
```

```
Asn Leu Thr Ala Gln Gln Glu Ala Gln Lys Gln Val Asp Gln Ile
            20                  25                  30

Gln Glu Gln Val Ser Ala Ile Gln Ala Glu Gln Ser Asn Leu Gln Ala
        35                  40                  45

Glu Asn Asp Arg Leu Gln Ala Glu Ser Lys Leu Glu Gly Glu Ile
 50                  55                  60

Thr Glu Leu Ser Lys Asn Ile Val Ser Arg Asn Gln Ser Leu Glu Lys
 65                  70                  75                  80

Gln Ala Arg Ser Ala Gln Thr Asn Gly Ala Val Thr Ser Tyr Ile Asn
                85                  90                  95

Thr Ile Val Asn Ser Lys Ser Ile Thr Glu Ala Ile Ser Arg Val Ala
            100                 105                 110

Ala Xaa Ser Glu Ile Val Ser Ala Asn Asn Lys Xaa Leu Glu Gln Gln
        115                 120                 125

Lys Ala Asp Lys Lys Ala Ile Ser Glu Lys Gln Val Ala Asn Asn Asp
130                 135                 140

Ala Ile Asn Thr Val Ile Ala Asn Gln Gln Lys Leu Ala Asp Asp Ala
145                 150                 155                 160

Gln Ala Leu Thr Thr Lys Gln Ala Glu Leu Lys Ala Ala Glu Leu Ser
                165                 170                 175

Leu Ala Ala Glu Lys Ala Thr Ala Glu Gly Glu Lys Ala Ser Leu Leu
            180                 185                 190

Glu Gln Lys Ala Ala Ala Glu Ala Glu Ala Arg Ala Ala Val Ala
        195                 200                 205

Glu Ala Ala Tyr Lys Glu Lys Arg Ala Ser Gln Gln Ser Val Leu
 210                 215                 220

Ala Ser Ala Asn Thr Asn Leu Thr Ala Gln Val Gln Ala Val Ser Glu
225                 230                 235                 240

Ser Ala Ala Ala Pro Val Arg Ala Lys Val Arg Pro Thr Tyr Ser Thr
                245                 250                 255

Asn Ala Ser Ser Tyr Pro Ile Gly Glu Cys Thr Trp Gly Val Lys Thr
            260                 265                 270

Leu Ala Pro Trp Ala Gly Asp Tyr Trp Gly Asn Gly Ala Gln Trp Ala
        275                 280                 285

Thr Ser Ala Ala Ala Gly Phe Arg Thr Gly Ser Thr Pro Gln Val
 290                 295                 300

Gly Ala Ile Ala Cys Trp Asn Asp Gly Gly Tyr Gly His Val Ala Val
305                 310                 315                 320

Val Thr Ala Val Glu Ser Thr Thr Arg Ile Gln Val Ser Glu Ser Asn
                325                 330                 335

Tyr Ala Gly Asn Arg Thr Ile Gly Asn His Arg Gly Trp Phe Asn Pro
            340                 345                 350

Thr Thr Thr Ser Glu Gly Phe Val Thr Tyr Ile Tyr Ala Asp
        355                 360                 365

<210> SEQ ID NO 20
<211> LENGTH: 555
<212> TYPE: PRT
<213> ORGANISM: Streptococcus pneumoniae
<220> FEATURE:
<221> NAME/KEY: misc_feature
<222> LOCATION: 1, 292, 302
<223> OTHER INFORMATION: Xaa is L-homoallylglycine

<400> SEQUENCE: 20
```

```
Xaa Val Ser Ala Gln Glu Ser Ser Thr Tyr Thr Val Lys Glu Gly Asp
1               5                   10                  15

Thr Leu Ser Glu Ile Ala Glu Thr His Asn Thr Thr Val Glu Lys Leu
            20                  25                  30

Ala Glu Asn Asn His Ile Asp Asn Ile His Leu Ile Tyr Val Asp Gln
            35                  40                  45

Glu Leu Val Ile Asp Gly Pro Val Ala Pro Val Ala Thr Pro Ala Pro
        50                  55                  60

Ala Thr Tyr Ala Ala Pro Ala Ala Gln Asp Glu Thr Val Ser Ala Pro
65                  70                  75                  80

Val Ala Glu Thr Pro Val Val Ser Glu Thr Val Val Ser Thr Val Ser
                85                  90                  95

Gly Ser Glu Ala Glu Ala Lys Glu Trp Ile Ala Gln Lys Glu Ser Gly
            100                 105                 110

Gly Ser Tyr Thr Ala Thr Asn Gly Arg Tyr Ile Gly Arg Tyr Gln Leu
            115                 120                 125

Thr Asp Ser Tyr Leu Asn Gly Asp Tyr Ser Ala Glu Asn Gln Glu Arg
        130                 135                 140

Val Ala Asp Ala Tyr Val Ala Gly Arg Tyr Gly Ser Trp Thr Ala Ala
145                 150                 155                 160

Lys Asn Phe Trp Leu Asn Asn Gly Trp Tyr Gly Ser Gly Ser Gly Gly
                165                 170                 175

Gly Gly Ala Glu Thr Thr Asp Asp Lys Ile Ala Ala Gln Asp Asn Lys
            180                 185                 190

Ile Ser Asn Leu Thr Ala Gln Gln Gln Glu Ala Gln Lys Gln Val Asp
        195                 200                 205

Gln Ile Gln Glu Gln Val Ser Ala Ile Gln Ala Glu Gln Ser Asn Leu
    210                 215                 220

Gln Ala Glu Asn Asp Arg Leu Gln Ala Glu Ser Lys Lys Leu Glu Gly
225                 230                 235                 240

Glu Ile Thr Glu Leu Ser Lys Asn Ile Val Ser Arg Asn Gln Ser Leu
                245                 250                 255

Glu Lys Gln Ala Arg Ser Ala Gln Thr Asn Gly Ala Val Thr Ser Tyr
            260                 265                 270

Ile Asn Thr Ile Val Asn Ser Lys Ser Ile Thr Glu Ala Ile Ser Arg
        275                 280                 285

Val Ala Ala Xaa Ser Glu Ile Val Ser Ala Asn Asn Lys Xaa Leu Glu
    290                 295                 300

Gln Gln Lys Ala Asp Lys Lys Ala Ile Ser Glu Lys Gln Val Ala Asn
305                 310                 315                 320

Asn Asp Ala Ile Asn Thr Val Ile Ala Asn Gln Gln Lys Leu Ala Asp
                325                 330                 335

Asp Ala Gln Ala Leu Thr Thr Lys Gln Ala Glu Leu Lys Ala Ala Glu
            340                 345                 350

Leu Ser Leu Ala Ala Glu Lys Ala Thr Ala Glu Gly Glu Lys Ala Ser
        355                 360                 365

Leu Leu Glu Gln Lys Ala Ala Ala Glu Ala Glu Ala Arg Ala Ala Ala
    370                 375                 380

Val Ala Glu Ala Ala Tyr Lys Glu Lys Arg Ala Ser Gln Gln Gln Ser
385                 390                 395                 400

Val Leu Ala Ser Ala Asn Thr Asn Leu Thr Ala Gln Val Gln Ala Val
                405                 410                 415

Ser Glu Ser Ala Ala Ala Pro Val Arg Ala Lys Val Arg Pro Thr Tyr
```

```
                420             425             430
Ser Thr Asn Ala Ser Ser Tyr Pro Ile Gly Glu Cys Thr Trp Gly Val
            435                 440                 445

Lys Thr Leu Ala Pro Trp Ala Gly Asp Tyr Trp Gly Asn Gly Ala Gln
            450                 455                 460

Trp Ala Thr Ser Ala Ala Ala Gly Phe Arg Thr Gly Ser Thr Pro
465                 470                 475                 480

Gln Val Gly Ala Ile Ala Cys Trp Asn Asp Gly Gly Tyr Gly His Val
                    485                 490                 495

Ala Val Val Thr Ala Val Glu Ser Thr Thr Arg Ile Gln Val Ser Glu
                500                 505                 510

Ser Asn Tyr Ala Gly Asn Arg Thr Ile Gly Asn His Arg Gly Trp Phe
            515                 520                 525

Asn Pro Thr Thr Thr Ser Glu Gly Phe Val Thr Tyr Ile Tyr Ala Asp
            530                 535                 540

Ala Ala Ala Leu Glu His His His His His His
545                 550                 555

<210> SEQ ID NO 21
<211> LENGTH: 552
<212> TYPE: PRT
<213> ORGANISM: Streptococcus pneumoniae
<220> FEATURE:
<221> NAME/KEY: misc_feature
<222> LOCATION: 1, 115, 125
<223> OTHER INFORMATION: Xaa is L-homoallylglycine

<400> SEQUENCE: 21

Xaa Ala Glu Thr Thr Asp Asp Lys Ile Ala Ala Gln Asp Asn Lys Ile
1               5                   10                  15

Ser Asn Leu Thr Ala Gln Gln Gln Glu Ala Gln Lys Gln Val Asp Gln
            20                  25                  30

Ile Gln Glu Gln Val Ser Ala Ile Gln Ala Glu Gln Ser Asn Leu Gln
        35                  40                  45

Ala Glu Asn Asp Arg Leu Gln Ala Glu Ser Lys Lys Leu Glu Gly Glu
    50                  55                  60

Ile Thr Glu Leu Ser Lys Asn Ile Val Ser Arg Asn Gln Ser Leu Glu
65                  70                  75                  80

Lys Gln Ala Arg Ser Ala Gln Thr Asn Gly Ala Val Thr Ser Tyr Ile
                85                  90                  95

Asn Thr Ile Val Asn Ser Lys Ser Ile Thr Glu Ala Ile Ser Arg Val
            100                 105                 110

Ala Ala Xaa Ser Glu Ile Val Ser Ala Asn Asn Lys Xaa Leu Glu Gln
        115                 120                 125

Gln Lys Ala Asp Lys Lys Ala Ile Ser Glu Lys Gln Val Ala Asn Asn
    130                 135                 140

Asp Ala Ile Asn Thr Val Ile Ala Asn Gln Lys Leu Ala Asp Asp
145                 150                 155                 160

Ala Gln Ala Leu Thr Thr Lys Gln Ala Glu Leu Lys Ala Ala Glu Leu
                165                 170                 175

Ser Leu Ala Ala Glu Lys Ala Thr Ala Glu Gly Glu Lys Ala Ser Leu
            180                 185                 190

Leu Glu Gln Lys Ala Ala Ala Glu Ala Glu Ala Arg Ala Ala Ala Val
        195                 200                 205

Ala Glu Ala Ala Tyr Lys Glu Lys Arg Ala Ser Gln Gln Gln Ser Val
    210                 215                 220
```

```
Leu Ala Ser Ala Asn Thr Asn Leu Thr Ala Gln Val Gln Ala Val Ser
225                 230                 235                 240

Glu Ser Ala Ala Ala Pro Val Arg Ala Lys Val Arg Pro Thr Tyr Ser
                245                 250                 255

Thr Asn Ala Ser Ser Tyr Pro Ile Gly Glu Cys Thr Trp Gly Val Lys
            260                 265                 270

Thr Leu Ala Pro Trp Ala Gly Asp Tyr Trp Gly Asn Gly Ala Gln Trp
        275                 280                 285

Ala Thr Ser Ala Ala Ala Gly Phe Arg Thr Gly Ser Thr Pro Gln
    290                 295                 300

Val Gly Ala Ile Ala Cys Trp Asn Asp Gly Gly Tyr Gly His Val Ala
305                 310                 315                 320

Val Val Thr Ala Val Glu Ser Thr Thr Arg Ile Gln Val Ser Glu Ser
                325                 330                 335

Asn Tyr Ala Gly Asn Arg Thr Ile Gly Asn His Arg Gly Trp Phe Asn
            340                 345                 350

Pro Thr Thr Thr Ser Glu Gly Phe Val Thr Tyr Ile Tyr Ala Asp Gly
        355                 360                 365

Ser Gly Ser Gly Gly Gly Val Ser Ala Gln Glu Ser Ser Thr Tyr
    370                 375                 380

Thr Val Lys Glu Gly Asp Thr Leu Ser Glu Ile Ala Glu Thr His Asn
385                 390                 395                 400

Thr Thr Val Glu Lys Leu Ala Glu Asn Asn His Ile Asp Asn Ile His
                405                 410                 415

Leu Ile Tyr Val Asp Gln Glu Leu Val Ile Asp Gly Pro Val Ala Pro
            420                 425                 430

Val Ala Thr Pro Ala Pro Ala Thr Tyr Ala Ala Pro Ala Ala Gln Asp
        435                 440                 445

Glu Thr Val Ser Ala Pro Val Ala Glu Thr Pro Val Val Ser Glu Thr
    450                 455                 460

Val Val Ser Thr Val Ser Gly Ser Glu Ala Glu Ala Lys Glu Trp Ile
465                 470                 475                 480

Ala Gln Lys Glu Ser Gly Gly Ser Tyr Thr Ala Thr Asn Gly Arg Tyr
                485                 490                 495

Ile Gly Arg Tyr Gln Leu Thr Asp Ser Tyr Leu Asn Gly Asp Tyr Ser
            500                 505                 510

Ala Glu Asn Gln Glu Arg Val Ala Asp Ala Tyr Val Ala Gly Arg Tyr
        515                 520                 525

Gly Ser Trp Thr Ala Ala Lys Asn Phe Trp Leu Asn Asn Gly Trp Tyr
    530                 535                 540

Leu Glu His His His His His His
545                 550
```

CONJUGATES COMPRISING AN ANTIGEN AND A CARRIER MOLECULE

This application claims the benefit of U.S. Provisional Application No. 61/556,456, filed on Nov. 7, 2011; and U.S. Provisional Application No. 61/566,407, filed on Dec. 2, 2011. The teachings of the above applications are incorporated by reference herein in their entirety.

TECHNICAL FIELD

The invention relates to conjugates of antigens and carrier molecules, and vaccines comprising these conjugates. The antigens are typically saccharides.

SEQUENCE LISTING

The instant application contains a Sequence Listing which has been submitted via EFS-Web and is hereby incorporated by reference in its entirety. The ASCII copy, created on Mar. 20, 2013, is named PAT54803_Substitute_ASCII.TXT, and is 55,216 bytes in size.

BACKGROUND OF THE INVENTION

The use of conjugation to carrier proteins in order to enhance the immunogenicity of saccharide antigens is well known [e.g. reviewed in refs. 1 to 9 etc.] and is used in particular for pediatric vaccines [10]. Three widely used carrier proteins in present-day vaccines are tetanus toxoid (TT), diphtheria toxoid (DT) and the diphtheria toxoid variant, CRM197. These proteins have been used as carriers for various saccharides, particularly meningococcal capsular saccharides (see, for example, the use of TT as carrier for saccharides derived from N. meningitidis serogroups A, C, W135 and Y in ref. 11; and DT and CRM197 as carriers for the same saccharides in refs. 12 and 13 respectively). Concerns have been raised about the overuse of these carrier proteins in vaccines [see, for example, ref. 14], with various alternative carriers being suggested (e.g. protein D from H. influenzae in ref. 15). However, many alternative carrier proteins are not as effective as TT, DT and/or CRM197. Accordingly, there remains a need to find alternative and/or better carrier proteins.

It is therefore an object of the invention to provide further and better carrier proteins, particularly carrier proteins for meningococcal capsular saccharides. The carrier proteins may be used in conjugates to induce protective and/or therapeutic immune responses against infections or drugs.

SUMMARY OF THE INVENTION

The inventors have found that proteins comprising two specific Streptococcus pneumoniae antigens, a spr0096 antigen and a spr2021 antigen, are effective carriers. These carriers are versatile and may be conjugated to various antigens, particularly saccharides e.g. from pathogenic organisms. The resultant conjugates may be more immunogenic than conjugates based on currently used carrier proteins, e.g. CRM197. Moreover, they may provide higher levels of protective immunity against pathogens from which the saccharides are derived.

The invention therefore provides a conjugate comprising an antigen and a carrier molecule, wherein the carrier molecule comprises a spr0096 antigen and a spr2021 antigen. The carrier molecule typically comprises the spr0096 antigen and the spr2021 antigen as a single polypeptide chain (a "hybrid" polypeptide). Typically, the antigen is a saccharide. The saccharide may be any saccharide, particularly a saccharide from a pathogenic organism. For example, the saccharide may be a capsular saccharide from N. meningitidis, a glucan or a capsular saccharide from S. pneumoniae. When the saccharide is a capsular saccharide from N. meningitidis, it is typically from one of the following meningococcal serogroups: A, C, W135 and Y. When the saccharide is a glucan, it is typically a laminarin. When the saccharide is a capsular saccharide from S. pneumoniae, it is typically from one of the following pneumococcal serotypes: 1, 2, 3, 4, 5, 6A, 6B, 7F, 8, 9N, 9V, 10A, 11A, 12F, 14, 15B, 17F, 18C, 19A, 19F, 20, 22F, 23F and 33F. However, in some embodiments, the saccharide is not a capsular saccharide from S. pneumoniae.

The present invention also relates to pharmaceutical compositions comprising a conjugate of the invention in combination with a pharmaceutically acceptable carrier.

The present invention further relates to methods for raising an immune response in a mammal, comprising administering a conjugate or pharmaceutical composition of the invention to the mammal.

The present invention further relates to carrier molecules which have been modified to include non-natural amino acids.

BRIEF DESCRIPTION OF DRAWINGS

FIG. 1A provides the first half of a table of the repeating units of representative bacterial saccharides for use in the invention.

FIG. 1B provides the second half of a table of the repeating units of representative bacterial saccharides for use in the invention.

FIG. 6B compares the effects of a pneumococcal conjugate of the invention with a reference CRM197 conjugate in a model of protective immunity against pneumococcus serotype 5 infection.

FIG. 7B compares the effects of a pneumococcal conjugate of the invention, a reference CRM197 conjugate, and the pneumococcal saccharide and carrier alone and together, in a model of protective immunity against pneumococcus serotype 5 infection.

FIG. 18C compares the immunogenicity of the other meningococcal conjugates in the study of FIG. 17.

DETAILED DESCRIPTION OF THE INVENTION

Figure 2:
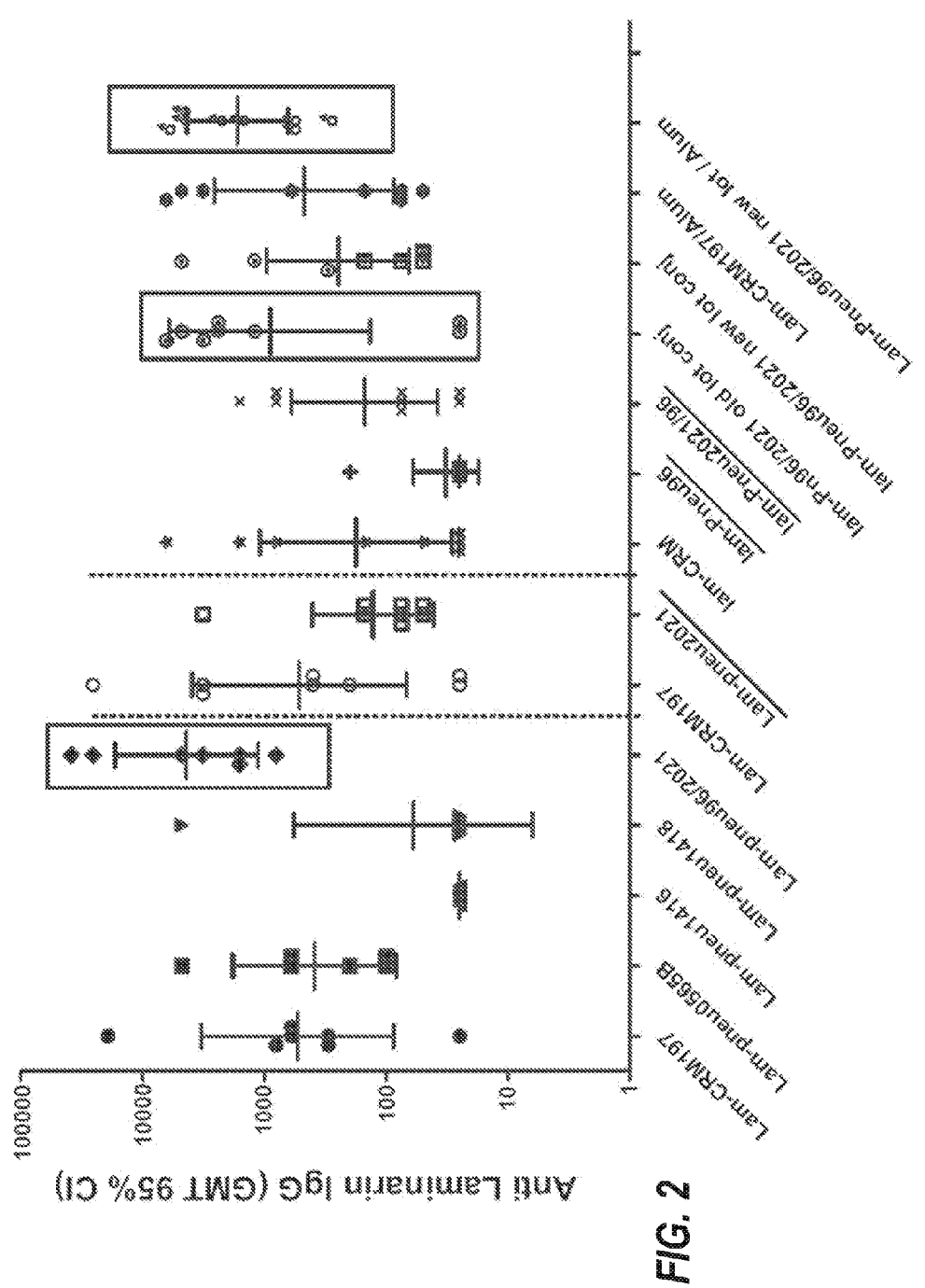
FIG. 2 compares the immunogenicity of laminarin conjugated to various pneumococcal proteins and a reference carrier, CRM197.

The invention involves a conjugate comprising an antigen and a carrier molecule, wherein the carrier molecule comprises a spr0096 antigen and a spr2021 antigen. The features of this conjugate are described in detail below.

The invention also involves carrier molecules which have been modified to incorporate non-natural amino acids. Exemplary modifications and carrier proteins are also described in detail below.

The Carrier Molecule

The carrier molecule comprises a spr0096 antigen and a spr2021 antigen. Typically, the carrier molecule comprises the spr0096 antigen and the spr2021 antigen as a single polypeptide chain (a "hybrid" polypeptide).

spr0096 Antigen

The original 'spr0096' polypeptide sequence was annotated in reference 16 as 'hypothetical protein' (see GI:15902140). For reference purposes, the amino acid sequence of full length spr0096 as found in the R6 strain is given as SEQ ID NO: 1 herein.

The spr0096 antigen of the invention comprises at least one CD4$^+$ T cell epitope. CD4$^+$ T cells help B lymphocytes to produce antibodies against antigens [17]. T-cell epitopes can be identified empirically (e.g. using PEPSCAN [18,19] or similar methods), or they can be predicted (e.g. using the Jameson-Wolf antigenic index [20], matrix-based approaches [21], TEPITOPE [22], neural networks [23], OptiMer & EpiMer [24,25], ADEPT [26], Tsites [27], hydrophilicity [28], antigenic index [29] or the methods disclosed in reference 30, etc.).

Preferred spr0096 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 1; and/or (b) comprising a fragment of at least 'n' consecutive amino acids of SEQ ID NO: 1, wherein 'n' is 7 or more (e.g. 8, 10, 12, 14, 16, 18, 20, 25, 30, 35, 40, 50, 60, 70, 80, 90, 100, 150, 200, 250 or more). These spr0096 polypeptides include variants of SEQ ID NO: 1 (e.g. SEQ ID NO: 2; see below). Preferred fragments of (b) comprise at least one CD4$^+$ T cell epitope from SEQ ID NO: 1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 1 while retaining at least one CD4$^+$ T cell epitope of SEQ ID NO: 1. Other fragments omit one or more protein domains. One suitable fragment is SEQ ID NO: 14, which omits the natural leader peptide sequence. The spr0096 antigen may consist of a single CD4$^+$ T cell epitope from SEQ ID NO: 1.

A variant form of spr0096, with an insert near its C-terminus relative to SEQ ID NO: 1, is SEQ ID NO: 2 herein. The use of this variant for immunisation is reported in reference 31 (SEQ ID NO: 150 therein), where it is annotated as a LysM domain protein. Thus a spr0096 antigen for use with the invention may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 2; and/or (b) comprising a fragment of at least 'n' consecutive amino acids of SEQ ID NO: 2, wherein 'n' is 7 or more (e.g. 8, 10, 12, 14, 16, 18, 20, 25, 30, 35, 40, 50, 60, 70, 80, 90, 100, 150, 200, 250 or more). These polypeptides include variants of SEQ ID NO: 2. Preferred fragments of (b) comprise at least one CD4$^+$ T cell epitope from SEQ ID NO: 2. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 2 while retaining at least one CD4$^+$ T cell epitope of SEQ ID NO: 2. Other fragments omit one or more protein domains. One suitable fragment is SEQ ID NO: 15, which omits the natural leader peptide sequence. Immunogenic fragments of SEQ ID NO: 2 are identified in table 1 of reference 31. The spr0096 antigen may consist of a single CD4$^+$ T cell epitope from SEQ ID NO: 2.

A spr0096 antigen may be used in the form of a dimer e.g. a homodimer.

spr2021 Antigen

The original 'spr2021' polypeptide sequence was annotated in reference 16 as 'General stress protein GSP-781' (see GI:15904062). For reference purposes, the amino acid sequence of full length spr2021 as found in the R6 strain is given as SEQ ID NO: 3 herein.

The spr2021 antigen of the invention comprises at least one CD4+ T cell epitope.

Preferred spr2021 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 3; and/or (b) comprising a fragment of at least 'n' consecutive amino acids of SEQ ID NO: 3, wherein 'n' is 7 or more (e.g. 8, 10, 12, 14, 16, 18, 20, 25, 30, 35, 40, 50, 60, 70, 80, 90, 100, 150, 200, 250 or more). These spr2021 polypeptides include variants of SEQ ID NO: 3. Preferred fragments of (b) comprise at least one CD4+ T cell epitope from SEQ ID NO: 3. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 3 while retaining at least one CD4+ T cell epitope of SEQ ID NO: 3. Other fragments omit one or more protein domains. One suitable fragment is SEQ ID NO: 4, which omits the natural leader peptide sequence. The spr0096 antigen may consist of a single CD4+ T cell epitope from SEQ ID NO: 3.

Reference 31 annotates spr2021 as a secreted 45 kDa protein with homology to GbpB and discloses its use as an immunogen (SEQ ID NO: 243 therein; SP2216). Immunogenic fragments of spr2021 are identified in table 1 of reference 31 (page 73). Another useful fragment of spr2021 is disclosed as SEQ ID NO: 1 of reference 32 (amino acids 28-278 of SEQ ID NO: 3 herein).

Hybrid Polypeptide

Typically, the spr0096 antigen and spr2021 antigen are expressed as a single polypeptide chain (a 'hybrid' polypeptide). Hybrid polypeptides can be represented by the formula $NH_2$-A-{-X-L-}$_n$-B—COOH, wherein: A is an optional N-terminal amino acid sequence; B is an optional C-terminal amino acid sequence; n is an integer of 2 or more (e.g. 2, 3, 4, 5, 6, etc.); each X is an amino acid sequence of an spr0096 antigen or an spr2021 antigen (as described above), wherein at least one X is an spr0096 antigen and at least one X is an spr2021 antigen; and L is an optional linker amino acid sequence. Usually n is 2. When n is 2, $X_1$ is usually an spr0096 antigen and $X_2$ is usually an spr2021 antigen. When n is more than 2, each spr0096 antigen (when more than one is present) may be the same or different and each spr2021 antigen (when more than one is present) may be the same or different.

The spr0096 antigen or spr2021 antigen that is the amino acid sequence of each X is as defined above. Where these antigens are defined in terms of (a) having 50% or more identity (e.g. 60%, 65%, 70%, 75%, 80%, 85%, 90%, 91%, 92%, 93%, 94%, 95%, 96%, 97%, 98%, 99%, 99.5% or more) to a given sequence; and/or (b) comprising a fragment of at least 'n' consecutive amino acids of a given sequence, wherein 'n' is 7 or more (e.g. 8, 10, 12, 14, 16, 18, 20, 25, 30, 35, 40, 50, 60, 70, 80, 90, 100, 150, 200, 250 or more), the level of identity in (a) and the value of 'n' in (b) may be the same for each X.

The leader peptide sequence in the wild-type form of each —X— moiety may be included or omitted in the hybrid protein. In some embodiments, the leader peptides will be deleted except for that of the —X-moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of {—X-L-}, linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s)-L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising Gly$_n$ where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. A useful linker is GSGGGG (SEQ ID NO:5) or GSGSGGGG (SEQ ID NO:6), with the Gly-Ser dipeptide being formed from a BamHI restriction site, thus aiding cloning and manipulation, and the (Gly)$_4$ tetrapeptide being a typical poly-glycine linker. Other suitable linkers, particularly for use as the final $L_n$ are a Leu-Glu dipeptide or SEQ ID NO: 7.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His$_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine e.g. Met-Ala-Ser, or a single Met residue.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. His$_n$ where n=3, 4, 5, 6, 7, 8, 9, 10 or more, such as SEQ ID NO: 8), or sequences which enhance protein stability. Other suitable C-terminal amino acid sequences will be apparent to those skilled in the art.

Examples of hybrids include polypeptides that comprise an amino acid sequence of spr0096-spr2021 (e.g. SEQ ID NO: 9) or spr2021-spr0096 (e.g. SEQ ID NO: 10). The hybrid may also comprise an amino acid sequence having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9 or 10. Typically, the hybrid comprises an amino acid sequence of SEQ ID NO: 9. The hybrid may also comprise an amino acid sequence having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9.

In particular embodiments, the carrier molecule comprises (a) one or more (e.g. 1, 2, 3, 4, 5, etc.) CD4+ T cell epitopes from SEQ ID NO: 2; and (b) one or more (e.g. 1, 2, 3, 4, 5, etc.) CD4+ T cell epitopes from SEQ ID NO: 3.

Carrier Molecules Modified to Incorporate Non-Natural Amino Acids

The invention also involves carrier molecules which have been modified to incorporate non-natural amino acids. The non-natural amino acid may be used to conjugate the carrier molecule to another molecule.

In some alternatives, the carrier molecule comprises one or more (e.g. 1, 2, 3, 4, 5, 6, 7, 8, 9, 10 etc.) non-natural amino acids. The non-natural amino acid may have a functional group with a reaction profile that is different to the functional groups available to react in proteins composed of the canonical amino acids (e.g. the amino group of lysine or the sulhydryl group of cysteine). This in turn means that chemoselective reactions allow site-selective conjugations to be performed at pre-determined sites where a non-natural amino acid has been incorporated into the protein.

In particular embodiments, the carrier molecule comprises one or more L-homoallylglycine (HAG) residues. Typically HAG residues are substituted in place of the methionine residues in the sequence. HAG, chemically known as L-2-amino-5-hexenoic acid, is an analogue of methionine, and contains a reactive alkene site. HAG can substitute for methionine in both the initiation and elongation steps of protein synthesis. HAG has an olefinic sidechain which has a different reaction profile to the functional groups found in canonical amino acids, reacting through a thiyl-ene mechanism.

In other embodiments, the carrier molecule may be modified to include other non-natural amino acids which permit site-selective conjugations to be performed at pre-determined sites. For example, the carrier molecule may be modified so that one or more (e.g. 1, 2, 3, 4, 5, etc.) p-acetylphenylalanine residues are included in its sequence. This amino acid has a keto functional group, which is not present in any of the canonical amino acids, and therefore the amino acid can be reacted specifically with hydrazines, alkoxyamines and semicarbazides under mild aqueous conditions to produce hydrazone, oxime and semicarbazone linkages. Other amino acids with keto functional groups include m-acetylphenylalanine and p-benzoylphenylalanine and these residues may be used in the same manner.

In other embodiments, the carrier molecule may be modified to include an azide group (which also does not occur in the canonical amino acids), for example by incorporation of one or more (e.g. 1, 2, 3, 4, 5, etc.) p-azidophenylalanine residues. The azide group can react with an acetylene group on the conjugation partner through a copper (I) catalysed [2+3] cycloaddition reaction. Conversely, it is possible to engineer the non-naturally occurring acetylene group into the carrier protein by incorporation of one or more (e.g. 1, 2, 3, 4, 5, etc.) p-propargyloxyphenylalanine residues, which can then be reacted through the same mechanism with an azide group on the conjugation partner.

In yet further embodiments, the carrier molecule may be modified to include one or more (e.g. 1, 2, 3, 4, 5, etc.) phenylselenocysteine residues. Treatment of this residue with hydrogen peroxide allows its conjugation to thiol groups.

In exemplary modified carrier molecules of the invention, the spr0096 antigen may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 1; and/or (b) comprising a fragment of at least 'n' consecutive amino acids of SEQ ID NO: 1, wherein 'n' is 7 or more (e.g. 8, 10, 12, 14, 16, 18, 20, 25, 30, 35, 40, 50, 60, 70, 80, 90, 100, 150, 200, 250 or more), wherein one or more of the methionine residues in the polypeptide is replaced with HAG. For example, the carrier molecule may have the sequence set out in SEQ ID NO: 16.

A variant form of spr0096, with an insert near its C-terminus relative to SEQ ID NO: 1, is SEQ ID NO: 2 herein. Thus a spr0096 antigen for use with the invention may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 2; and/or (b) comprising a fragment of at least 'n' consecutive amino acids of SEQ ID NO: 2, wherein 'n' is 7 or more (e.g. 8, 10, 12, 14, 16, 18, 20, 25, 30, 35, 40, 50, 60, 70, 80, 90, 100, 150, 200, 250 or more), wherein one or more of the methionine residues in the polypeptide is replaced with HAG. For example, the carrier molecule may have the sequence set out in SEQ ID NO: 17.

In other or the same examples of modified carrier molecules of the invention, the spr2021 antigen may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 3; and/or (b) comprising a fragment of at least 'n' consecutive amino acids of SEQ ID NO: 3, wherein 'n' is 7 or more (e.g. 8, 10, 12, 14, 16, 18, 20, 25, 30, 35, 40, 50, 60, 70, 80, 90, 100, 150, 200, 250 or more)), wherein one or more of the methionine residues in the polypeptide is replaced with HAG. In some embodiments two or more, three or more, or four or more of the methionine residues in the polypeptide are replaced with HAG. For example, the carrier molecule may have the sequence set out in SEQ ID NO: 18.

A variant form of spr2021 is SEQ ID NO: 4, which omits the natural leader peptide sequence. Thus a spr2021 antigen for use with the invention may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 4; and/or (b) comprising a fragment of at least 'n' consecutive amino acids of SEQ ID NO: 4, wherein 'n' is 7 or more (e.g. 8, 10, 12, 14, 16, 18, 20, 25, 30, 35, 40, 50, 60, 70, 80, 90, 100, 150, 200, 250 or more), wherein one or more of the methionine residues in the polypeptide is replaced with HAG. For example, the carrier molecule may have the sequence set out in SEQ ID NO: 19.

Further examples of modified carrier molecules include hybrid polypeptides as defined above, wherein one or more of the methionine residues in the polypeptide is replaced with HAG. For example, the hybrid polypeptide may comprise an amino acid sequence of spr0096-spr2021 (e.g. SEQ ID NO: 9) or spr2021-spr0096 (e.g. SEQ ID NO: 10), or an amino acid sequence having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9 or 10, wherein one or more of the methionine residues in the polypeptide is replaced with HAG. In some embodiments two or more, or three or more of the methionine residues in the polypeptide are replaced with HAG. For example, the carrier molecule may have the sequence set out in SEQ ID NO: 20 or 21. In particular embodiments, the carrier molecule comprises (a) one or more (e.g. 1, 2, 3, 4, 5, etc.) CD4$^+$ T cell epitopes from SEQ ID NO: 2; and/or (b) one or more (e.g. 1, 2, 3, 4, 5, etc.) CD4$^+$ T cell epitopes from SEQ ID NO: 3.

These techniques can also be applied to other known non-natural amino acids, and further to other carrier molecules. Accordingly in the above embodiments, the carrier molecule may be any one of these other carrier molecules. Preferred carrier molecules include bacterial toxins, such as diphtheria or tetanus toxins, or toxoids or mutants thereof. These are commonly used in conjugate vaccines. The CRM$_{197}$ diphtheria toxin mutant is particularly preferred [33]. Fragment C of tetanus toxoid may also be used [34]. Other carrier molecules include antigens, such as spr0096 or spr2021 as described above. Further suitable carrier molecules include the N. meningitidis outer membrane protein complex [35], synthetic peptides [36,37], heat shock proteins [38,39], pertussis proteins [40,41], cytokines [42], lymphokines [150], hormones [150], growth factors [150], artificial proteins comprising multiple human CD4+ T cell epitopes from various pathogen-derived antigens [43] such as N19 [44], protein D from *H. influenzae* [45-47], pneumolysin [48] or its non-toxic derivatives [49], pneumococcal surface protein PspA [50], iron-uptake proteins [51], toxin A or B from *C. difficile* [52], recombinant *Pseudomonas aeruginosa* exoprotein A (rEPA) [53], etc.

The Antigen

The antigen is typically a saccharide. When the antigen is a saccharide, the saccharide may be any saccharide, particularly a saccharide from a pathogenic organism. Exemplary saccharides for use in the invention are described below. In particular, the saccharide may be a bacterial saccharide, e.g. a bacterial capsular saccharide. Representative bacterial saccharides are described in FIG. 1A and FIG. 1B.

The saccharides may be used in the form of oligosaccharides. These are conveniently formed by fragmentation of purified polysaccharide (e.g. by hydrolysis), which will usually be followed by purification of the fragments of the desired size. Saccharides may be purified from natural sources. As an alternative to purification, saccharides may be obtained by total or partial synthesis.

When the antigen is not a saccharide, it may be any other antigen, i.e. any immunogen or hapten. Conjugates of the invention may elicit an immune response against a hapten conjugated to the carrier molecule. The hapten may for example be a drug of abuse [54]. Examples include, but are not limited to, opiates, marijuana, amphetamines, cocaine, barbituates, glutethimide, methyprylon, chloral hydrate, methaqualone, benzodiazepines, LSD, nicotine, anticholinergic drugs, antipsychotic drugs, tryptamine, other psychomimetic drugs, sedatives, phencyclidine, psilocybine, volatile nitrite, and other drugs inducing physical and/or psychological dependence.

N. Meningitidis Capsular Saccharides

The saccharide may be a bacterial capsular saccharide. Exemplary bacterial capsular saccharides include those from *N. meningitidis*. Based on the organism's capsular polysaccharide, various serogroups of *N. meningitidis* have been identified, including A, B, C, H, I, K, L, 29E, W135, X, Y & Z. The saccharide in the invention may be from any of these serogroups. Typically, the saccharide is from one of the following meningococcal serogroups: A, C, W135 and Y.

The capsular saccharides will generally be used in the form of oligosaccharides. These are conveniently formed by fragmentation of purified capsular polysaccharide (e.g. by hydrolysis), which will usually be followed by purification of the fragments of the desired size.

Fragmentation of polysaccharides is typically performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [55].

If hydrolysis is performed, the hydrolysate will generally be sized in order to remove short-length oligosaccharides [56]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Chemical hydrolysis of saccharides generally involves treatment with either acid or base under conditions that are standard in the art. Conditions for depolymerisation of capsular saccharides to their constituent monosaccharides are known in the art. One depolymerisation method involves the use of hydrogen peroxide [57]. Hydrogen peroxide is added to a saccharide (e.g. to give a final $H_2O_2$ concentration of 1%), and the mixture is then incubated (e.g. at around 55° C.) until a desired chain length reduction has been achieved. The reduction over time can be followed by removing samples from the mixture and then measuring the (average) molecular size of saccharide in the sample. Depolymerization can then be stopped by rapid cooling once a desired chain length has been reached Serogroups C, W135 and Y Techniques for preparing capsular polysaccharides from meningococci have been known for many years, and typically involve a process comprising the steps of polysaccharide precipitation (e.g. using a cationic detergent), ethanol fractionation, cold phenol extraction (to remove protein) and ultracentrifugation (to remove LPS) [e.g. see ref. 58].

A more preferred process [59] involves polysaccharide precipitation followed by solubilisation of the precipitated polysaccharide using a lower alcohol. Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is particularly preferred [60]. Solubilisation of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilising CTAB-polysaccharide complexes. Ethanol may be added to the precipitated polysaccharide to give a final ethanol concentration (based on total content of ethanol and water) of between 50% and 95%.

After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration.

Once filtered to remove contaminants, the polysaccharide may be precipitated for further treatment and/or processing. This can be conveniently achieved by exchanging cations (e.g. by the addition of calcium or sodium salts).

After purification, the capsular saccharides are conjugated to carrier proteins as described below.

Further and alternative methods for purification and conjugation of meningococcal saccharides are disclosed in references 57 & 61.

As an alternative to purification, capsular saccharides of the present invention may be obtained by total or partial synthesis e.g. Hib synthesis is disclosed in ref. 62, and MenA synthesis in ref. 63.

The saccharide may be chemically modified e.g. it may be O-acetylated or de-O-acetylated. Any such de-O-acetylation or hyper-acetylation may be at specific positions in the saccharide. For instance, most serogroup C strains have O-acetyl groups at position C-7 and/or C-8 of the sialic acid residues, but about 15% of clinical isolates lack these O-acetyl groups [64,65]. The acetylation does not seem to affect protective efficacy (e.g. unlike the Menjugate™ product, the NeisVac-C™ product uses a de-O-acetylated saccharide, but both vaccines are effective). The serogroup W135 saccharide is a polymer of sialic acid-galactose disaccharide units. The serogroup Y saccharide is similar to the serogroup W135 saccharide, except that the disaccharide repeating unit includes glucose instead of galactose. Like the serogroup C saccharides, the MenW135 and MenY saccharides have variable O-acetylation, but at sialic acid 7 and 9 positions [66]. Any such chemical modifications preferably take place before conjugation, but may alternatively or additionally take place during conjugation.

Saccharides from different serogroups are preferably purified separately, and may then be combined, either before or after conjugation.

Serogroup A

Conjugates of the invention may include a serogroup A capsular saccharide antigen. The saccharide can be purified and conjugated in the same way as for serogroups C, W135 and Y (see above), although it is structurally different—whereas the capsules of serogroups C, W135 and Y are based around sialic acid (N-acetyl-neuraminic acid, NeuAc), the capsule of serogroup A is based on N-acetyl-mannosamine, which is the natural precursor of sialic acid. The serogroup A saccharide is particularly susceptible to hydrolysis, and its instability in aqueous media means that (a) the immunogenicity of liquid vaccines against serogroup A declines over time, and (b) quality control is more difficult, due to release of saccharide hydrolysis products into the vaccine.

Native MenA capsular saccharide is a homopolymer of (α1→6)-linked N-acetyl-D-mannosamine-1-phosphate, with partial O-acetylation at C3 and C4. The principal glycosidic bond is a 1-6 phosphodiester bond involving the hemiacetal group of C1 and the alcohol group of C6 of the D-mannosamine. The average chain length is 93 monomers. It has the following formula:

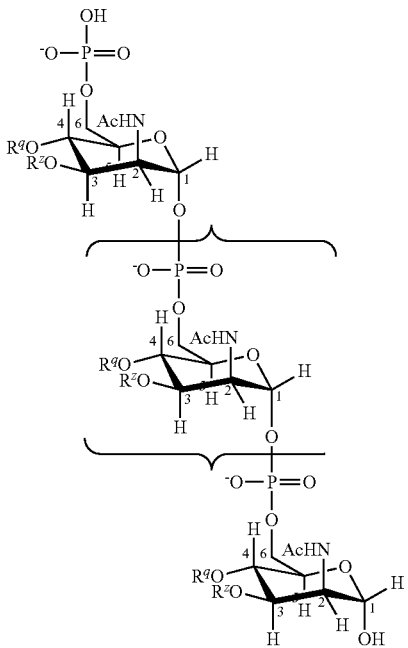

$R^z = Ac$  
$R^q = H$  } 70%

$R^z = H$  
$R^q = H$  } 23%

$R^z = H$  
$R^q = Ac$  } 7%

A modified saccharide antigen has been prepared which retains the immunogenic activity of the native serogroup A saccharide but which is much more stable in water. Hydroxyl groups attached at carbons 3 and 4 of the monosaccharide units are replaced by a blocking group [refs. 67 and 68].

The number of monosaccharide units having blocking groups in place of hydroxyls can vary. For example, all or substantially all the monosaccharide units may have blocking groups. Alternatively, at least 10%, 20%, 30%, 40%, 50%, 60%, 70%, 80% or 90% of the monosaccharide units may have blocking groups. At least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 monosaccharide units may have blocking groups.

Likewise, the number of blocking groups on a monosaccharide unit may vary. For example, the number of blocking groups on any particular monosaccharide unit may be 1 or 2.

The terminal monosaccharide unit may or may not have a blocking group instead of its native hydroxyl. It is preferred to retain a free anomeric hydroxyl group on a terminal monosaccharide unit in order to provide a handle for further reactions (e.g. conjugation). Anomeric hydroxyl groups can be converted to amino groups (—$NH_2$ or —NH-E, where E is a nitrogen protecting group) by reductive amination (using, for example, $NaBH_3CN/NH_4Cl$), and can then be regenerated after other hydroxyl groups have been converted to blocking groups.

Blocking groups to replace hydroxyl groups may be directly accessible via a derivatizing reaction of the hydroxyl group i.e. by replacing the hydrogen atom of the hydroxyl group with another group. Suitable derivatives of hydroxyl groups which act as blocking groups are, for example, carbamates, sulfonates, carbonates, esters, ethers (e.g. silyl ethers or alkyl ethers) and acetals. Some specific examples of such blocking groups are allyl, Aloc, benzyl, BOM, t-butyl, trityl, TBS, TBDPS, TES, TMS, TIPS, PMB, MEM, MOM, MTM, THP, etc. Other blocking groups that are not directly accessible and which completely replace the hydroxyl group include $C_{1-12}$ alkyl, $C_{3-12}$ alkyl, $C_{5-12}$ aryl, $C_{5-12}$ aryl-$C_{1-6}$ alkyl, $NR^1R^2$ ($R^1$ and $R^2$ are defined in the following paragraph), H, F, Cl, Br, $CO_2H$, $CO_2(C_{1-6}$ alkyl), CN, $CF_3$, $CCl_3$, etc.

Typical blocking groups are of the formula: —O—X—Y or —$OR^3$ wherein: X is C(O), S(O) or $SO_2$; Y is $C_{1-12}$ alkyl, $C_{1-12}$ alkoxy, $C_{3-12}$ cycloalkyl, $C_{5-12}$ aryl or $C_{5-12}$ aryl-$C_{1-6}$ alkyl, each of which may optionally be substituted with 1, 2 or 3 groups independently selected from F, Cl, Br, $CO_2H$, $CO_2(C_{1-6}$ alkyl), CN, $CF_3$ or $CCl_3$; or Y is $NR^1R^2$; $R^1$ and $R^2$ are independently selected from H, $C_{1-12}$ alkyl, $C_{3-12}$ cycloalkyl, $C_{5-12}$ aryl, $C_{5-12}$ aryl-$C_{1-6}$ alkyl; or $R^1$ and $R^2$ may be joined to form a $C_{3-12}$ saturated heterocyclic group; $R^3$ is $C_{1-12}$ alkyl or $C_{3-12}$ cycloalkyl, each of which may optionally be substituted with 1, 2 or 3 groups independently selected from F, Cl, Br, $CO_2(C_{1-6}$ alkyl), CN, $CF_3$ or $CCl_3$; or $R^3$ is $C_{5-12}$ aryl or $C_{5-12}$ aryl-$C_{1-6}$ alkyl, each of which may optionally be substituted with 1, 2, 3, 4 or 5 groups selected from F, Cl, Br, $CO_2H$, $CO_2(C_{1-6}$ alkyl), CN, $CF_3$ or $CCl_3$. When $R^3$ is $C_{1-12}$ alkyl or $C_{3-12}$ cycloalkyl, it is typically substituted with 1, 2 or 3 groups as defined above. When $R^1$ and $R^2$ are joined to form a $C_{3-12}$ saturated heterocyclic group, it is meant that $R^1$ and $R^2$ together with the nitrogen atom form a saturated heterocyclic group containing any number of carbon atoms between 3 and 12 (e.g. $C_3$, $C_4$, $C_5$, $C_6$, $C_7$, $C_8$, $C_9$, $C_{10}$, $C_{11}$, $C_{12}$). The heterocyclic group may contain 1 or 2 heteroatoms (such as N, O or S) other than the nitrogen atom. Examples of $C_{3-12}$ saturated heterocyclic groups are pyrrolidinyl, piperidinyl, morpholinyl, piperazinyl, imidazolidinyl, azetidinyl and aziridinyl.

Blocking groups —O—X—Y and —$OR^3$ can be prepared from —OH groups by standard derivatizing procedures, such as reaction of the hydroxyl group with an acyl halide, alkyl halide, sulfonyl halide, etc. Hence, the oxygen atom in —O—X—Y is usually the oxygen atom of the hydroxyl group, while the —X—Y group in —O—X—Y usually replaces the hydrogen atom of the hydroxyl group.

Alternatively, the blocking groups may be accessible via a substitution reaction, such as a Mitsonobu-type substitution. These and other methods of preparing blocking groups from hydroxyl groups are well known.

Specific blocking groups for use in the invention are —OC(O)$CF_3$ [69] and a carbamate group OC(O)$NR^1R^2$, where $R^1$ and $R^2$ are independently selected from $C_{1-6}$ alkyl. Typically, $R^1$ and $R^2$ are both methyl i.e. the blocking group is —OC(O)$NMe_2$. Carbamate blocking groups have a stabilizing effect on the glycosidic bond and may be prepared under mild conditions.

A particularly preferred blocking group is —OC(O)$CH_3$ [68]. The proportion of 4- and/or 3-positions in the modified *Neisseria meningitidis* serogroup A saccharide that have this blocking group may vary. For example, the proportion of 4-positions that have blocking groups may be about 0%, at least 10%, 20%, 30%, 40%, 50%, 60%, 70%, 80%, 90%, 95% or about 100%, with at least 80% and about 100% being preferred. Similarly, the proportion of 3-positions that have blocking groups may be about 0%, at least 10%, 20%, 30%, 40%, 50%, 60%, 70%, 80%, 90%, 95% or about 100%, with at least 80% and about 100% being preferred. Typically, the proportion of 4- and 3-positions that have blocking groups is about the same at each position. In other words, the ratio of 4-positions that have blocking groups to 3-positions that have blocking groups is about 1:1. However, in some embodiments, the proportion of 4-positions that have blocking groups may vary relative to the proportion of 3-positions that have blocking groups. For example, the ratio of 4-positions that have blocking groups to 3-positions that have blocking groups may be 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2. Similarly, the ratio of 3-positions that have blocking groups to 4-positions that have blocking groups may be 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2.

Typical modified MenA saccharides contain n monosaccharide units, where at least h % of the monosaccharide units do not have —OH groups at both of positions 3 and 4. The value of h is 24 or more (e.g. 25, 26, 27, 28, 29, 30, 35, 40, 45, 50, 55, 60, 65, 70, 75, 80, 85, 90, 95, 98, 99 or 100) and is usually 50 or more. The absent —OH groups are blocking groups as defined above.

Other typical modified MenA saccharides comprise monosaccharide units, wherein at least s of the monosaccharide units do not have —OH at the 3 position and do not have —OH at the 4 position. The value of s is at least 1 (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90). The absent —OH groups are blocking groups as defined above.

Suitable modified MenA saccharides for use with the invention have the formula:

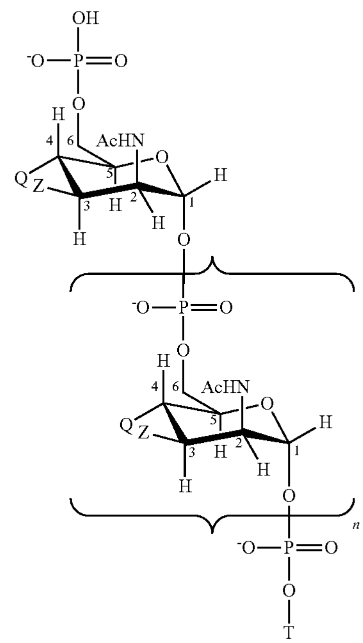

wherein n is an integer from 1 to 100 (particularly an integer from 5 to 25, usually 15-25);

T is of the formula (A) or (B):

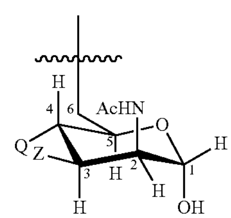

(A)

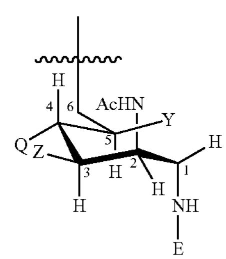

(B)

each Z group is independently selected from OH or a blocking group as defined above; and each Q group is independently selected from OH or a blocking group as defined above;

Y is selected from OH or a blocking group as defined above;

E is H or a nitrogen protecting group;

and wherein more than about 7% (e.g. 8%, 9%, 10% or more) of the Q groups are blocking groups. In some embodiments, the hydroxyl group attached at carbon 1 in formula (A) is replaced by a blocking group as defined above. In some embodiments, E in formula (B) is a linker or a carrier molecule of the invention. When E is a linker, the linker may be covalently bonded to a carrier molecule of the invention.

Each of the n+2 Z groups may be the same or different from each other. Likewise, each of the n+2 Q groups may be the same or different from each other. All the Z groups may be OH. Alternatively, at least 10%, 20, 30%, 40%, 50% or 60% of the Z groups may be OAc. Typically, about 70% of the Z groups are OAc, with the remainder of the Z groups being OH or blocking groups as defined above. At least about 7% of Q groups are blocking groups. Typically, at least 10%, 20%, 30%, 40%, 50%, 60%, 70%, 80%, 90% or even 100% of the Q groups are blocking groups.

Glucans

The saccharide may be a glucan. Glucans are glucose-containing polysaccharides found inter alia in fungal cell walls. The α-glucans include one or more α-linkages between glucose subunits, whereas β-glucans include one or more β-linkages between glucose subunits. The glucan used in accordance with the invention includes β linkages, and may contain only β linkages (i.e. no α linkages).

The glucan may comprise one or more β-1,3-linkages and/or one or more β-1,6-linkages. It may also comprise one or more β-1,2-linkages and/or β-1,4-linkages, but normally its only β linkages will be β-1,3-linkages and/or β-1,6-linkages.

The glucan may be branched or linear.

Full-length native β-glucans are insoluble and have a molecular weight in the megadalton range. It is preferred to use soluble glucans in conjugates of the invention. Solubilisation may be achieved by fragmenting long insoluble glucans. This may be achieved by hydrolysis or, more conveniently, by digestion with a glucanase (e.g. with a β-1,3-glucanase or a (β-1,6-glucanase). As an alternative, short glucans can be prepared synthetically by joining monosaccharide building blocks.

Low molecular weight glucans are preferred, particularly those with a molecular weight of less than 100 kDa (e.g. less than 80, 70, 60, 50, 40, 30, 25, 20, or 15 kDa). It is also possible to use oligosaccharides e.g. containing 60 or fewer (e.g. 59, 58, 57, 56, 55, 54, 53, 52, 51, 50, 49, 48, 47, 46, 45, 44, 43, 42, 41, 40 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4) glucose monosaccharide units. Within this range, oligosaccharides with between 10 and 50 or between 20 and 40 monosaccharide units are preferred.

The glucan may be a fungal glucan. A 'fungal glucan' will generally be obtained from a fungus but, where a particular glucan structure is found in both fungi and non-fungi (e.g. in bacteria, lower plants or algae) then the non-fungal organism may be used as an alternative source. Thus the glucan may be derived from the cell wall of a *Candida*, such as *C. albicans*, or from *Coccidioides immitis, Trichophyton verrucosum, Blastomyces dermatidis, Cryptococcus neoformans, Histoplasma capsulatum, Saccharomyces cerevisiae, Paracoccidioides brasiliensis*, or *Pythiumn insidiosum*.

There are various sources of fungal β-glucans. For instance, pure β-glucans are commercially available e.g. pustulan (Calbiochem) is a β-1,6-glucan purified from *Umbilicaria papullosa*. β-glucans can be purified from fungal cell walls in various ways. Reference 70, for instance, discloses a two-step procedure for preparing a water-soluble β-glucan extract from *Candida*, free from cell-wall mannan, involving NaClO oxidation and DMSO extraction. The resulting product ('*Candida* soluble β-D-glucan' or 'CSBG') is mainly composed of a linear β-1,3-glucan with a linear β-1,6-glucan moiety. Similarly, reference 71 discloses the production of GG-zym from *Calbicans*. Such glucans from *C. albicans*, include (a) β-1,6-glucans with β-1,3-glucan lateral chains and an average degree of polymerisation of about 30, and (b) β-1,3-glucans with β-1,6-glucan lateral chains and an average degree of polymerisation of about 4.

In some embodiments of the invention, the glucan is a β-1,3 glucan with some β-1,6 branching, as seen in e.g. laminarins. Laminarins are found in brown algae and seaweeds. The β(1-3):β(1-6) ratios of laminarins vary between different sources e.g. it is as low as 3:2 in *Eisenia bicyclis* laminarin, but as high as 7:1 in *Laminaria digititata* laminarin [72]. Thus the glucan used with the invention may have a β(1-3):β(1-6) ratio of between 1.5:1 and 7.5:1 e.g. about 2:1, 3:1, 4:1, 5:1, 6:1 or 7:1. Optionally, the glucan may have a terminal mannitol subunit, e.g. a 1,1-α-linked mannitol residue [73]. The glucan may also comprise mannose subunits.

In other embodiments, the glucan has exclusively or mainly β-1,3 linkages, as seen in curdlan. These glucans may elicit better protection than glucans comprising other linkages, particularly glucans comprising β-1,3 linkages and a greater proportion of β-1,6 linkages. Thus the glucan may be made solely of β-1,3-linked glucose residues (e.g. linear β-D-glucopyranoses with exclusively 1,3 linkages). Optionally, though, the glucan may include monosaccharide residues that are not β-1,3-linked glucose residues e.g. it may include β-1,6-linked glucose residues. The ratio of β-1,3-linked glucose residues to these other residues should be at least 8:1 (e.g. ≥9:1, ≥10:1, ≥11:1, ≥12:1, ≥13:1, ≥14:1, ≥15:1, ≥16:1, ≥17:1, ≥18:1, ≥19:1, ≥20:1, ≥25:1, ≥30:1, ≥35:1, ≥40:1, ≥45:1, ≥50:1, ≥75:1, ≥100:1, etc.) and/or there are one or more (e.g. ≥1, ≥2, ≥3, ≥4, ≥5, ≥6, ≥7, ≥8, ≥9, ≥10, ≥11, ≥12, etc.) sequences of at least five (e.g. ≥5, ≥6, ≥7, ≥8, ≥9, ≥10, ≥11, ≥12, ≥13, ≥14, ≥15, ≥16, ≥17, ≥18, ≥19, ≥20, ≥30, ≥40, ≥50, ≥60, etc.) adjacent non-terminal residues linked to other residues only by β-1,3 linkages. By "non-terminal" it is meant that the residue is not present at a free end of the glucan. In some embodiments, the adjacent non-terminal residues may not include any residues coupled to a carrier molecule, linker or other spacer as described below. The presence of five adjacent non-terminal residues linked to other residues only by β-1,3 linkages may provide a protective antibody response, e.g. against *C. albicans*.

In further embodiments, a conjugate may include two different glucans e.g. a first glucan having a β(1-3):β(1-6) ratio of between 1.5:1 and 7.5:1, and a second glucan having exclusively or mainly β-1,3 linkages. For instance a conjugate may include both a laminarin glucan and a curdlan glucan.

Where a β-glucan includes both β-1,3 and β-1,6 linkages at a desired ratio and/or sequence then this glucan may be found in nature (e.g. a laminarin), or it may be made artificially. For instance, it may be made by chemical synthesis, in whole or in part. Methods for the chemical synthesis of β-1,3/β-1,6 glucans are known, for example from references 74-84. β-glucan including both β-1,3 and β-1,6 linkages at a desired ratio may also be made starting from an available glucan and treating it with a β-1,6-glucanase (also known as glucan endo-1,6-β-glucosidase, 1,6-β-D-glucan glucanohydrolase, etc.; EC 3.2.1.75) or a β-1,3-glucanase (such as an exo-1,3-glucanase (EC 3.2.1.58) or an endo-1,3-glucanase (EC 3.2.1.39) until a desired ratio and/or sequence is reached.

When a glucan containing solely β-1,3-linked glucose is desired then β-1,6-glucanase treatment may be pursued to completion, as β-1,6-glucanase will eventually yield pure β-1,3 glucan. More conveniently, however, a pure β-1,3-glucan may be used. These may be made synthetically, by chemical and/or enzymatic synthesis e.g. using a (1→3)-β-D-glucan synthase, of which several are known from many organisms (including bacteria, yeasts, plants and fungi). Methods for the chemical synthesis of β-1,3 glucans are known, for example from references 85-88. As a useful alternative to synthesis, a natural β-1,3-glucan may be used, such as a curdlan (linear (β-1,3-glucan from an *Agrobacterium* previously known as *Alcaligenes faecalis* var. *myxogenes*; commercially available e.g. from Sigma-Aldrich catalog C7821) or paramylon (β-1,3-glucan from *Euglena*). Organisms producing high levels of β-1,3-glucans are known in the art e.g. the *Agrobacterium* of refs. 89 & 90, or the *Euglena gracilis* of ref. 91.

Laminarin and curdlan are typically found in nature as high molecular weight polymers e.g. with a molecular weight of at least 100 kDa. They are often insoluble in aqueous media. In their natural forms, therefore, they are not well suited to immunisation. Thus the invention may use a shorter glucan e.g. those containing 60 or fewer glucose monosaccharide units (e.g. 59, 58, 57, 56, 55, 54, 53, 52, 51, 50, 49, 48, 47, 46, 45, 44, 43, 42, 41, 40 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4). A glucan having a number of glucose residues in the range of 2-60 may be used e.g. between 10-50 or between 20-40 glucose units. A glucan with 25-30 glucose residues is particularly useful. Suitable glucans may be formed e.g. by acid hydrolysis of a natural glucan, or by enzymatic digestion e.g. with a glucanase, such as a β-1,3-glucanase. A glucan with 11-19, e.g. 13-19 and particularly 15 or 17, glucose monosaccharide units is also useful. In particular, glucans with the following structures (A) or (B) are specifically envisaged for use in the present invention:

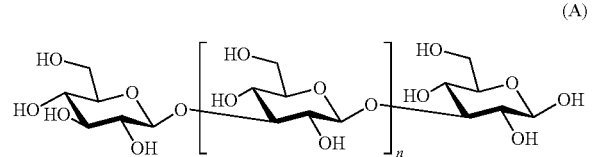

(A)

wherein n+2 is in the range of 2-60, e.g. between 10-50 or between 2-40. Preferably, n+2 is in the range of 25-30 or 11-19, e.g. 13-17. The inventors have found that n+2=15 is suitable.

wherein n is in the range of 0-9, e.g. between 1-7 or between 2-6. Preferably, n is in the range of 3-4 or 1-3.

The inventors have found that n=2 is suitable.

In some embodiments, the glucan is a single molecular species. In these embodiments, all of the glucan molecules are identical in terms of sequence. Accordingly, all of the glucan molecules are identical in terms of their structural properties, including molecular weight etc. Typically, this form of glucan is obtained by chemical synthesis, e.g. using the methods described above. For example, reference 86 describes the synthesis of a single β-1,3 linked species. Alternatively, in other embodiments, the glucan may be obtained from a natural glucan, e.g. a glucan from *L. digitata*, *Agrobacterium* or *Euglena* as described above, with the glucan being purified until the required single molecular species is obtained. Natural glucans that have been purified in this way are commercially available. A glucan that is a single molecular species may be identified by measuring the polydispersity (Mw/Mn) of the glucan sample. This parameter can conveniently be measured by SEC-MALLS, for example as described in reference 92. Suitable glucans for use in this embodiment of the invention have a polydispersity of about 1, e.g. 1.01 or less.

Solubility of natural glucans, such as curdlan, can be increased by introducing ionic groups (e.g. by sulfation, particularly at 0-6 in curdlan). Such modifications may be used with the invention, but are ideally avoided as they may alter the glucan's antigenicity.

When the saccharide is a glucan, it is typically a laminarin.

S. Pneumoniae Capsular Saccharides

As discussed above, the saccharide may also be a bacterial capsular saccharide. Further exemplary bacterial capsular saccharides include those from *S. pneumoniae*. However, in some embodiments, the saccharide is not a capsular saccharide from *S. pneumoniae*.

When the saccharide is a capsular saccharides from *S. pneumoniae*, it is typically from one of the following pneumococcal serotypes: 1, 2, 3, 4, 5, 6A, 6B, 7F, 8, 9N, 9V, 10A, 11A, 12F, 14, 15B, 17F, 18C, 19A, 19F, 20, 22F, 23F and 33F, preferably from 1, 5, 6B, 14, 19F and 23F. Capsular polysaccharides from *S. pneumoniae* comprise repeating oligosaccharide units which may contain up to 8 sugar residues. The oligosaccharide units for the main *S. pneumoniae* serotypes are described in FIG. 1A and FIG. 1B and refs 93 and 94.

S. Agalactiae Capsular Saccharides

Further exemplary bacterial capsular saccharides include those from *Streptococcus agalactiae* ("GBS"). The capsular saccharide is covalently linked to the peptidoglycan back-

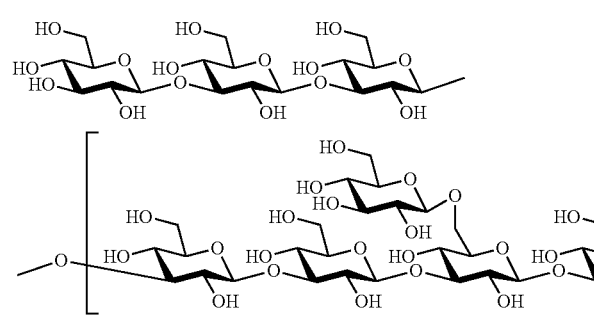

(B)

bone of GBS, and is distinct from the group B antigen, which is another saccharide that is attached to the peptidoglycan backbone.

The GBS capsular saccharides are chemically related, but are antigenically very different. All GBS capsular saccharides share the following trisaccharide core:

β-D-GlcpNAc(1→3)β-D-Galp(1→4)β-D-Glcp

The various GBS serotypes differ by the way in which this core is modified. The difference between serotypes Ia and III, for instance, arises from the use of either the GlcNAc (Ia) or the Gal (III) in this core for linking consecutive trisaccharide cores. Serotypes Ia and Ib both have a [α-D-NeupNAc(2→3)β-D-Galp-(1→] disaccharide linked to the GlcNAc in the core, but the linkage is either 1→4 (Ia) or 1→3 (Ib).

GBS-related disease arises primarily from serotypes Ia, Ib, II, III, IV, V, VI, VII, and VIII, with over 85% being caused by five serotypes: Ia, Ib, III & V. The invention may use a saccharide from one of these four serotypes. The capsular saccharides of each of these four serotypes include: (a) a terminal N-acetyl-neuraminic acid (NeuNAc) residue (commonly referred to as sialic acid), which in all cases is linked 2→3 to a galactose residue; and (b) a N-acetyl-glucosamine residue (GlcNAc) within the trisaccharide core.

All four saccharides include galactose residues within the trisaccharide core, but serotypes Ia, Ib, II & III also contain additional galactose residues in each repeating unit.

Saccharides used according to the invention may be in their native form, or may have been modified. For example, the saccharide may be shorter than the native capsular saccharide, or may be chemically modified. In particular, the serotype V capsular saccharide used in the invention may be modified as described in refs. 95 and 96. For example, a serotype V capsular saccharide that has been substantially desialylated. Desialylated GBS serotype V capsular saccharide may be prepared by treating purified GBS serotype V capsular saccharide under mildly acidic conditions (e.g. 0.1M sulphuric acid at 80° C. for 60 minutes) or by treatment with neuraminidase, as described in reference 95. Thus the saccharide used according to the invention may be a substantially full-length capsular polysaccharide, as found in nature, or it may be shorter than the natural length. Full-length polysaccharides may be depolymerised to give shorter fragments for use with the invention e.g. by hydrolysis in mild acid, by heating, by sizing chromatography, etc. In particular, the serotype II and/or III capsular saccharides used in the invention may be depolymerised as described in refs. 97 and 98.

The saccharide may be chemically modified relative to the capsular saccharide as found in nature. For example, the saccharide may be de-O-acetylated (partially or fully), de-N-acetylated (partially or fully), N-propionated (partially or fully), etc. De-acetylation may occur before, during or after conjugation, but preferably occurs before conjugation. Depending on the particular saccharide, de-acetylation may or may not affect immunogenicity. The relevance of O-acetylation on GBS saccharides in various serotypes is discussed in reference 99, and in some embodiments O-acetylation of sialic acid residues at positions 7, 8 and/or 9 is retained before, during and after conjugation e.g. by protection/de-protection, by re-acetylation, etc. However, typically the GBS saccharide used in the present invention has substantially no O-acetylation of sialic acid residues at positions 7, 8 and/or 9. In particular, when the GBS saccharide has been purified by base extraction as described below, then O-acetylation is typically lost. The effect of de-acetylation etc. can be assessed by routine assays.

Capsular saccharides can be purified by known techniques, as described in 100. A typical process involves base extraction, centrifugation, filtration, RNase/DNase treatment, protease treatment, concentration, size exclusion chromatography, ultrafiltration, anion exchange chromatography, and further ultrafiltration. Treatment of GBS cells with the enzyme mutanolysin, which cleaves the bacterial cell wall to free the cell wall components, is also useful.

As an alternative, the purification process described in reference 101 can be used. This involves base extraction, ethanol/CaCl$_2$ treatment, CTAB precipitation, and re-solubilisation. A further alternative process is described in reference 102.

S. Aureus Capsular Saccharides

Further exemplary bacterial capsular saccharides include those from *S. aureus*, particularly the capsular polysaccharides of *S. aureus* type 5 and type 8. The structures of type 5 and type 8 capsular polysaccharides were described in references 103 and 104 as:

Type 5
→4)-β-D-ManNAcA(3OAc)-(1→4)-α-L-FucNAc
(1→3)-β-D-FucNAc-(1→

Type 8
→3)-β-D-ManNAcA(4OAc)-(1→3)-α-L-FucNAc
(1→3)-β-D-FucNAc-(1→

Recent NMR spectroscopy data [105] has led to a revision of these structures to:

Type 5
→4)-β-D-ManNAcA-(1→4)-α-L-FucNAc(3OAc)-
(1→3)-β-D-FucNAc-(1→

Type 8
→3)-β-D-ManNAcA(4OAc)-(1→3)-α-L-FucNAc
(1→3)-α-D-FucNAc(1→

The polysaccharide may be chemically modified relative to the capsular polysaccharide as found in nature.

For example, the polysaccharide may be de-O-acetylated (partially or fully), de-N-acetylated (partially or fully), N-propionated (partially or fully), etc. De-acetylation may occur before, during or after conjugation, but typically occurs before conjugation. Depending on the particular polysaccharide, de-acetylation may or may not affect immunogenicity e.g. the NeisVac-C™ vaccine uses a de-O-acetylated polysaccharide, whereas Menjugate™ is acetylated, but both vaccines are effective. The effect of de-acetylation etc. can be assessed by routine assays. For example, the relevance of O-acetylation on *S. aureus* type 5 or type 8 capsular polysaccharides is discussed in reference 106. The native polysaccharides are said in this document to have 75% O-acetylation. These polysaccharides induced antibodies to both the polysaccharide backbone and O-acetyl groups. Polysaccharides with 0% O-acetylation still elicited antibodies to the polysaccharide backbone. Both types of antibody were opsonic against *S. aureus* strains that varied in their O-acetyl content. Accordingly, the type 5 or type 8 capsular polysaccharides used in the present invention may have between 0 and 100% O-acetylation.

The degree of O-acetylation of the polysaccharide can be determined by any method known in the art, for example, by proton NMR (e.g. as described in references 107, 108, 109 or 110). A further method is described in reference 111. Similar methods may be used to determine the degree of N-acetylation of the polysaccharide. O-acetyl groups may be removed by hydrolysis, for example by treatment with a base such as anhydrous hydrazine [112] or NaOH [106]. Similar methods may be used to remove N-acetyl groups. To maintain high levels of O-acetylation on type 5 and/or 8 capsular polysaccharides, treatments that lead to hydrolysis of the O-acetyl groups are minimised, e.g. treatments at extremes of pH.

Capsular polysaccharides can be purified by known techniques, as described in the references herein. A typical process involves phenol-ethanol inactivation of *S. aureus* cells, centrifugation, lysostaphin treatment, RNase/DNase treatment, centrifugation, dialysis, protease treatment, further dialysis, filtration, precipitation with ethanol/$CaCl_2$, dialysis, freeze-drying, anion exchange chromatography, dialysis, freeze-drying, size exclusion chromatography, dialysis and freeze-drying [113]. An alternative process involves autoclaving *S. aureus* cells, ultrafiltration of the polysaccharide-containing supernatant, concentration, lyophilisation, treatment with sodium metaperiodate to remove teichoic acid, further ultrafiltration, diafiltration, high performance size exclusion liquid chromatography, dialysis and freeze-drying [114].

The invention is not limited to polysaccharides purified from natural sources, however, and the polysaccharides may be obtained by other methods, such as total or partial synthesis.

Other Bacterial Capsular Saccharides

Further exemplary bacterial capsular saccharides include those from *Haemophilus influenzae* Type b, *Salmonella enterica* Typhi Vi and *Clostridium difficile*.

S. agalactiae Carbohydrate

The invention may also use non-capsular bacterial saccharides. An exemplary non-capsular bacterial saccharides is the *S. pyogenes* GAS carbohydrate (also known as the GAS cell wall polysaccharide, or GASP). This saccharide features a branched structure with an L-rhamnopyranose (Rhap) backbone consisting of alternating alpha-(1→2) and alpha-(1→3) links and D-N-acetylglucosamine (GlcpNAc) residues beta-(1→3)-connected to alternating rhamnose rings ([115]).

The GAS carbohydrate will generally be in its native form, but it may have been modified. For example, the saccharide may be shorter than the native GAS carbohydrate, or may be chemically modified.

Thus the saccharide used according to the invention may be a substantially full-length GAS carbohydrate, as found in nature, or it may be shorter than the natural length. Full-length polysaccharides may be depolymerised to give shorter fragments for use with the invention e.g. by hydrolysis in mild acid, by heating, by sizing chromatography, etc. A short fragment thought to correspond to the terminal unit on the GAS carbohydrate has been proposed for use in a vaccine [116]. Accordingly, short fragments are envisaged in the present invention. However, it is preferred to use saccharides of substantially full-length. The GAS carbohydrate typically has a molecular weight of about 10, in particular about 7.5-8.5 kDa. Molecular masses can be measured by HPLC, for example SEC-HPLC using a TSK Gel G3000SW column (Sigma) relative to pullulan standards, such as those available from Polymer Standard Service [117].

The saccharide may be chemically modified relative to the GAS carbohydrate as found in nature. For example, the saccharide may be de-N-acetylated (partially or fully), N-propionated (partially or fully), etc. The effect of de-acetylation etc., for example on immunogenicity, can be assessed by routine assays.

The Conjugate

The invention involves a conjugate comprising an antigen and a carrier molecule, wherein the carrier molecule comprises a spr0096 antigen and a spr2021 antigen.

The carrier molecule may be covalently conjugated to the antigen directly or via a linker. Any suitable conjugation reaction can be used, with any suitable linker where desired.

Attachment of the antigen to the carrier is preferably via a —$NH_2$ group e.g. in the side chain of a lysine residue in a carrier protein, or of an arginine residue. Where the antigen has a free aldehyde group, then this can react with an amine in the carrier to form a conjugate by reductive amination. Attachment to the carrier may also be via a —SH group e.g. in the side chain of a cysteine residue. Alternatively the antigen may be attached to the carrier via a linker molecule.

The antigen will typically be activated or functionalised prior to conjugation. Activation may involve, for example, cyanylating reagents such as CDAP (e.g. 1-cyano-4-dimethylamino pyridinium tetrafluoroborate [118, 119, etc.]). Other suitable techniques use carbodiimides, hydrazides, active esters, norborane, p-nitrobenzoic acid, N-hydroxysuccinimide, S—NHS, EDC, TSTU (see also the introduction to reference 7).

Direct linkages to the protein may comprise oxidation of the antigen followed by reductive amination with the protein, as described in, for example, references 120 and 121.

Linkages via a linker group may be made using any known procedure, for example, the procedures described in references 122 and 123. Typically, the linker is attached via the anomeric carbon of a saccharide antigen. A preferred type of linkage is an adipic acid linker, which may be formed by coupling a free —$NH_2$ group (e.g. introduced to a saccharide by amination) with adipic acid (using, for example, diimide activation), and then coupling a protein to the resulting antigen-adipic acid intermediate [5, 124, 125]. A similar preferred type of linkage is a glutaric acid linker, which may be formed by coupling a free —$NH_2$ group with glutaric acid in the same way. Adipid and glutaric acid linkers may also be formed by direct coupling to the antigen, i.e. without prior introduction of a free group, e.g. a free —$NH_2$ group, to the antigen, followed by coupling a protein to the resulting antigen-adipic/glutaric acid intermediate. Another preferred type of linkage is a carbonyl linker, which may be formed by reaction of a free hydroxyl group of a modified antigen with CDI [126, 127] followed by reaction with a protein to form a carbamate linkage. Other linkers include β-propionamido [128], nitrophenyl-ethylamine [129], haloacyl halides [130], glycosidic linkages [131], 6-aminocaproic acid [132], N-succinimidyl-3-(2-pyridyldithio)-propionate (SPDP) [133], adipic acid dihydrazide ADH [134], $C_4$ to $C_{12}$ moieties [135], etc. Carbodiimide condensation can also be used [136].

A bifunctional linker may be used to provide a first group for coupling to an amine group in the antigen (e.g. introduced to the antigen by amination) and a second group for coupling to the carrier (typically for coupling to an amine in the carrier). Alternatively, the first group is capable of direct coupling to the antigen, i.e. without prior introduction of a group, e.g. an amine group, to the antigen.

In some embodiments, the first group in the bifunctional linker is thus able to react with an amine group (—$NH_2$) on the antigen. This reaction will typically involve an electrophilic substitution of the amine's hydrogen. In other embodiments, the first group in the bifunctional linker is able to react directly with the antigen. In both sets of embodiments, the second group in the bifunctional linker is typically able to react with an amine group on the carrier. This reaction will again typically involve an electrophilic substitution of the amine.

Where the reactions with both the antigen and the carrier involve amines then it is preferred to use a bifunctional linker. For example, a homobifunctional linker of the formula X-L-X may be used, where: the two X groups are the same as each other and can react with the amines; and where L is a linking moiety in the linker. Similarly, a heterobifunctional linker of the formula X-L-X may be used, where: the two X groups are different and can react with the amines; and where L is a linking moiety in the linker. A preferred X group is N-oxysuccinimide. L preferably has formula L'-L$^2$-L', where L' is carbonyl. Preferred L$^2$ groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$— or —$(CH_2)_3$—.

Similarly, where the reaction with the antigen involves direct coupling and the reaction with the carrier involves an amine then it is also preferred to use a bifunctional linker. For example, a homobifunctional linker of the formula X-L-X may be used, where: the two X groups are the same as each other and can react with the antigen/amine; and where L is a linking moiety in the linker. Similarly, a heterobifunctional linker of the formula X-L-X may be used, where: the two X groups are different and one can react with the antigen while the other can react with the amine; and where L is a linking moiety in the linker. A preferred X group is N-oxysuccinimide. L preferably has formula L'-L$^2$-L', where L' is carbonyl. Preferred L$^2$ groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$— or —$(CH_2)_3$—.

Other X groups for use in the bifunctional linkers described in the two preceding paragraphs are those which form esters when combined with HO-L-OH, such as norborane, p-nitrobenzoic acid, and sulfo-N-hydroxysuccinimide.

Further bifunctional linkers for use with the invention include acryloyl halides (e.g. chloride) and haloacylhalides.

The linker will generally be added in molar excess to antigen during coupling to the antigen.

When the antigen has a single group that is linked to the carrier molecule (optionally via a linker), and the carrier has multiple groups that are linked to different antigen/linker molecules, the resultant conjugate may form a "star" structure. This structure comprises a central carrier molecule with multiple antigen molecules radiating from the carrier (optionally via linkers). When the antigen has more than one group that is linked to the carrier molecule (optionally via a linker), and the carrier has more than one group that is linked to different antigen/linker molecules, the resultant conjugate may form a "net" structure. This structure comprises a network of carrier molecules connected by antigen molecules (optionally via linkers).

Conjugates may have excess carrier (w/w) or excess antigen (w/w) e.g. in the ratio range of 1:5 to 5:1. Conjugates with excess carrier protein are typical e.g. in the range 0.2:1 to 0.9:1, or equal weights. The conjugate may include small amounts of free (i.e. unconjugated) carrier. When a given carrier protein is present in both free and conjugated form in a composition of the invention, the unconjugated form is preferably no more than 5% of the total amount of the carrier protein in the composition as a whole, and more preferably present at less than 2% (by weight).

When the conjugate is comprised within a pharmaceutical composition of the invention, the composition may also comprise free carrier protein as immunogen [137].

After conjugation, free and conjugated antigens can be separated. There are many suitable methods e.g. hydrophobic chromatography, tangential ultrafiltration, diafiltration, etc. [see also refs. 138, 139 etc.]. Tangential flow ultrafiltration is preferred.

A saccharide moiety in the conjugate is preferably a low molecular weight saccharide or an oligosaccharide, as defined above. Oligosaccharides will typically be sized prior to conjugation.

The conjugate is preferably soluble in water and/or in a physiological buffer.

Production and Conjugation of Carrier Molecules Modified to Incorporate Non-Natural Amino Acids Where one or more non-natural amino acid residues is to be incorporated into the carrier molecule, then this can be performed using standard procedures. One such method comprises the use of modified host cells in which the amino acyl tRNA synthetase for a specific codon has been engineered to conjugate the tRNA to a non-natural amino acid which is then incorporated into the carrier during translation [see ref. 140 for a review of such techniques]. Alternatively, some procedures exploit the fact that some non-natural amino acids are incorporated into proteins by the native cellular machinery when the natural cognate amino acid is not present. An example of this second type of procedure is observed in the incorporation of HAG. Here, in some cells, if the cell has low or no methionine, then the native cellular machinery will incorporate HAG in place of methionine in the initiation and elongation steps of protein synthesis. Many host cells used for protein expression are prototrophic for methionine, i.e. the cell can synthesise this amino acid de novo. By using cells that are methionine auxotrophs, therefore, it is possible to lower the levels of methionine to such a low level that HAG is incorporated into proteins in place of methionine. Example methionine auxotrophic host cells include *E. coli* strains B834 (DE3) (Merck) and T7 Express Crystal (NEB), although other suitable strains will be immediately apparent to the skilled person.

The conjugation technique/reaction used to conjugate the carrier molecule should be appropriate for the functional group in the non-natural amino acid. For example, where the non-natural amino acid is HAG, then thiyl-ene conjugation is used [see, e.g., ref. 141].

Mixtures Comprising the Conjugates

The conjugates of the invention may be mixed with further antigens. These further antigens may be other conjugates of the invention or they may be other antigens.

For example, mixtures of conjugates are envisaged. At least one of the conjugates in these mixtures is a conjugate of the invention, i.e. the carrier molecule comprises a spr0096 antigen and a spr2021 antigen. Typically, the other conjugate(s) in these mixtures will also be conjugates of the invention. However, when the other conjugate(s) are not conjugates of the invention, the carrier molecule may be any suitable carrier protein (as described below), typically the same carrier molecule in each conjugate.

For example, mixtures of conjugates from more than one serogroup of *N. meningitidis* are envisaged e.g. compositions comprising saccharides from serogroups A+C, A+W135, A+Y, C+W135, C+Y, W135+Y, A+C+W135, A+C+Y, C+W135+Y, A+C+W135+Y, etc. Typically, the mixture is a mixture of conjugates comprising saccharides from serogroups A, C, W135 and Y. At least one of the conjugates in these mixtures is a conjugate of the invention, i.e. the carrier molecule comprises a spr0096 antigen and a spr2021 antigen. Typically, the other conjugate(s) in these mixtures will also be conjugates of the invention. However, when the other conjugate(s) are not conjugates of the invention, the carrier molecule may be any suitable carrier protein (as described below), typically the same carrier molecule in each conjugate.

Suitable carrier proteins are bacterial toxins, such as diphtheria or tetanus toxins, or toxoids or mutants thereof. The inventors have found that the CRM197 diphtheria toxin mutant [142] is particularly suitable. Other suitable carrier proteins include the *N. meningitidis* outer membrane protein complex [143], synthetic peptides [144,145], heat shock proteins [146,147], pertussis proteins [148,149], cytokines [150], lymphokines [150], hormones [150], growth factors [150], human serum albumin (typically recombinant), artificial proteins comprising multiple human CD4$^+$ T cell epitopes from various pathogen-derived antigens [17] such as N19 [151], protein D from *H. influenzae* [152-154], pneumococcal surface protein PspA [155], pneumolysin [156] or its non-toxic derivatives [157], iron-uptake proteins [158], toxin A or B from *C. difficile* [159], a GBS protein [160], a GAS protein etc.

A single carrier protein might carry more than one polysaccharide antigen [162,163]. To achieve this goal, different saccharides can be mixed prior to the conjugation process. Typically, however, there are separate conjugates for each saccharide, with the different saccharides being mixed after conjugation. The separate conjugates may be based on the same carrier, particularly the same carrier comprising a spr0096 antigen and a spr2021 antigen.

A mixture of the invention may for example be a mixture of separate conjugates for each saccharide from serogroups A, C, W135 and Y, wherein the serogroup A conjugate is a conjugate of the invention, i.e. the carrier molecule comprises a spr0096 antigen and a spr2021 antigen, and the serogroup C, W135 and Y conjugates are not conjugates of the invention. In this embodiment, the carrier molecule in the serogroup C, W135 and Y conjugates is typically CRM197.

Where a mixture comprises capsular saccharides from both serogroups A and C, it is preferred that the ratio (w/w) of MenA saccharide:MenC saccharide is greater than 1 (e.g. 2:1, 3:1, 4:1, 5:1, 10:1 or higher).

Where a mixture comprises capsular saccharides from serogroup Y and one or both of serogroups C and W135, it is preferred that the ratio (w/w) of MenY saccharide:MenW135 saccharide is greater than 1 (e.g. 2:1, 3:1, 4:1, 5:1, 10:1 or higher) and/or that the ratio (w/w) of MenY saccharide:MenC saccharide is less than 1 (e.g. 1:2, 1:3, 1:4, 1:5, or lower).

Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Typically, the ratio is 2:1:1:1.

The mixtures may also comprise proteins. For example, the mixtures may include proteins from serogroup B of *N. meningitidis* [e.g. refs. 164 to 169] or OMV preparations [e.g. refs. 170 to 173 etc.].

The further antigen(s) may comprise antigens from non-*N. meningitidis* pathogens. Thus the compositions of the invention may further comprise one or more non-*N. meningitidis* antigens, including additional bacterial, viral or parasitic antigens. These may be selected from the following:

a saccharide antigen from *Streptococcus pneumoniae* [e.g. refs. 174-176; chapters 22 & 23 of ref. 183].

an antigen from hepatitis A virus, such as inactivated virus [e.g. 177, 178; chapter 15 of ref. 183].

an antigen from hepatitis B virus, such as the surface and/or core antigens [e.g. 178, 179; chapter 16 of ref. 183].

an antigen from hepatitis C virus [e.g. 180].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 181 & 182; chapter 21 of ref. 183].

a diphtheria antigen, such as a diphtheria toxoid [e.g. chapter 13 of ref. 183].

a tetanus antigen, such as a tetanus toxoid [e.g. chapter 27 of ref. 183].

a saccharide antigen from *Haemophilus influenzae* B [e.g. chapter 14 of ref. 183]

an antigen from *N. gonorrhoeae* [e.g. 164 to 167]

an antigen from *Chlamydia pneumoniae* [e.g. 184, 185, 186, 187, 188, 189, 190].

an antigen from *Chlamydia trachomatis* [e.g. 191].

an antigen from *Porphyromonas gingivalis* [e.g. 192].

polio antigen(s) [e.g. 193, 194; chapter 24 of ref. 183] such as IPV.

rabies antigen(s) [e.g. 195] such as lyophilised inactivated virus [e.g. 196, RabAvert™]

measles, mumps and/or rubella antigens [e.g. chapters 19, 20 and 26 of ref. 183].

influenza antigen(s) [e.g. chapters 17 & 18 of ref. 183], such as the haemagglutinin and/or neuraminidase surface proteins.

an antigen from *Moraxella catarrhalis* [e.g. 197].

an antigen from *Streptococcus pyogenes* (group A *streptococcus*) [e.g. 198, 199, 200].

an antigen from *Streptococcus agalactiae* (group B *streptococcus*) [e.g. 160, 201-203].

an antigen from *S. epidermidis* [e.g. type I, II and/or III capsular polysaccharide obtainable from strains ATCC-31432, SE-360 and SE-10 as described in refs. 204, 205 and 206].

Where a saccharide or carbohydrate antigen is used, it is typically conjugated to a carrier in order to enhance immunogenicity. The carrier molecule may be a carrier of the invention, i.e. a carrier that comprises a spr0096 antigen and a spr2021 antigen. Alternatively, the carrier molecule may be any suitable carrier protein, e.g. as described above. Conjugation of *H. influenzae* B, meningococcal and pneumococcal saccharide antigens is well known.

Toxic protein antigens may be detoxified where necessary (e.g. detoxification of pertussis toxin by chemical and/or genetic means [182]).

Where a diphtheria antigen is included in the composition it is typical also to include tetanus antigen and pertussis antigens. Similarly, where a tetanus antigen is included it is typical also to include diphtheria and pertussis antigens. Similarly, where a pertussis antigen is included it is typical also to include diphtheria and tetanus antigens.

Antigens may be adsorbed to an aluminium salt.

Antigens in the composition will typically be present at a concentration of at least 1 µg/ml each. In general, the concentration of any given antigen will be sufficient to elicit an immune response against that antigen.

As an alternative to using proteins antigens in the composition of the invention, nucleic acid encoding the antigen may be used [e.g. refs. 207 to 215]. Protein components of the compositions of the invention may thus be replaced by nucleic acid (usually DNA e.g. in the form of a plasmid) that encodes the protein.

In practical terms, there may be an upper limit to the number of antigens included in compositions of the invention. The number of antigens (including conjugates of the invention) in a composition of the invention may be less than 20, less than 19, less than 18, less than 17, less than 16, less than 15, less than 14, less than 13, less than 12, less than 11, less than 10, less than 9, less than 8, less than 7, less than 6, less than 5, less than 4, or less than 3. The number of conjugates of the invention in a composition may be less than 6, less than 5, or less than 4.

Pharmaceutical Compositions Comprising the Conjugates

The invention provides a pharmaceutical composition comprising (a) a conjugate of the invention, and (b) a pharmaceutically acceptable carrier. A thorough discussion of such carriers is available in reference 216.

Microbial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops, as a spray, or as a powder [e.g. 217]. The composition may be included in a mouthwash. The composition may be lyophilised.

The pharmaceutical composition is preferably sterile. It is preferably pyrogen-free. It is preferably buffered e.g. at between pH 6 and pH 8, generally around pH 7.

The invention also provides a delivery device containing a pharmaceutical composition of the invention. The device may be, for example, a syringe or an inhaler.

Pharmaceutical compositions of the invention are preferably immunogenic compositions, in that they comprise an immunologically effective amount of an antigen. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

Once formulated, the compositions of the invention can be administered directly to the subject. The subjects to be treated can be animals; in particular, human subjects can be treated.

Immunogenic compositions of the invention may be used therapeutically (i.e. to treat an existing infection) or prophylactically (i.e. to prevent future infection). Therapeutic immunisation is particularly useful for treating *Candida* infection in immunocompromised subjects.

An immunogenic composition may include a further adjuvant, which can function to enhance the immune responses (humoral and/or cellular) elicited in a patient who receives the composition. Adjuvants that can be used with the invention include, but are not limited to:

A mineral-containing composition, including calcium salts and aluminum salts (or mixtures thereof). Calcium salts include calcium phosphate (e.g. the "CAP" particles disclosed in ref. 218). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [219]. The adjuvants known as aluminum hydroxide and aluminum phosphate may be used. These names are conventional, but are used for convenience only, as neither is a precise description of the actual chemical compound which is present (e.g. see chapter 9 of reference 302). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. The invention can use a mixture of both an aluminium hydroxide and an aluminium phosphate. In this case there may be more aluminium phosphate than hydroxide e.g. a weight ratio of at least 2:1 e.g. $\geq 5:1$, $\geq 6:1$, $\geq 7:1$, $\geq 8:1$, $\geq 9:1$, etc. The concentration of $Al^{++}+$ in a composition for administration to a patient is preferably less than 10 mg/ml e.g. $\leq 5$ mg/ml, $\leq 4$ mg/ml, $\leq 3$ mg/ml, $\leq 2$ mg/ml, $\leq 1$ mg/ml, etc. A preferred range is between 0.3 and 1 mg/ml. A maximum of 0.85 mg/dose is preferred.

Saponins [chapter 22 of ref. 302], which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 220. Saponin formulations may also comprise a sterol, such as cholesterol [221]. Combinations of saponins and cholesterols can be used to form unique particles called immunostimulating complexes (ISCOMs) [chapter 23 of ref. 302]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 221-223. Optionally, the ISCOMS may be devoid of additional detergent [224].

A review of the development of saponin based adjuvants can be found in refs. 225 & 226.

Bacterial ADP-ribosylating toxins (e.g. the *E. coli* heat labile enterotoxin "LT", cholera toxin "CT", or pertussis toxin "PT") and detoxified derivatives thereof, such as the mutant toxins known as LT-K63 and LT-R72 [227]. The use of detoxified ADP-ribosylating toxins as mucosal adjuvants is described in ref. 228 and as parenteral adjuvants in ref. 229.

Bioadhesives and mucoadhesives, such as esterified hyaluronic acid microspheres [230] or chitosan and its derivatives [231].

Microparticles (i.e. a particle of ~100 nm to ~150 μm in diameter, more preferably ~200 nm to ~30 μm in diameter, or ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB).

Liposomes (Chapters 13 & 14 of ref. 302). Examples of liposome formulations suitable for use as adjuvants are described in refs. 232-234.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™"), N-acetylmuramyl-L-alanyl-D-isoglutaminyl-L-alanine-2-(1'-2' dipalmitoyl-sn-glycero-3-hydroxyphosphoryloxy)-ethylamine ("MTP-PE").

A polyoxidonium polymer [235,236] or other N-oxidized polyethylene-piperazine derivative.

Methyl inosine 5'-monophosphate ("MIMP") [237].

A polyhydroxlated pyrrolizidine compound [238], such as one having formula:

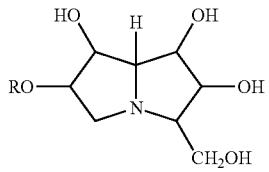

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide [239-246] (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin [247] or derivative thereof, such as algammulin.

An oil-in-water emulsion. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

An immunostimulatory oligonucleotide, such as one containing a CpG motif (a dinucleotide sequence containing an unmethylated cytosine residue linked by a phosphate bond to a guanosine residue), or a CpI motif (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded. References 248, 249 and 250 disclose possible analog substitutions e.g. replacement of guanosine with 2'-deoxy-7-deazaguanosine. The adjuvant effect of CpG oligonucleotides is further discussed in refs. 251-256. A CpG sequence may be directed to TLR9, such as the motif GTCGTT or TTCGTT [257]. The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 258-260. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 257 & 261-263. A useful CpG adjuvant is CpG7909, also known as ProMune™ (Coley Pharmaceutical Group, Inc.). Another is CpG1826. As an alternative, or in addition, to using CpG sequences, TpG sequences can be used [264], and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in ref. 264), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref. 264), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC31™ [265]. Thus an adjuvant used with the invention may comprise a mixture of (i) an oligonucleotide (e.g. between 15-40 nucleotides) including at least one (and preferably multiple) CpI motifs, and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 1). The polycationic polymer may be a peptide comprising 11-mer amino acid sequence KLKLLLLLKLK (SEQ ID NO: 2).

3-O-deacylated monophosphoryl lipid A ('3dMPL', also known as 'MPL™') [266-269]. In aqueous conditions, 3dMPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity [270]. Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm.

An imidazoquinoline compound, such as Imiquimod ("R-837") [271,272], Resiquimod ("R-848") [273], and their analogs; and salts thereof (e.g. the hydrochloride salts). Further details about immunostimulatory imidazoquinolines can be found in references 274 to 278.

A thiosemicarbazone compound, such as those disclosed in reference 279. Methods of formulating, manufacturing, and screening for active compounds are also described in reference 279. The thiosemicarbazones are particularly effective in the stimulation of human peripheral blood mononuclear cells for the production of cytokines, such as TNF-α.

A tryptanthrin compound, such as those disclosed in reference 280. Methods of formulating, manufacturing, and screening for active compounds are also described in reference 280. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

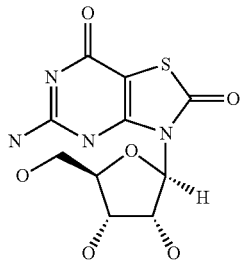 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 281 to 283Loxoribine (7-allyl-8-oxoguanosine) [284].

Compounds disclosed in reference 285, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [286,287], Hydrapthalamide compounds, Benzophenone compounds, Isoxazole compounds, Sterol compounds, Quinazilinone compounds, Pyrrole compounds [288], Anthraquinone compounds, Quinoxaline compounds, Triazine compounds, Pyrazalopyrimidine compounds, and Benzazole compounds [289].

An aminoalkyl glucosaminide phosphate derivative, such as RC-529 [290,291].

A phosphazene, such as poly[di(carboxylatophenoxy) phosphazene] ("PCPP") as described, for example, in references 292 and 293.

A substituted urea or compound of formula I, II or III, or a salt thereof:

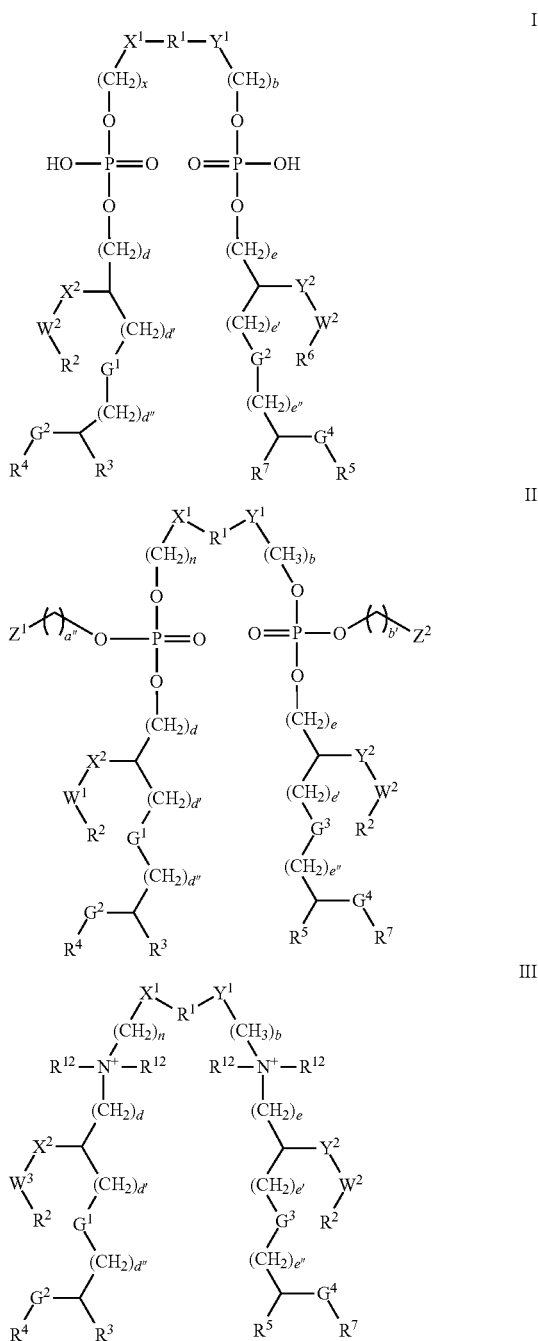

as defined in reference 294, such as 'ER 803058', 'ER 803732', 'ER 804053', ER 804058', 'ER 804059', 'ER 804442', 'ER 804680', 'ER 804764', ER 803022 or 'ER 804057' e.g.:

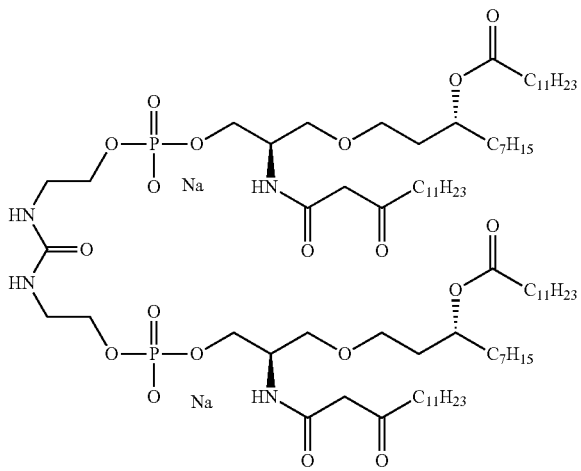

ER804057

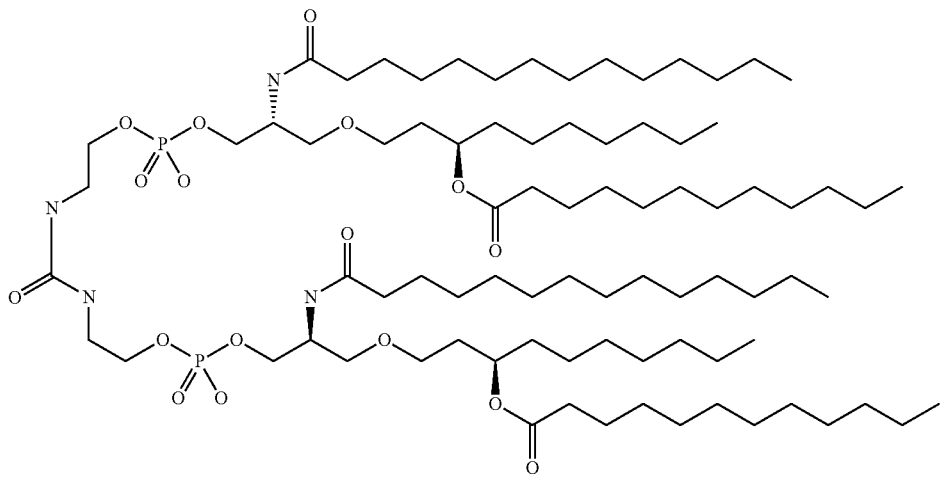

ER-803022

Derivatives of lipid A from *Escherichia coli* such as OM-174 (described in refs. 295 & 296).

Compounds containing lipids linked to a phosphate-containing acyclic backbone, such as the TLR4 antagonist E5564 [297,298]:

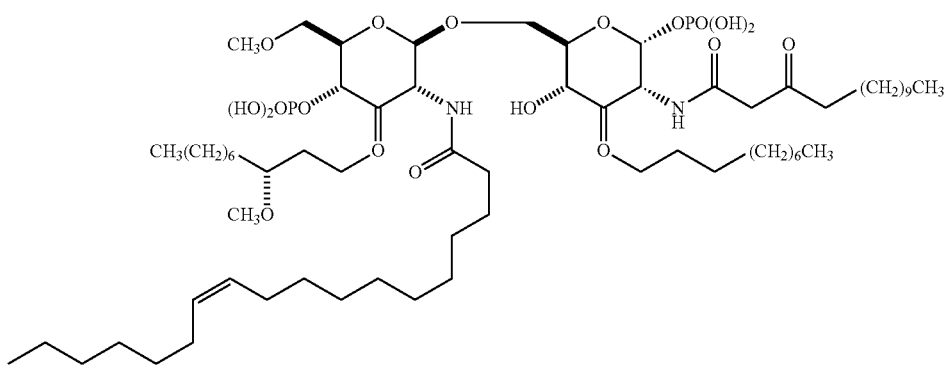

These and other adjuvant-active substances are discussed in more detail in references 302 & 303.

Antigens and adjuvants in a composition will typically be in admixture.

Compositions may include two or more of said adjuvants. For example, they may advantageously include both an oil-in-water emulsion and 3dMPL, etc.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [299-301], as described in more detail in Chapter 10 of ref. 302 and chapter 12 of ref. 303. The MF59 emulsion advantageously includes citrate ions e.g. 10 mM sodium citrate buffer.

An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [304] (0.05-1% Thr-MDP, 5% squalane, 2.5% Pluronic L121 and 0.2% polysorbate 80). It can also be used without the Thr-MDP, as in the "AF" adjuvant [305] (5% squalane, 1.25% Pluronic L121 and 0.2% polysorbate 80). Microfluidisation is preferred.

An emulsion having from 0.5-50% of an oil, 0.1-10% of a phospholipid, and 0.05-5% of a non-ionic surfactant. As described in reference 306, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 307, produced by addition of aliphatic amine to desacylsaponin via the carboxyl group of glucuronic acid), dimethyldioctadecylammonium bromide and/or N,N-dioctadecyl-N,N-bis(2-hydroxyethyl)propanediamine.

An emulsion in which a saponin (e.g. QuilA or QS21) and a sterol (e.g. a cholesterol) are associated as helical micelles [308].

Medical Treatments and Uses

The invention also provides a conjugate of the invention, for use in medicine e.g. for use in raising an antibody response in a mammal.

The invention also provides a method for raising an immune response in a mammal, comprising administering a conjugate or pharmaceutical composition of the invention to the mammal.

The invention also provides the use of a conjugate of the invention in the manufacture of a medicament for preventing or treating a microbial infection in a mammal.

The immune response raised by these methods and uses will generally include an antibody response, preferably a protective antibody response. Methods for assessing antibody responses after antigen immunisation are well known in the art. The antibody response is preferably an IgA or IgG response. The immune response may be prophylactic and/or therapeutic. The mammal is preferably a human.

Efficacy of therapeutic treatment can be tested by monitoring microbial infection after administration of the composition of the invention. Efficacy of prophylactic treatment can be tested by monitoring immune responses against antigen (e.g. anti-antigen antibodies) after administration of the composition.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intradermal, ocular, nasal, aural, or pulmonary administration. Injection or intranasal administration is preferred.

The invention may be used to elicit systemic and/or mucosal immunity.

Vaccines prepared according to the invention may be used to treat both children and adults. Thus a subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), or the young (e.g. ≤5 years old). The vaccines are not suitable solely for these groups, however, and may be used more generally in a population.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

The uses and methods of the invention are particularly useful for treating/protecting against infections caused by the organism from which the antigen is derived. Exemplary uses/methods are discussed below.

*N. Meningitidis* Capsular Saccharides

The uses and methods may be for the prevention and/or treatment of a disease caused by *N. meningitidis*, e.g. meningitis, septicaemia, etc.

Glucans

Because glucans (and β-glucans in particular) are an essential and principal polysaccharide constituent of almost all pathogenic fungi, particularly those involved in infections in immunocompromised subjects, and also in bacterial pathogens and protozoa, anti-glucan immunity may have efficacy against a broad range of pathogens and diseases. For example, anti-glucan serum raised after immunisation with *S. cerevisiae* is cross-reactive with *C. albicans*. Broad spectrum immunity is particularly useful because, for these 10 human infectious fungal agents, chemotherapy is scanty, antifungal drug resistance is emerging and the need for preventative and therapeutic vaccines is increasingly recognized.

The uses and methods of the invention are particularly useful for treating/protecting against infections of: *Candida* species, such as *C. albicans*; *Cryptococcus* species, such as *C. neoformans*; *Enterococcus* species, such as *E. faecalis*; *Streptococcus* species, such as *S. pneumoniae, S. mutans, S. agalactiae* and *S. pyogenes*; *Leishmania* species, such as *L. major*; *Acanthamoeba* species, such as *A. castellani*; *Aspergillus* species, such as *A. fumigatus* and *A lavus*; *Pneumocystis* species, such as *P. carinii*; *Mycobacterium* species, such as *M. tuberculosis*; *Pseudomonas* species, such as *P. aeruginosa*; *Staphylococcus* species, such as *S. aureus*; *Salmonella* species, such as *S. typhimurium*; *Coccidioides* species such as *C. immitis*; *Trichophyton* species such as *T. verrucosum*; *Blastomyces* species such as *B. dermatidis*; *Histoplasma* species such as *H. capsulatum*; *Paracoccidioides* species such as *P. brasiliensis*; *Pythium* species such as *P. insidiosum*; and *Escherichia* species, such as *E. coli*.

The uses and methods are particularly useful for preventing/treating diseases including, but not limited to: candidiasis (including hepatosplenic candidiasis, invasive candidiasis, chronic mucocutaneous candidiasis and disseminated candidiasis); candidemia; aspergillosis, cryptococcosis, dermatomycoses, sporothrychosis and other subcutaneous mycoses, blastomycosis, histoplasmosis, coccidiomycosis, paracoccidiomycosis, pneumocystosis, thrush, tuberculosis, mycobacteriosis, respiratory infections, scarlet fever, pneumonia, impetigo, rheumatic fever, sepsis, septicaemia, cutaneous and visceral leishmaniasis, corneal acanthamoebiasis, cystic fibrosis, typhoid fever, gastroenteritis and hemolyticuremic syndrome. Anti-*C. albicans* activity is particularly useful for treating infections in AIDS patients.

Conjugates of the invention may be combined with non-glucan antigens into a single composition for simultaneous immunisation against multiple pathogens. As an alternative to making a combined vaccine, conjugates may be administered to patients at substantially the same time as (e.g. during the same medical consultation or visit to a healthcare professional or vaccination centre) other vaccines. Antigens for use in these combination vaccines or for concomitant administration include, for instance, immunogens from *Streptococcus agalactiae, Staphylococcus aureus* and/or *Pseudomonas aeuruginosa*, hepatitis A virus, hepatitis B virus, *Neisseria meningitidis* (such as saccharides or conjugated saccharides, for serogroups A, C, W135 and/or Y), *Streptococcus pneumoniae* (such as saccharides or conjugated saccharides), etc.

Conjugates of the invention may be used in conjunction with anti-fungals, particularly where a patient is already infected. The anti-fungal offers an immediate therapeutic effect whereas the conjugate offers a longer-lasting effect. Suitable anti-fungals include, but are not limited to, azoles (e.g. fluconazole, itraconazole), polyenes (e.g. amphotericin B), flucytosine, and squalene epoxidase inhibitors (e.g. terbinafine) [see also ref. 309]. The anti-fungal and the conjugate may be administered separately or in combination. When administered separately, they will typically be administered within 7 days of each other. After the first administration of a conjugate, the anti-fungal may be administered more than once.

*S. Pneumoniae* Capsular Saccharides

The uses and methods may be for the prevention and/or treatment of a disease caused by pneumococcus, e.g. meningitis, sepsis, pneumonia etc.

DEFINITIONS

The practice of the present invention will employ, unless otherwise indicated, conventional methods of chemistry, biochemistry, molecular biology, immunology and pharmacology, within the skill of the art. Such techniques are explained fully in the literature. See, e.g., references 216 and 310-316, etc.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

The term "canonical" in relation to amino acids means that the amino acid is one of the twenty amino acids encoded by the universal genetic code, i.e. Alanine, Asparagine, Aspartic acid, Arginine, Cysteine, Glutamine, Glycine, Glutamic acid, Histidine, Isoleucine, Lysine, Leucine, Phenylalanine, Methionine, Serine, Proline, Tryptophan, Threonine, Tyrosine and Valine.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 317. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 318.

MODES FOR CARRYING OUT THE INVENTION

A. Production and Purification of Conjugates

Laminarin, pneumococcal capsular saccharide from serotype 5 and meningococcal capsular oligosaccharides from serogroups A, C, W135 and Y were conjugated to various known and experimental carrier proteins and purified, as described below.

Lam-96/2021:

Laminarin was conjugated to SEQ ID NO: 9 according to the method of ref. 319 in phosphate buffered saline using activated laminarin at a molar ratio of polysaccharide ester groups to protein of 30 and a protein concentration of 2-10 mg/ml. Conjugates were purified by Immobilized Metal ion Affinity Chromatography (IMAC), making use of the histidine tag on the carrier protein. The purification was performed with His MultiTrap HP Plates™ (GE Healthcare), prepacked 96-well filter plates for small-scale purification of histine-tagged proteins, with the use of a vacuum source. The purified conjugates were characterized by SDS-Page; MicroBCA for protein content; and HPAEC-PAD for saccharide content. Two lots had the following properties:

| Lot | Saccharide (μg/ml) | Protein (μg/ml) | Saccharide:protein |
|---|---|---|---|
| "Old" | 141.0 | 275.0 | 0.5 |
| "New" | 191.4 | 333.0 | 0.6 |

Laminarin was conjugated to SEQ ID NO: 10 (Lam-2021/96) by the same method. For comparison, laminarin was similarly conjugated to the following carrier proteins: CRM197, spr0565B (SEQ ID NO: 11), spr1416 (SEQ ID NO: 12), spr1418 (SEQ ID NO: 13), spr2021 (SEQ ID NO: 3) and spr0096 (SEQ ID NO: 1).

MenA-, C-, W- and Y-96/2021:

meningococcal capsular oligosaccharides from serogroups A, C, W135 and Y were conjugated to SEQ ID NO: 9 using the method described in reference 320. The conjugates were purified by IMAC as described above. The purified conjugates were characterized by SDS-Page, MicroBCA and HPAEC-PAD. Representative conjugates had the following properties:

| Conjugate | Saccharide (μg/ml) | Protein (μg/ml) | Saccharide:protein |
|---|---|---|---|
| MenA-96/2021 | 66 | 223 | 0.3 |
| MenC-96/2021 | 71 | 240 | 0.3 |
| MenW135-96/2021 | 91 | 129 | 0.7 |
| MenY-96/2021 | 70 | 160 | 0.4 |

For comparison, these saccharides were similarly conjugated to CRM197 using the method described in reference 320. A MenA-CRM197 conjugate with a higher saccharide: protein (hereinafter, "high glycosylation") was also made using this method. The meningococcal capsular oligosaccharide from serogroup C was also conjugated to spr1416 (SEQ ID NO: 12).

Pneumo Type 5-96/2021:

pneumococcal capsular saccharide from serotype 5 was sized in a Sephacryl S300 column and oxidised in a solution of NaPi 10 mM, NaCl 500 mM at pH 7.2 with NaIO$_4$ (30% mol of mol PS repeating unit) at room temperature over night. The material was purified by dialysis with 6-8 kDa cut-off membrane against water. Conjugation was carried out by reductive amination using the oxidized saccharide in Na$_2$B$_4$O$_7$ 100 mM, NaCl 100 mM at pH 8.4 (5 mg/ml) at a saccharide:protein ratio of 1:1 (w/w) and a protein: NaBH$_3$CN ratio of 1:1 (w/w) at 37° C. for 48 hours. The conjugates were purified by adding solid ammonium sulphate (500 g/l) to the solution of crude conjugate, holding the mixture for 30 minutes at 0° C. to allow the conjugate to precipitate and then centrifuging and dissolving the pellet in NaPi 10 mM at pH7.2.

The purified conjugates were characterized by SDS-Page, MicroBCA and HPAEC-PAD. Representative conjugates had the following properties:

| Conjugate | Saccharide (μg/ml) | Protein (μg/ml) | Saccharide:protein |
|---|---|---|---|
| Pneumo type 5-96/2021 | 258 | 680 | 0.38 |

For comparison, this saccharide was similarly conjugated to CRM197.

B. Immunogenicity of Lam-96/2021 Compared to Other Laminarin Pneumococcal Protein Conjugates The immunogenicity of the Lam-96/2021 conjugate was compared to laminarin conjugated to other carrier proteins derived from pneumococcal protein antigens. Briefly, saccharide conjugates (at 5 μg saccharide dose) with or without alum adjuvant were administered subcutaneously to Balb/C mice at days 1, 14 and 28. The mice were bled at day 42 and specific anti-laminarin antibodies measured by ELISA (using plates coated with unconjugated laminarin [321]).

Figure 3:
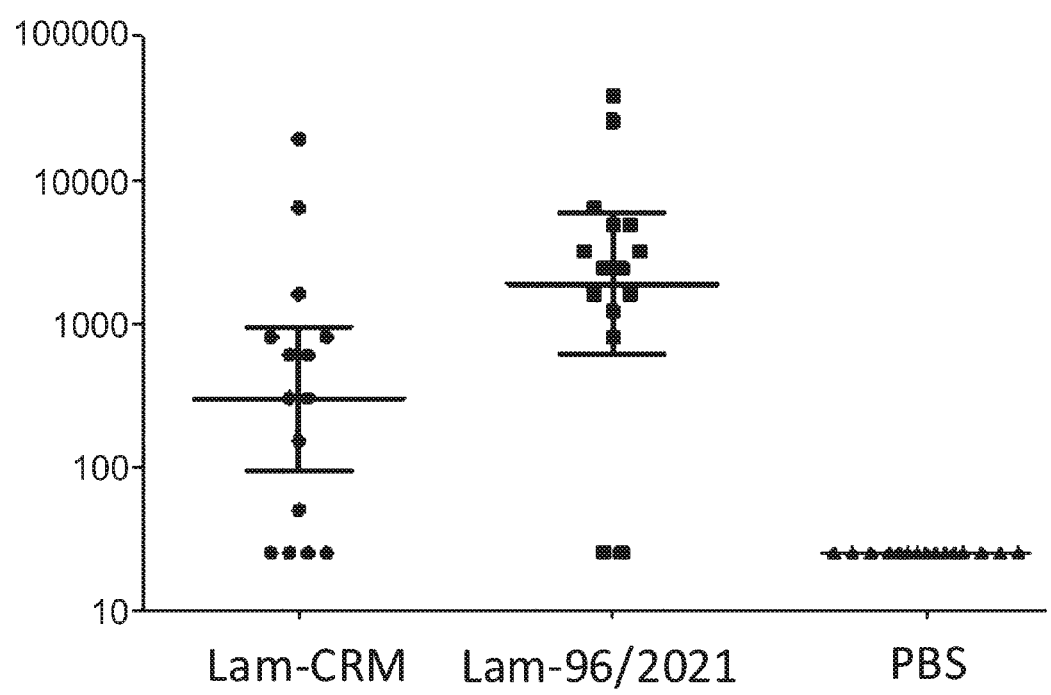
FIG. 3 compares the immunogenicity of a laminarin conjugate of the invention with a reference CRM197 conjugate.

Results are shown in FIG. 2, with the vertical dotted lines denoting separate studies. In the first study, the Lam-96/2021 conjugate was more immunogenic than laminarin conjugates based on spr0565B, spr1416 and spr1418 pneumococcal protein antigens. The conjugate was also more immunogenic than a reference laminarin conjugate based on CRM197 (see FIG. 3, in which the data from the first and third study in FIG. 2 are combined). In the second study, the immunogenicity of a laminarin conjugate based on spr2021 alone was lower than this reference conjugate. In the third study, the Lam-96/2021 conjugate was more immunogenic than a laminarin conjugate based on spr0096 alone. The conjugate was also typically more immunogenic than the reference conjugates based on CRM197, both in the presence and absence of alum adjuvant.

C. Immunogenicity of Other Saccharide Conjugates Based on 96/2021

The immunogenicity of the MenA-, C-, W- and Y-96/2021 and pneumo type 5-96/2021 conjugates was tested using the same schedule as laminarin conjugates and compared to reference conjugates based on CRM197. Balb/C mice were immunized with 2 µg MenA saccharide, 1 µg MenC saccharide, 1 µg MenW saccharide and 1 µg MenY saccharide per dose. Specific anti-polysaccharide antibodies were determined by ELISA assay (using plates coated with the native unconjugated polysaccharide).

Figure 4:
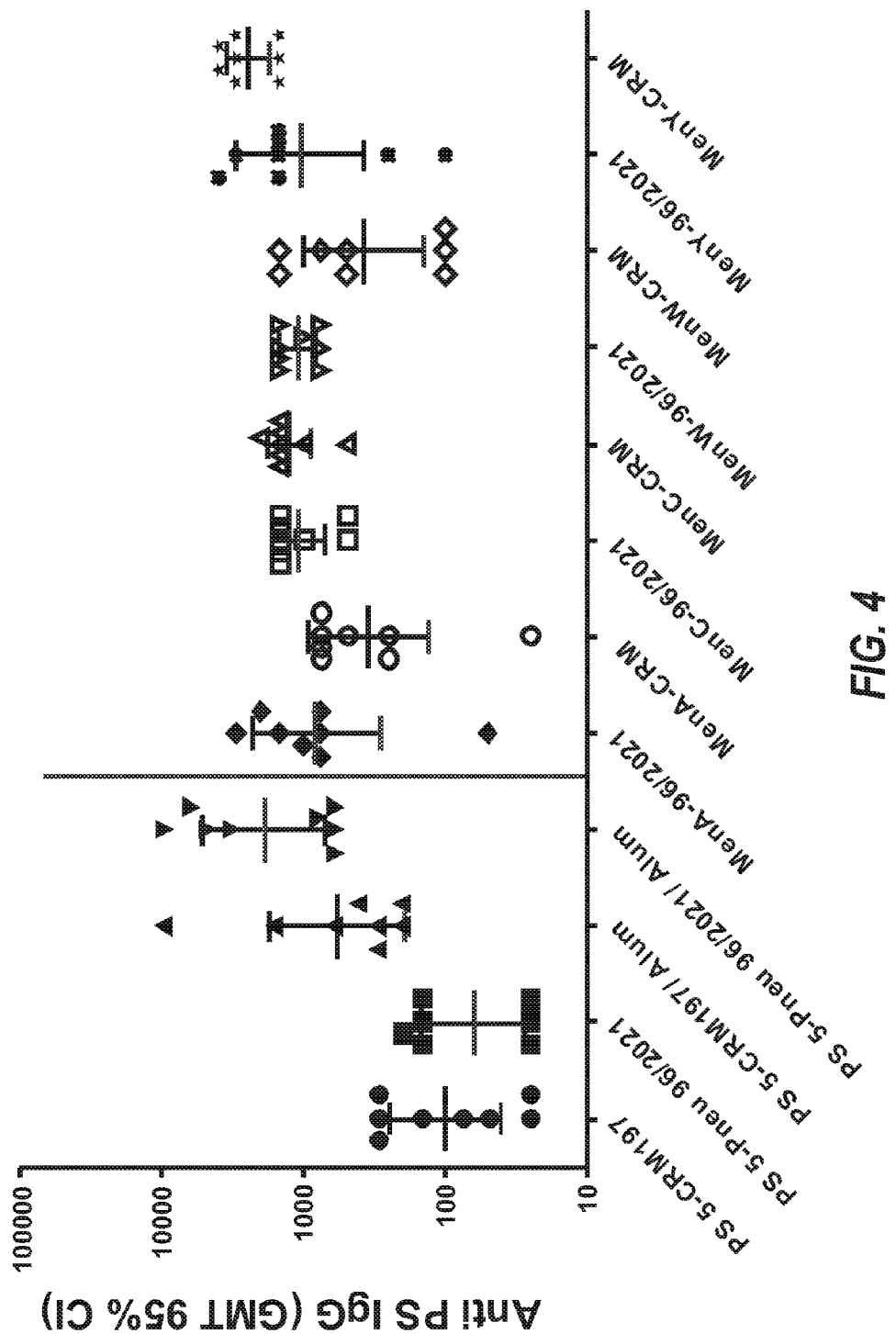
FIG. 4 compares the immunogenicity of various pneumococcal and meningococcal saccharide conjugates of the invention with reference CRM197 conjugates.
Figure 5:
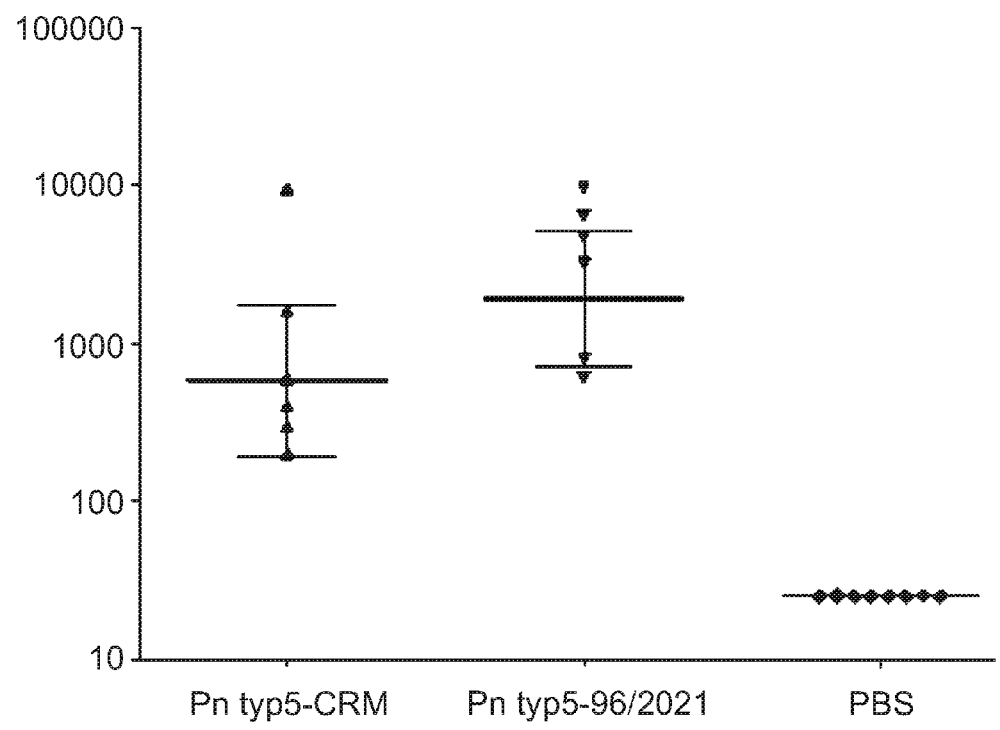
FIG. 5 compares the immunogenicity of a pneumococcal conjugate of the invention with a reference CRM197 conjugate.

Results are shown in FIG. 4, with the vertical horizontal line denoting separate studies. In the first study, the pneumo type 5-96/2021 conjugate was shown to be immunogenic. The conjugate was more immunogenic than a reference conjugate based on CRM197 in the presence of alum (a similar result with alum was seen in the related immunogenicity study reported in FIG. 5). In the second study, the MenA-, C-, W- and Y-96/2021 were shown to be immunogenic, with immunogenicity comparable to or better than that of the reference conjugates.

D. Pneumo Type 5-96/2021 Conjugates Provide Protective Immunity

The pneumo type 5-96/2021 conjugate was compared to a reference pneumo type 5-CRM197 conjugate in a mouse model of protective immunity against pneumococcus serotype 5 infection. In this experiment, groups of ten mice were immunized intraperitoneally with the different immunogens (with or without alum as adjuvant) at days 0, 14 and 28. Two groups of mice immunized with PBS alone and PBS/alum, respectively, were used as negative controls. Two weeks after the last immunization, all groups were infected intraperitoneally with a lethal dose of a pneumococcal type 5 strain (STREP-5). The protective efficacy was assessed using measures of bacteremia reduction and mortality. 24 hours post infection, the level of bacteremia was evaluated in each of the immunized groups and compared with that of the control groups. Mortality was followed for 10 days post infection.

Figure 6A:
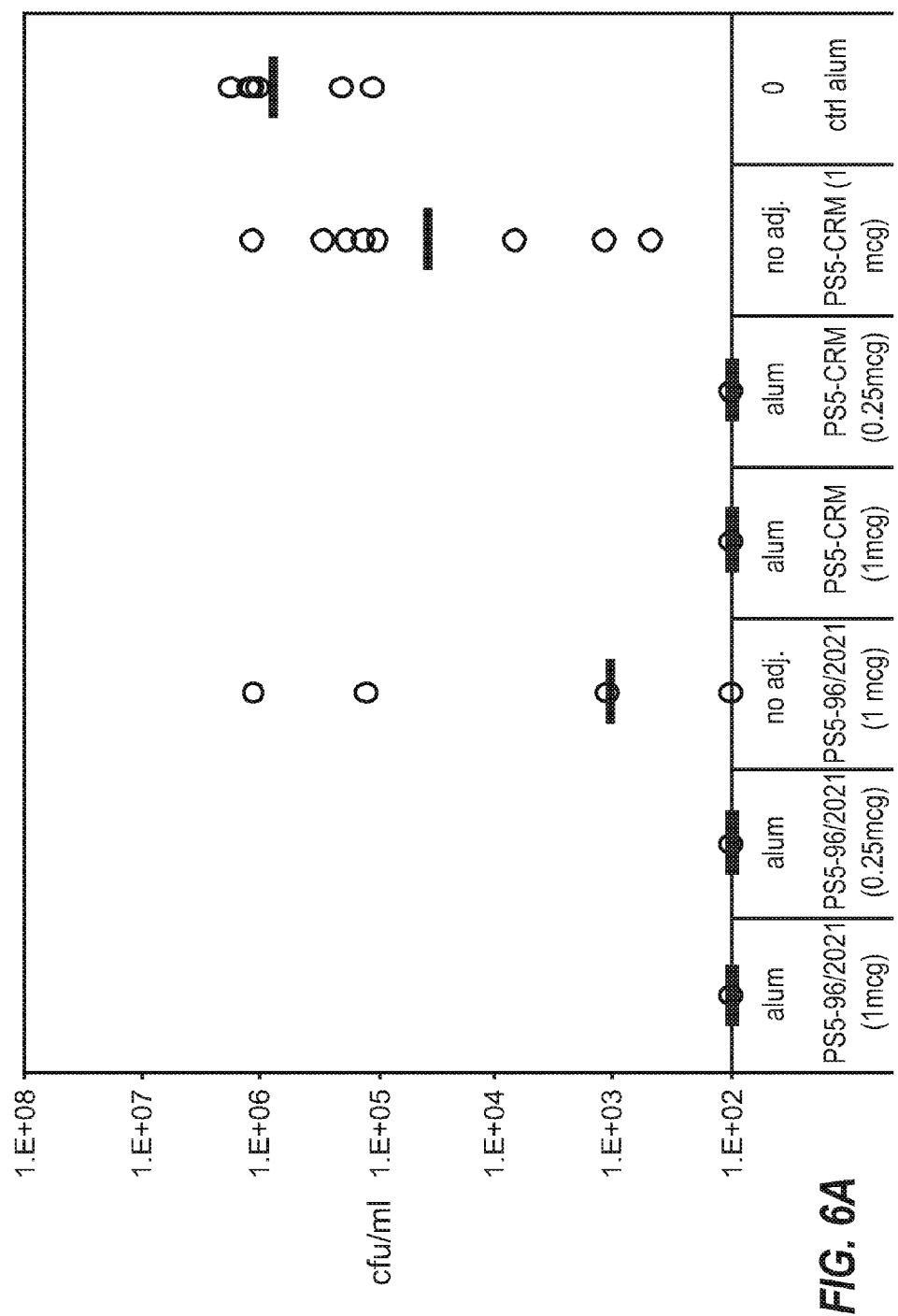
FIG. 6A compares the effects of a pneumococcal conjugate of the invention with a reference CRM197 conjugate in a model of protective immunity against pneumococcus serotype 5 infection.

Results are reported in FIG. 6A and FIG. 6B. Both conjugates conferred complete protection at doses of 1 µg and 0.25 µg in the presence of alum adjuvant. However, only the pneumo type 5-96/2021 conjugate was capable of conferring protection against mortality in the absence of adjuvant.

Figure 7A:
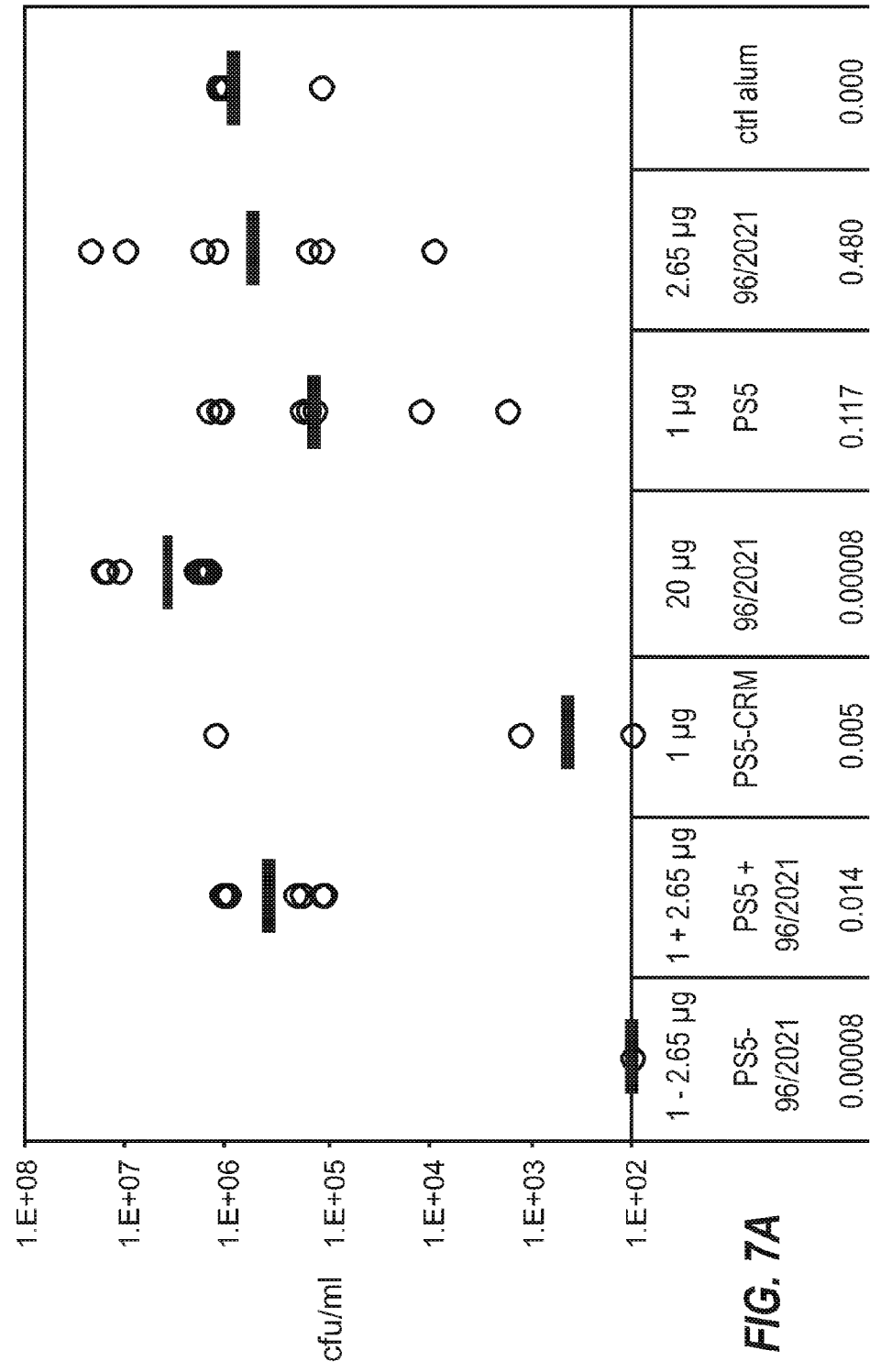
FIG. 7A compares the effects of a pneumococcal conjugate of the invention, a reference CRM197 conjugate, and the pneumococcal saccharide and carrier alone and together, in a model of protective immunity against pneumococcus serotype 5 infection.

In a related study, these conjugates were compared with the saccharide or 96/2021 carrier protein alone and together. Both conjugates gave complete (pneumo type 5-96/2021 conjugate) or almost complete (pneumo type 5-CRM197) protection. In contrast, the saccharide and carrier (alone or together) were ineffective (FIG. 7A and 7B).

E. Immunogenicity of MenA-96/2021 Conjugates

Post second immunization sera were pooled from mice administered with: a) MenA oligosaccharide conjugated to CRM197 or to 96/2021; b) a combination of MenA-, C-, W- and Y-96/2021 conjugates, with or without alum. These pools were tested by ELISA for anti serogroup A antibodies titer. Functionality of the antibodies elicited against the capsular polysaccharide was assessed in a serum bactericidal assay using rabbit complement (rSBA).

Figure 8:
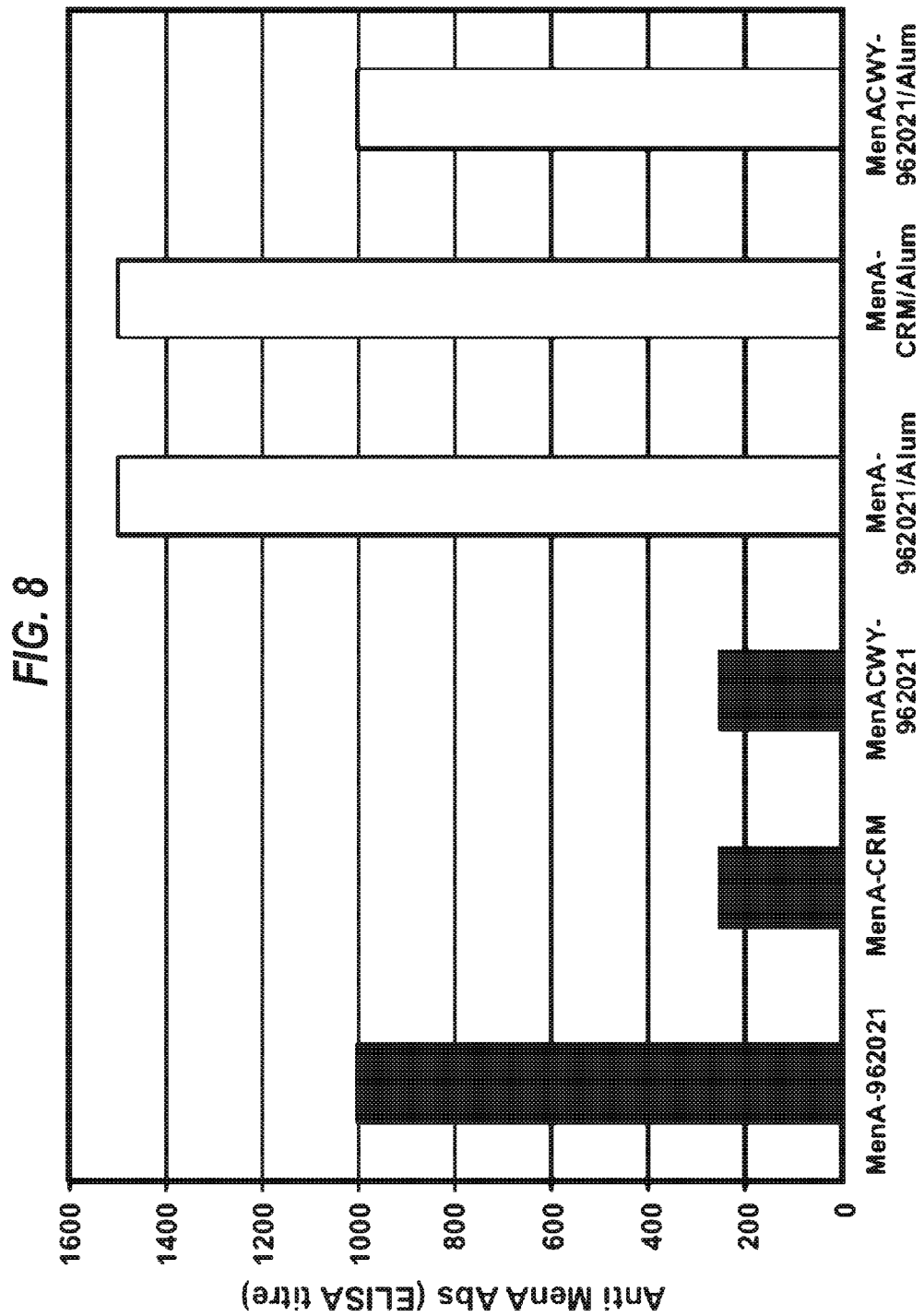
FIG. 8 compares the immunogenicity of a meningococcal serogroup A conjugate of the invention with a reference CRM197 conjugate, alone and in combination with other meningococcal conjugates.
Figure 9:
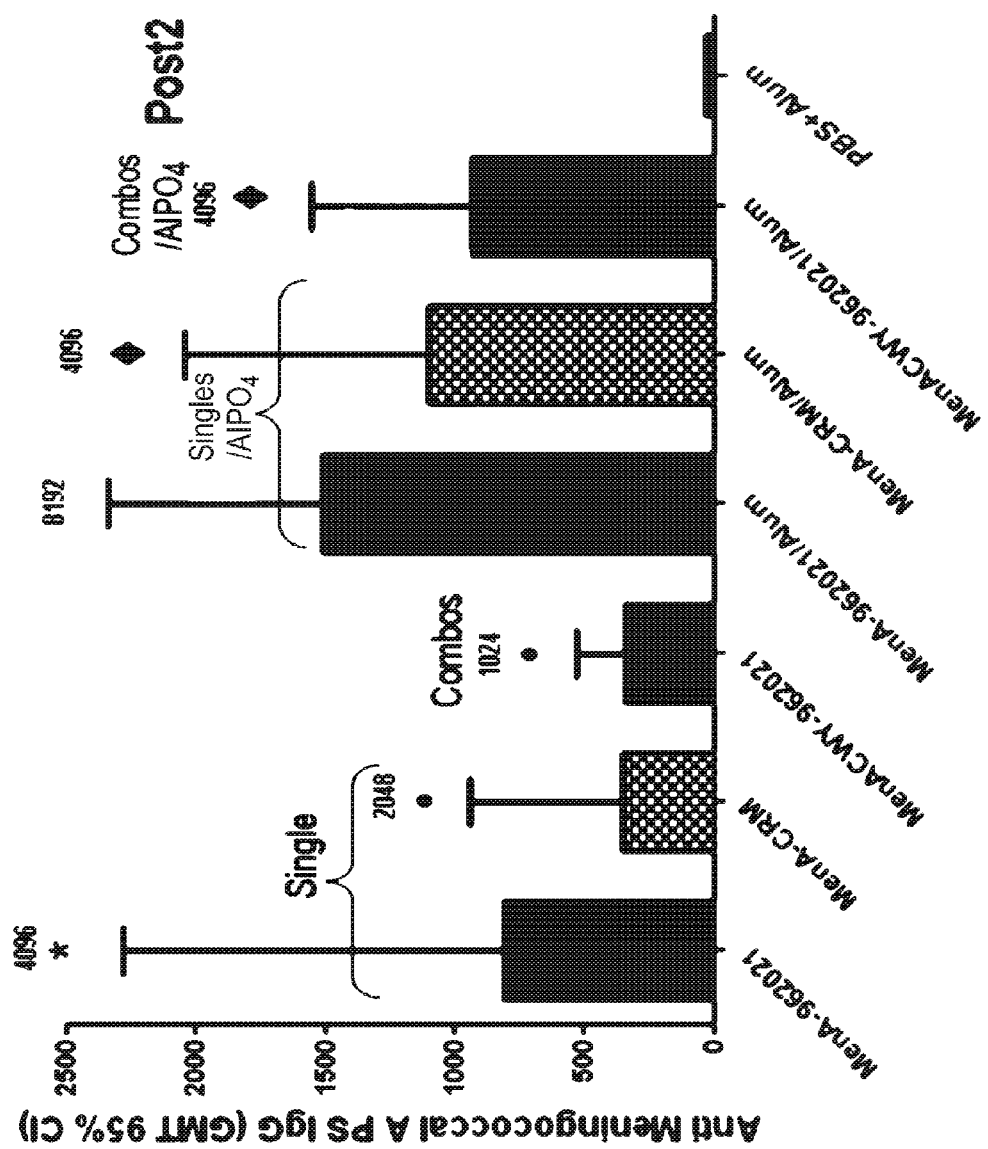
FIG. 9 compares the immunogenicity of a meningococcal serogroup A conjugate of the invention with a reference CRM197 coiugate, alone and in combination with other meningococcal conjugates, SBA titers are given above each bar.

FIG. 8 shows the results for the pooled sera. The MenA-96/2021 conjugates were more immunogenic than the MenA-CRM197 conjugates. The MenA-96/2021 conjugates remained immunogenic when combined with corresponding MenC, MenW135 and MenY conjugates. Similar observations were made when the post second immunization sera from individual mice were tested (FIG. 9, SBA titres above bars).

Figure 10:
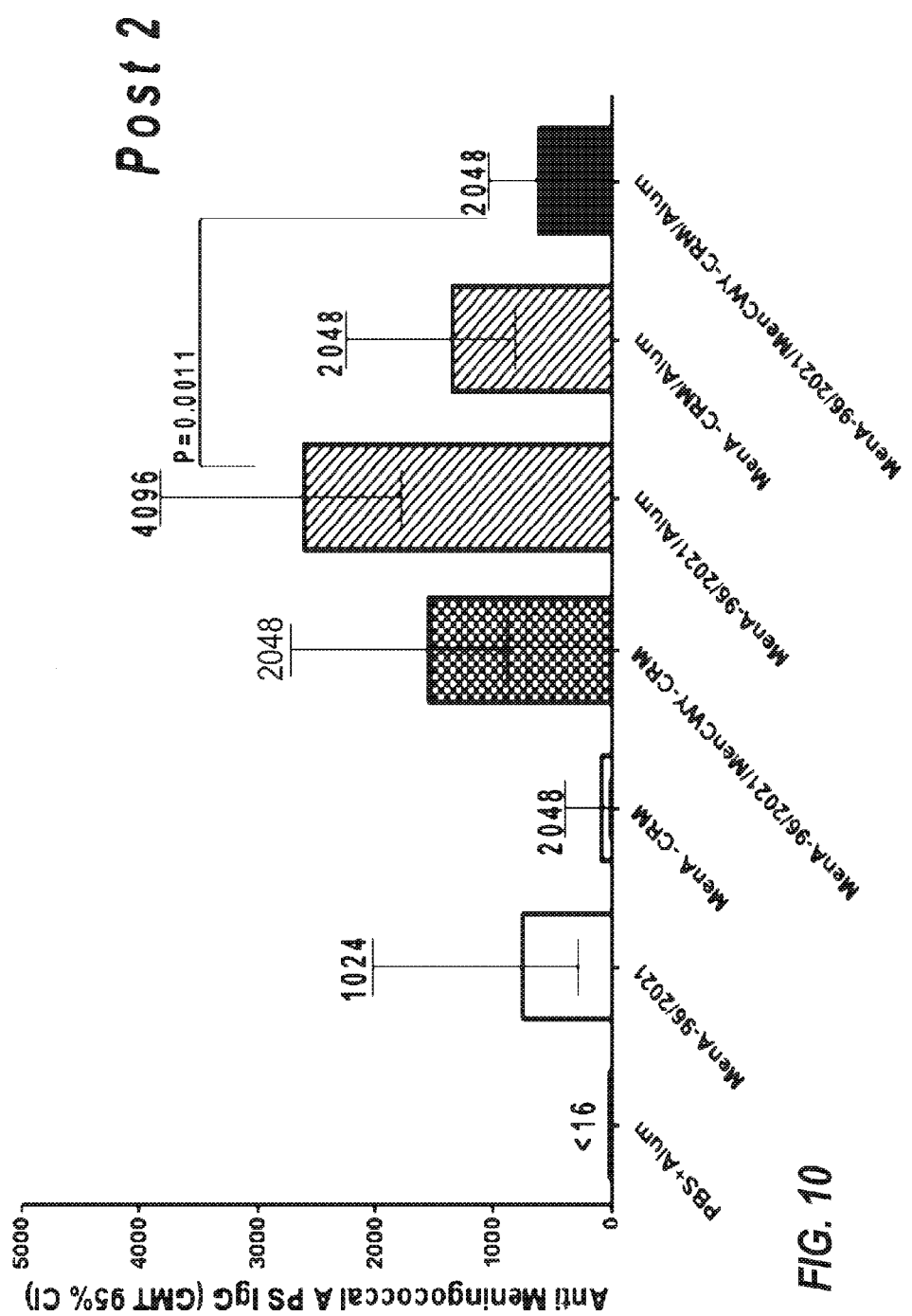
FIG. 10 compares the immunogenicity of a meningococcal sero group A conjugate of the invention with a reference CRM197 conjugate, alone and in combination with other meningococcal conjugates. SBA titers are given above each bar.

In another study, post second immunization sera from individual mice administered with: a) MenA oligosaccharide conjugated to CRM197 or to 96/2021; b) combinations of the MenA-96/2021 conjugates with MenC-, W- and Y-CRM197 conjugates, with or without alum. These pools were tested by ELISA for anti serogroup A antibodies titer. Once again, the MenA-96/2021 conjugates were more immunogenic than the MenA-CRM197 conjugates (FIG. 10, SBA titres above bars). The MenA-96/2021 conjugates remained immunogenic when they were combined with MenC-, W— and Y—CRM197 conjugates.

F. Immunogenicity of MenC-96/2021 Conjugates

Post second immunization sera were pooled from mice administered with: a) MenC oligosaccharide conjugated to CRM197 or to 96/2021; b) a combination of MenA-, C-, W- and Y-96/2021 conjugates, with or without alum. These pools were tested by ELISA for anti serogroup C antibodies titer. Functionality of the antibodies elicited against the capsular polysaccharide was assessed in a serum bactericidal assay using rabbit complement (rSBA).

Figure 11:
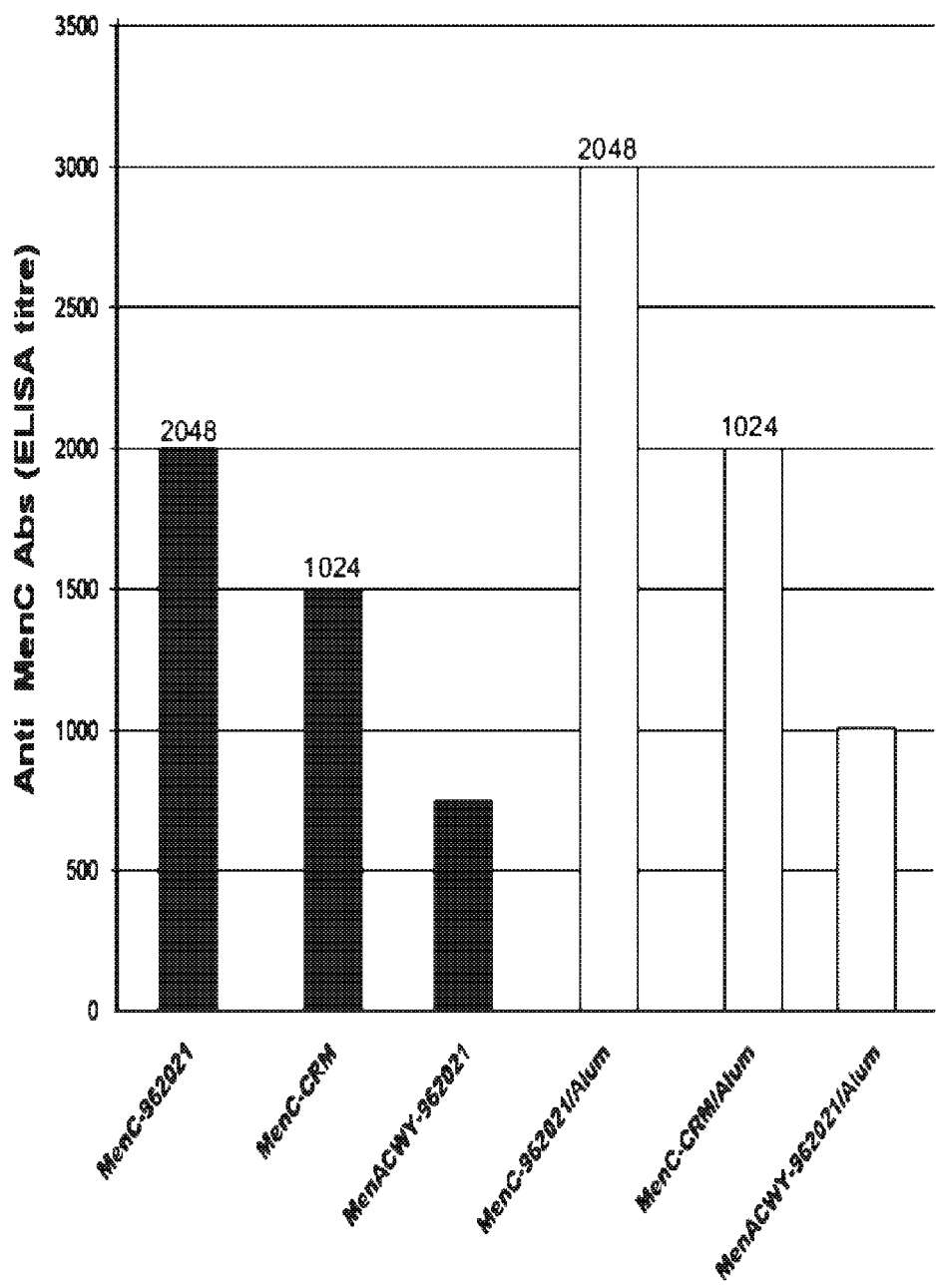
FIG. 11 compares the immunogenicity of a meningococcal serogroup C conjugate of the invention with a reference CRM197 conjugate, alone and in combination with other meningococcal conjugates.

FIG. 11 shows the results for the pooled sera, with SBA titres above the bars. The immunogenicity of the MenC-96/2021 conjugates seemed to be higher or comparable to that of the MenC-CRM197 conjugates. The MenC-96/2021 conjugates remained immunogenic when combined with corresponding MenC, MenW135 and MenY conjugates.

G. Immunogenicity of MenW-96/2021 Conjugates

Post second immunization sera were pooled from mice administered with: a) MenW oligosaccharide conjugated to CRM197 or to 96/2021; b) a combination of MenA-, C-, W- and Y-96/2021 conjugates, with or without alum. These pools were tested by ELISA for anti serogroup W antibodies titer.

Figure 12:
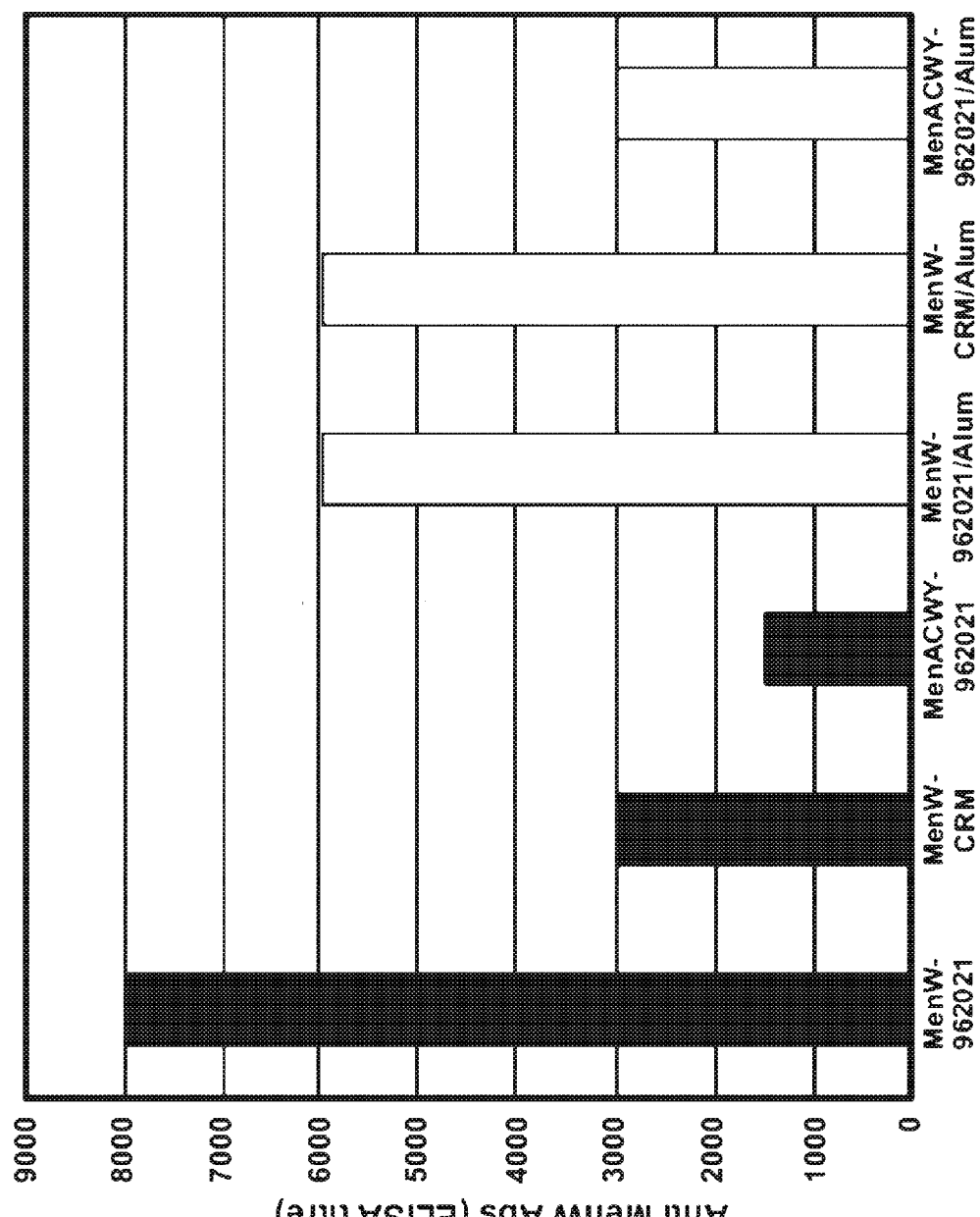
FIG. 12 compares the immunogenicity of a meningococcal serogroup W135 conjugate of the invention with a reference CRM197 conjugate, alone and in combination with other meningococcal conjugates.

FIG. 12 shows the results for the pooled sera. The immunogenicity of the MenW-96/2021 conjugates seems to be higher (without alum) or comparable (with alum) to that of the MenW-CRM197 conjugates. The MenW-96/2021 conjugates remained immunogenic when combined with corresponding MenC, MenW135 and MenY conjugates.

H. Immunogenicity of MenY-96/2021 Conjugates

Post second immunization sera were pooled from mice administered with: a) MenY oligosaccharide conjugated to CRM197 or to 96/2021; b) a combination of MenA-, C-, W- and Y-96/2021 conjugates, with or without alum. These pools were tested by ELISA for anti serogroup Y antibodies titer.

Figure 13:
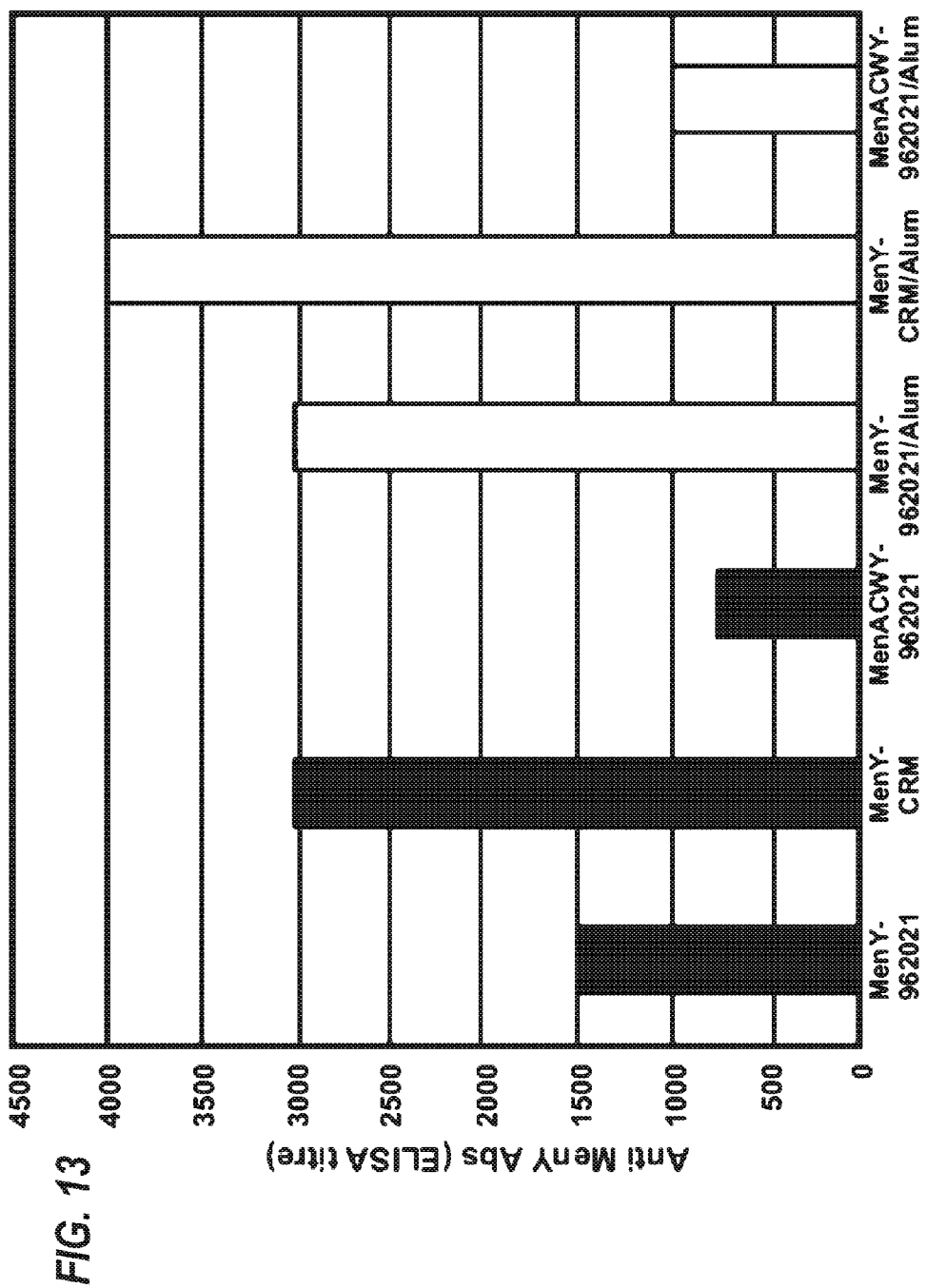
FIG. 13 compares the immunogenicity of a meningococcal serogroup Y conjugate of the invention with a reference CRM197 conjugate, alone and in combination with other meningococcal conjugates.

As shown in FIG. 13, the immunogenicity of the MenY-96/2021 conjugates seems to be comparable to that of the MenY-CRM197 conjugates, and remains immunogenic when combined with corresponding MenC, MenW135 and MenY conjugates.

I. T-Cell Response to MenC-96/2021 Conjugates

The T-cell response to MenC oligosaccharide conjugated to CRM197, 96/2021 or spr1416 was compared. In this experiment, groups of eight CD1 mice were immunized subcutaneously with the different immunogens (1 µg saccharide dose without alum) at days 0, 14 and 28. Two groups of mice immunized with PBS alone and the unconjugated MenC oligosaccharide (1 µg saccharide dose), respectively, were used as negative controls. 21 days after the last immunization, serum from each mouse was tested for anti-polysaccharide antibodies by ELISA. Spleens were isolated from three mice in each group for analysis of T-cell cytokine profile by intracellular-staining multicolour FACS after in vitro antigen-specific restimulation.

Figure 14:
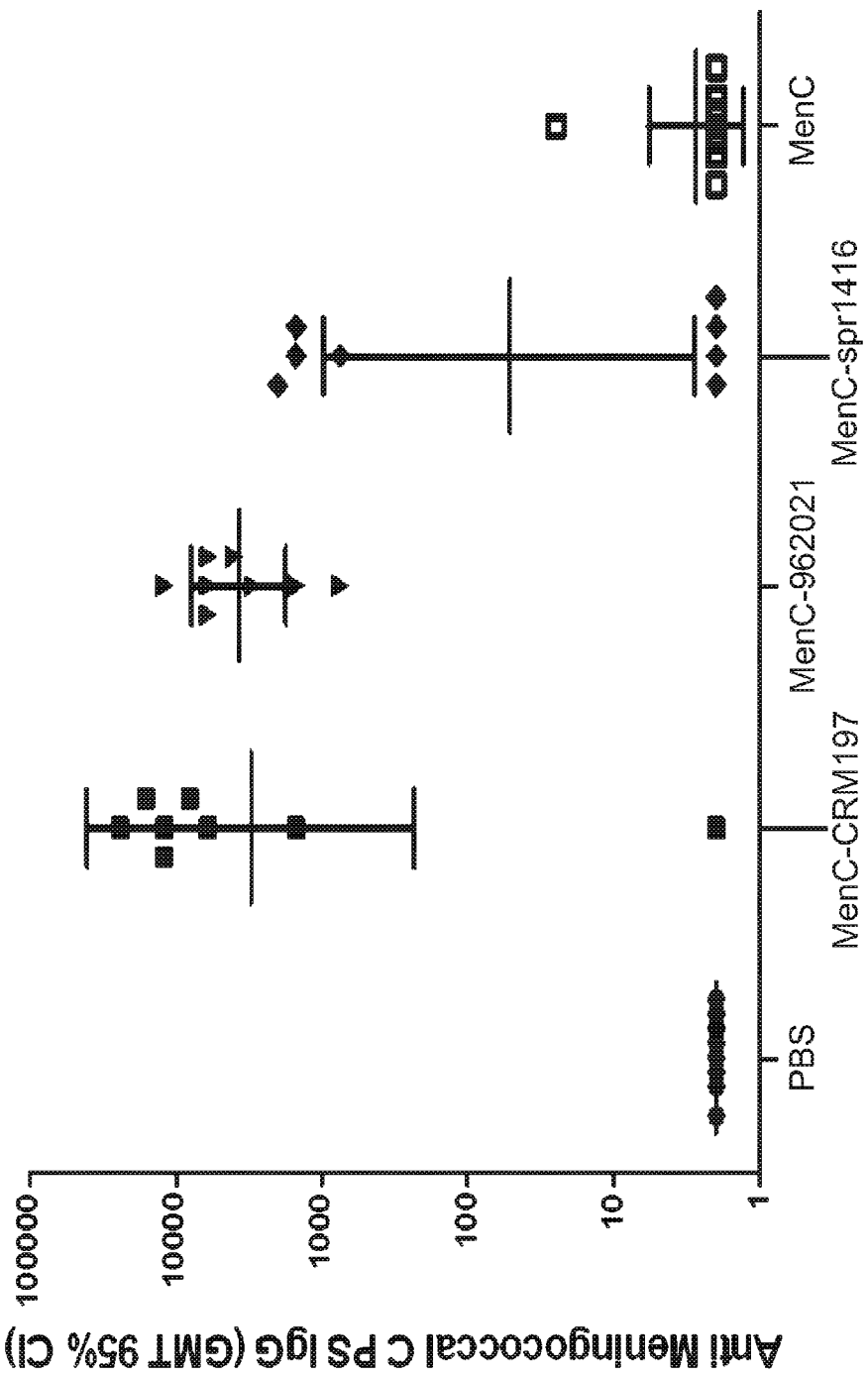
FIG. 14 compares the immunogenicity of a meningococcal serogroup C conjugate of the invention with a reference CRM197 conjugate and a spr1416 conjugate.
Figure 15:
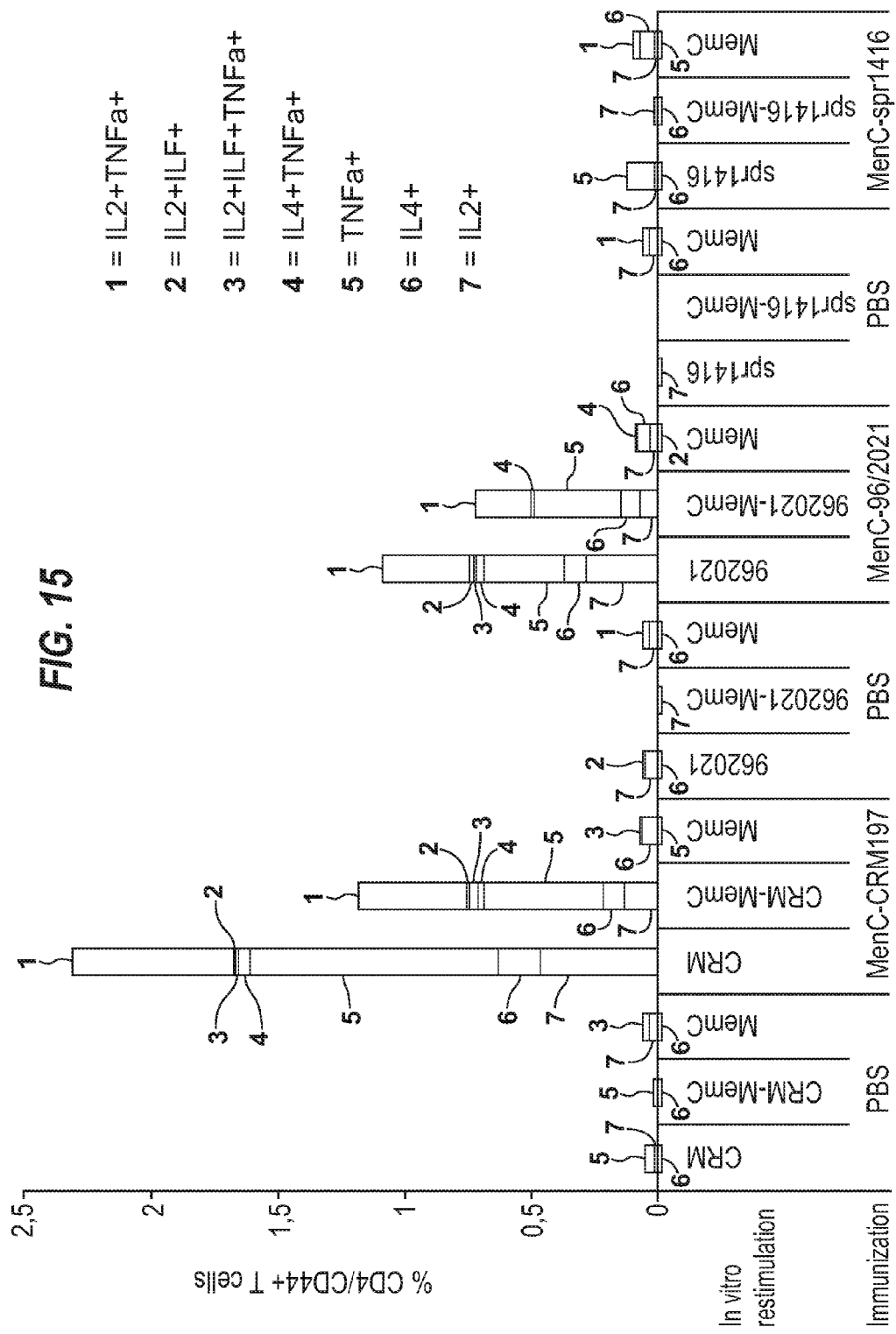
FIG. 15 compares the T-cell response to a meningococcal serogroup C conjugate of the invention with a reference CRM197 conjugate and a spr1416 conjugate.

ELISA results are reported in FIG. 14. The immunogenicity of the MenC-96/2021 conjugates seemed to be higher or comparable to that of the MenC-CRM197 and MenC-spr1416 conjugates. CRM197 and 96/2021, but not spr1416, induced T cell responses (FIG. 15).

J. Preparation of 96/2021 Incorporating HAG

A nucleic acid encoding the 96/2021 hybrid of SEQ ID NO: 9 (in vector pET21+ or pET24+ (Merck)) was transformed into competent cells of the methionine auxotrophic E. coli strains B834(DE3) (Merck) and T7 express crystal (NEB) using standard procedures.

To produce proteins incorporating HAG, the cells were inoculated into defined media so that the precise concentration of methionine could be controlled. Either AB4 complex or M9 minimal medium which did not contain methionine was used as the base media, supplemented with antibiotics as appropriate for maintenance of the host and/or expression plasmid. The composition of each medium is as follows:

AB4 without Methionine:

AB4base 2×: Alanine 1 g/L, Arginine 0.858 g/L, Asparagine 0.65 g/L, Asparatic acid 0.656 g/L, Cysteine 0.202 g/L, Glutamine 0.806 g/L, Glutamic acid 0.812 g/L, Glycine 1.036 g/L, Histidine 0.26 g/L, Isoleucine 0.594 g/L, Leucine 1.176 g/L, Lysine 0.806 g/L, Phenylalanine 0.554 g/L, Proline 0.476 g/L, Serine 4.108 g/L, Threonine 0.622 g/L, Tryptophan 0.222 g/L, Tyrosine 0.5 g/L, Valine 0.83 g/L, Adenine 1 g/L, Guanosine 0.858 g/L, Thymine 0.65 g/L, Uracil 0.656 g/L, Water 1000 ml.

Vit Mix 1000×: Riboflavin 1 g/L, Niacinaminde 1 g/L, Piridoxinchloride 1 g/L, Thiamine 1 g/L, Water 1000 ml.

Trace Elements 2000×: $FeSO_4 \cdot 7H_2O$ 5.6 g/L, $MnCl_4 \cdot 4H_2O$ 4.0 g/L, $CoCl_2 \cdot 6H_2O$ 5.6 g/L, $CaCl_2 \cdot 2H_2O$ 3.0 g/L, $CuSO_4$ 0.4 g/L, $ZnSO_4 \cdot 7H_2O$ 0.6 g/L, Water 1000 ml.

Glucose (25%): Glucose 250 g/L, Water 1000 ml.

Final AB4 media (1×): AB4base 2.0×500 ml, Water 386.5 ml, PBS 20×100 ml, Vit Mix 1 ml, Trace Elements 0.5 ml, Glucose (25%) 12 ml.

M9:

Solution I: Glucose 200 g/L, $MgSO_4 \cdot 7H_2O$ 4.9 g/L, $CaCl_2 \cdot 2H_2O$ 0.28 g/L, Water 1000 ml.

Solution II (pH 7.4): $K_2HPO_4$ 70 g/L, $KH_2PO_4$ 30 g/L, NaCl 5 g/L, $(NH_4)_2SO_4$ 6 g/L, Water 1000 ml.

To make the final media, solutions I/II were mixed in the ratio 85:5:10 ($H_2O$:Solution I:Solution II).

The B834(DE3) or T7 express crystal strain carrying a 96/2021 expression vector was inoculated into either AB4 or M9 base media supplemented with methionine to 0.176 g/L. Cells were grown at 25° C. with shaking at 180 rpm until an OD600 of 1.6 was reached, as measured by a DU530 spectrophotometer (Beckman). At this point the cells were pelleted by centrifugation at 10,000 g for 30 minutes at 4° C. and washed twice in fresh base medium without any methionine, in order to remove methionine from the cell pellet. Following this, the pellet was resuspended and inoculated into a fresh culture of base medium, this time supplemented with HAG to the same concentration as the methionine was present in the initial growth stage (no methionine was added to this medium). The culture was supplemented with IPTG to 1 mM in order to induce expression of the 96/2021 hybrid protein and incubated for a further 3-6 hours at 25° C. with shaking at 180 rpm.

Figure 16:
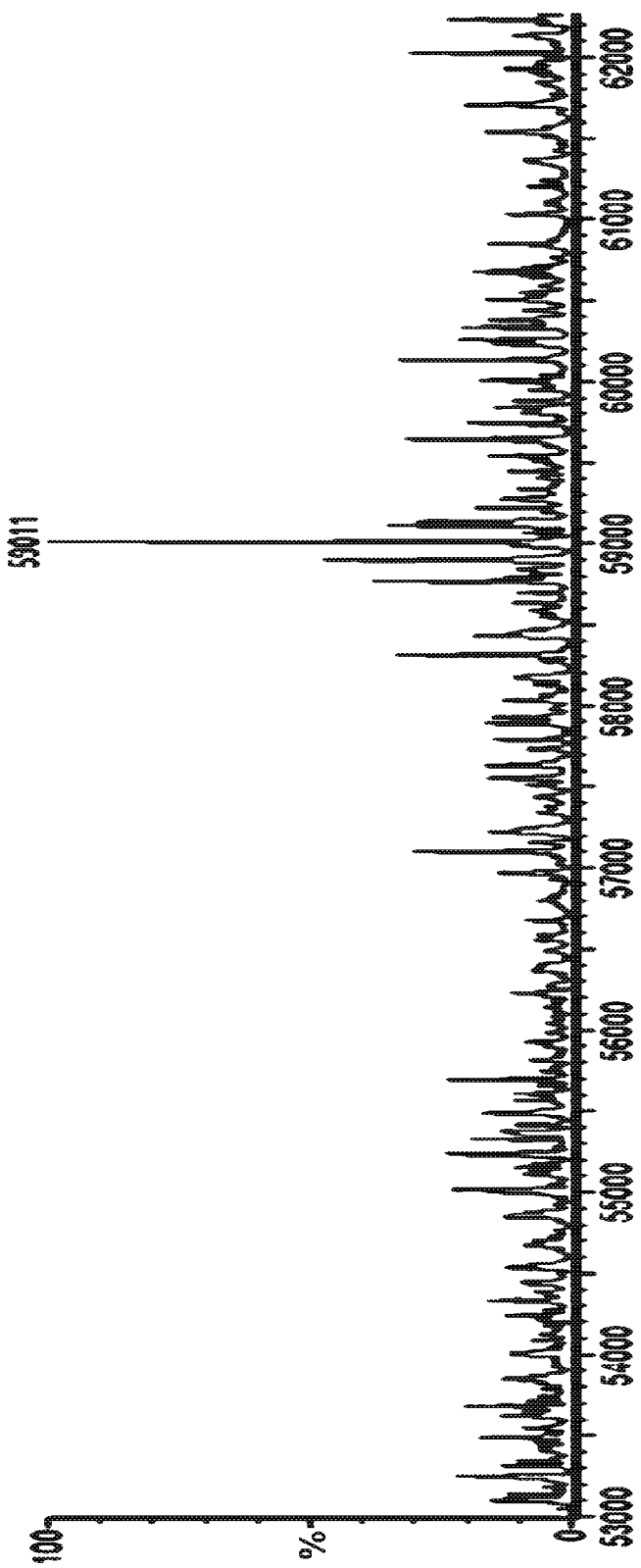
FIG. 16 shows the mass spectrometry trace of a carrier of the invention which has been expressed in a host cell such that l-homoallylglycine residues have been incorporated into the protein at the positions normally comprising methionine (SEQ ID NO: 20 vs. SEQ ID NO: 9).

The resulting cells were lysed and the protein purified using an IMAC column, with any residual imadazole removed by dialysis. The mass of the purified protein was then measured by mass spectrometry (see FIG. 16), and confirmed to have a mass approximately corresponding to the predicted weight of the protein of SEQ ID NO: 20 (i.e. SEQ ID NO: 9 in which each methionine has been substituted from L-homoallylglycine). This indicated that expression of the protein in the presence of HAG and the absence of methionine caused HAG to be substituted in place of methionine during expression of 96/2021.

Immunisation Study (1)

General Assay Protocol:

Balb/c mice were immunized by subcutaneous injection according to the schedule described below. The injection volume was 200 µl and the injection contained alum phosphate adjuvant.

| Group | Mice per group | Immunogen | Antigen dose |
|---|---|---|---|
| 1 | 1-8 | PBS | 1 µg |
| 2 | 9-16 | MenA-CRM197 | 1 µg |
| 3 | 17-24 | MenA-CRM197 (high glycosylation) | 1 µg |
| 4 | 25-32 | MenA-96/2021 | 1 µg |
| 5 | 33-40 | MenA-CRM197 + MenCWY | 2 µg + 1, 1, 1, 1 µg |
| 6 | 41-48 | MenA-CRM197 (high glycosylation) + MenCWY | 2 µg + 1, 1, 1, 1 µg |
| 7 | 49-56 | MenA-96/2021 + MenCWY | 2 µg + 1, 1, 1, 1 µg |

MenCWY = combination of MenC-, W- and Y-CRM197 prepared according to ref. 320.

The conjugates had the following properties:

| Sample | Saccharide (µg/mL) | Protein (µg/mL) | Sacc/Protein (w/w) | Sacc/Protein (mol/mol) | Free Sacc % | Endotoxin (EU/µg) |
|---|---|---|---|---|---|---|
| MenA-CRM197 | 1901.6 | 4523.7 | 0.42 | 5.5 | — | — |
| MenA-CRM197 (high glycosylation) | 538.0 | 711.3 | 0.76 | 9.8 | <16.1 | 0.03 |
| MenA-96/2021 | 110.4 | 405.0 | 0.27 | 3.7 | 10 | 0.81 |

Figure 17:
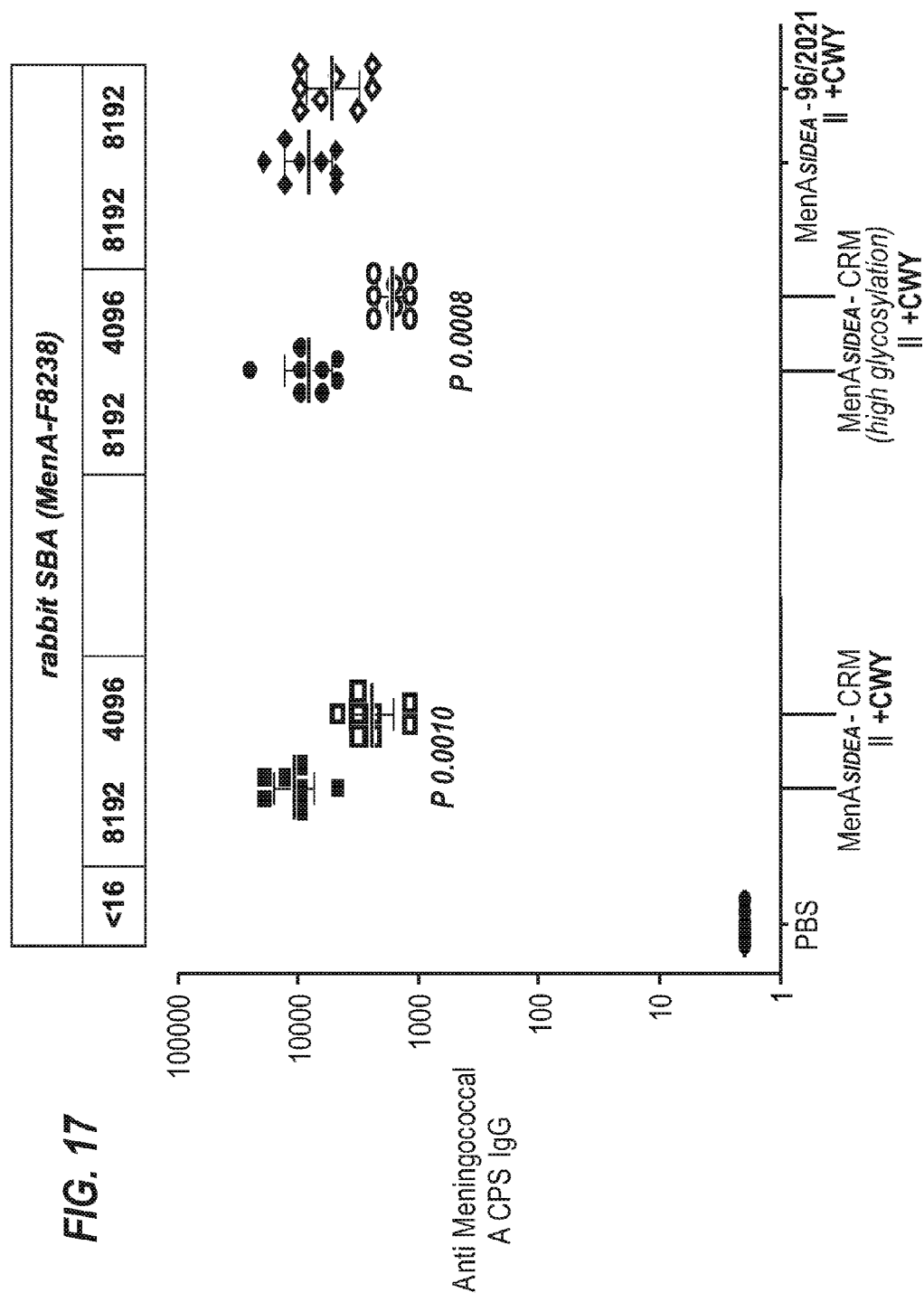
FIG. 17 compares the immunogenicity of a meningococcal serogroup A conjugate of the invention with reference CRM197 conjugates, alone and in combination with other meningococcal conjugates.

The post third immunisation IgG antibody titre against serogroup A capsular polysaccharide and serum bactericidal antibody titre against serogroup A strain F8238 are shown in FIG. 17. The serogroup A conjugates were immunogenic and induced bactericidal antibodies. Responses were slightly reduced when either of the CRM197 conjugates were combined with other CRM197 conjugates derived from serogroups C, W135 and Y, but still well above the control. In contrast, little or no reduction was seen when the MenA-96/2021 conjugate was combined with these conjugates. Accordingly, the use of 96/2021 as carrier may help to reduce any immune interference between the serogroup A conjugate and these conjugates.

Figure 18A:
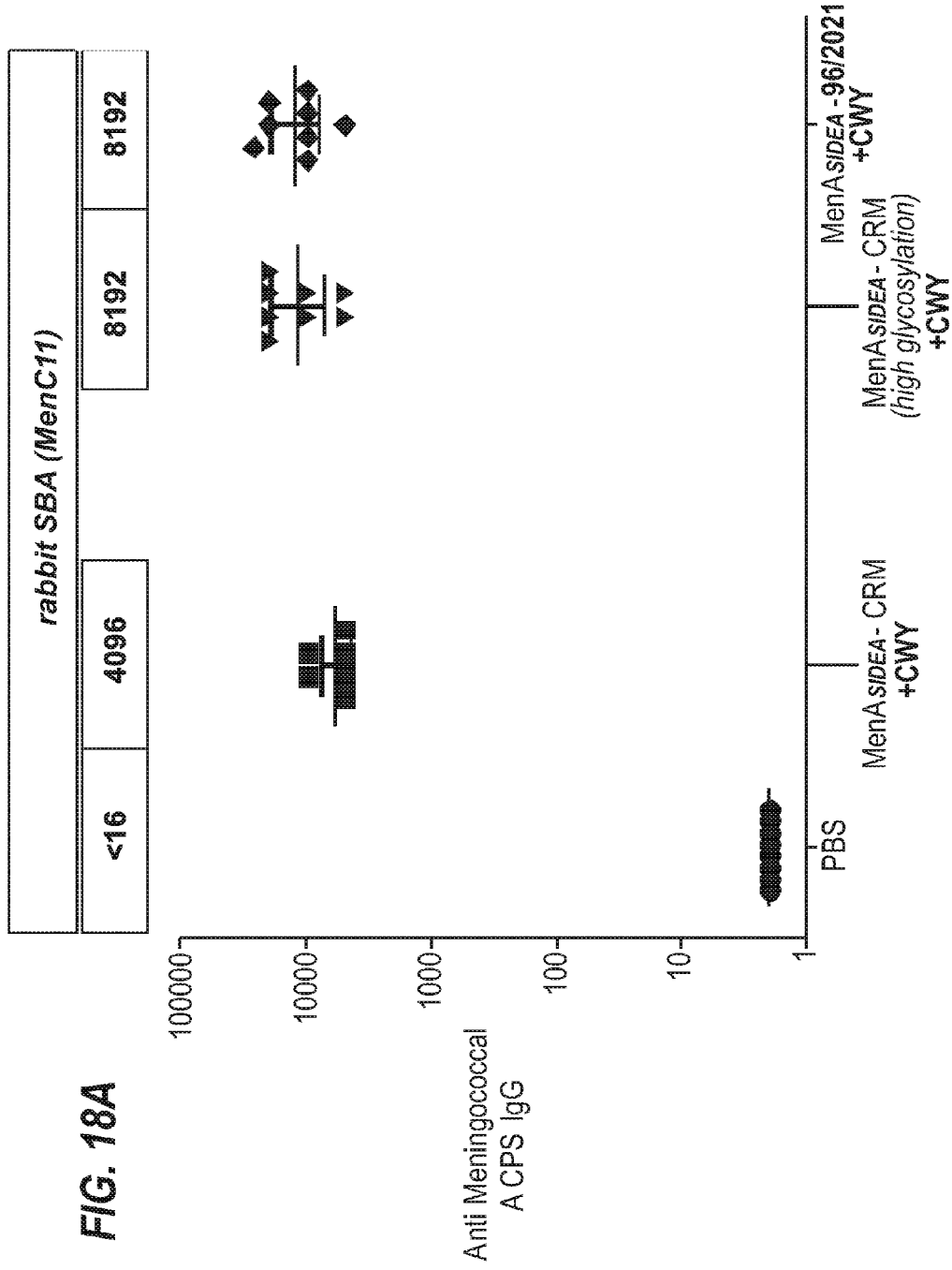
FIG. 18A compares the immunogenicity of the other meningococcal conjugates in the study of FIG. 17.
Figure 18B:
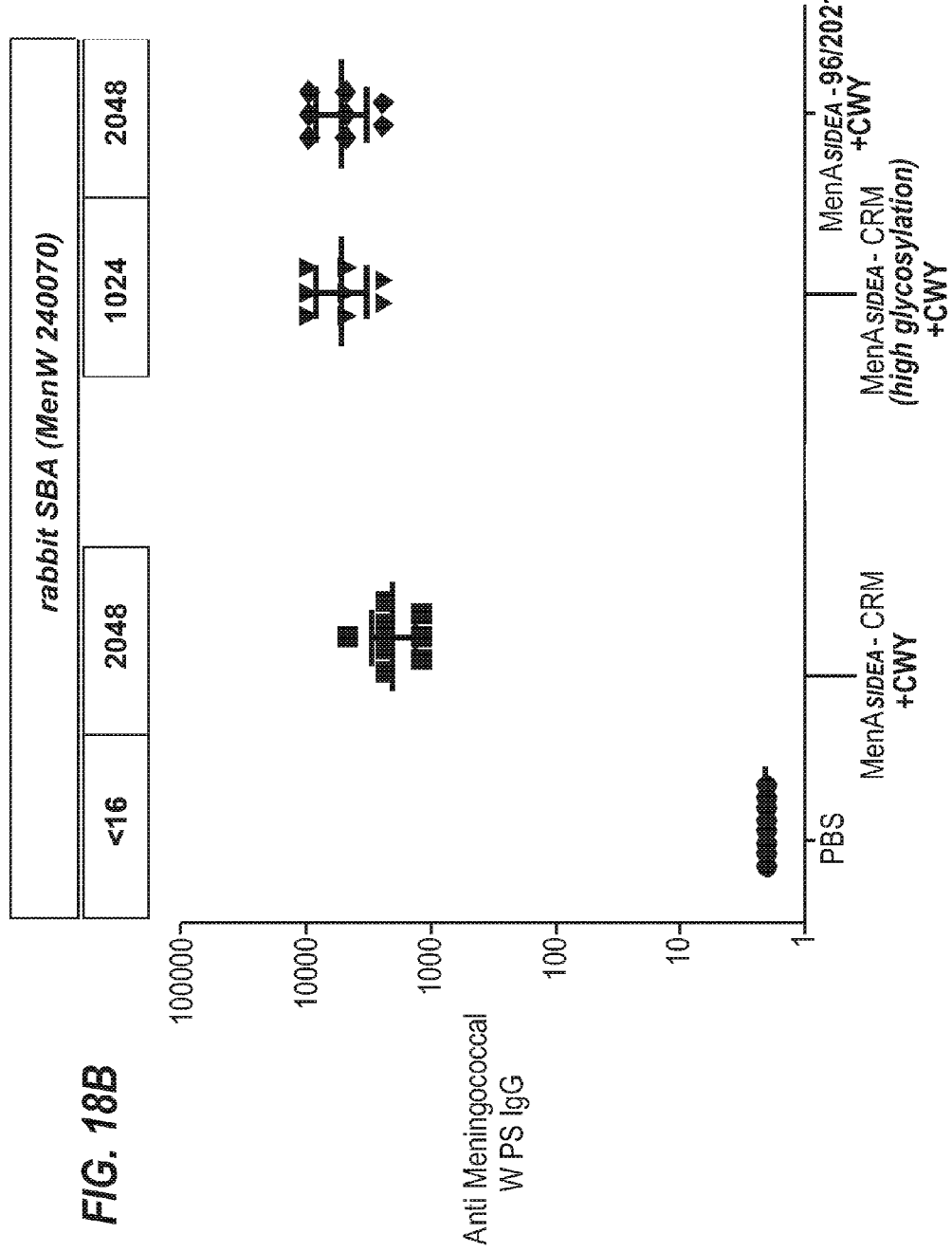
FIG. 18B compares the immunogenicity of the other meningococcal conjugates in the study of FIG. 17.

The post third immunisation IgG antibody titre against serogroups C, W135 and Y capsular polysaccharide and serum bactericidal antibody titre against certain strains from these serogroups are shown in FIG. 18A, FIG. 18B, and FIG. 18C. The use of 96/2021 as carrier for serogroup A did not affect the immune responses to these other polysaccharides.

It will be understood that the invention has been described by way of example only and modifications may be made whilst remaining within the scope and spirit of the invention.

REFERENCES

[1] Lindberg (1999) *Vaccine* 17 Suppl 2:S28-36
[2] Buttery & Moxon (2000) *J R Coll Physicians Lond* 34:163-8
[3] Ahmad & Chapnick (1999) *Infect Dis Clin North Am* 13:113-33, vii
[4] Goldblatt (1998) *J. Med. Microbiol.* 47:563-567
[5] EP-B-0 477 508
[6] U.S. Pat. No. 5,306,492
[7] WO98/42721
[8] Dick et al. in *Conjugate Vaccines* (eds. Cruse et al.) Karger, Basel, 1989, Vol. 10, 48-114
[9] Hermanson Bioconjugate Techniques, Academic Press, San Diego Calif. (1996)
[10] Ramsay et al. (2001) *Lancet* 357(9251):195-6
[11] Prieler et al. (2006) 47th Annual ICAAC (abstract)
[12] Rennels et al. (2004) Pediatr Infect Dis J. 23(5):429-35
[13] Snape et al. (2008) JAMA 299(2):173-84
[14] Dagan et al. (2010) Vaccine. 28(34):5513-23. Epub 2010 Jun. 25
[15] WO00/56360
[16] Hoskins et al. (2001) J. Bacteriol. 183:5709-5717.
[17] Falugi et al. (2001) *Eur J Immunol.* 31(12):3816-24.
[18] Geysen et al. (1984) *PNAS USA* 81:3998-4002.
[19] Carter (1994) *Methods Mol Biol* 36:207-23.
[20] Jameson, B A et al. 1988, *CABIOS* 4(1):181-186.
[21] Raddrizzani & Hammer (2000) *Brief Bioinform* 1(2): 179-89.
[22] De Lalla et al. (1999) *J. Immunol.* 163:1725-29.
[23] Brusic et al. (1998) *Bioinformatics* 14(2):121-30
[24] Meister et al. (1995) *Vaccine* 13(6):581-91.
[25] Roberts et al. (1996) *AIDS Res Hum Retroviruses* 12(7):593-610.
[26] Maksyutov & Zagrebelnaya (1993) *Comput Appl Biosci* 9(3):291-7.
[27] Feller & de la Cruz (1991) *Nature* 349(6311):720-1.
[28] Hopp (1993) *Peptide Research* 6:183-190.
[29] Welling et al. (1985) *FEBS Lett.* 188:215-218.
[30] Davenport et al. (1995) *Immunogenetics* 42:392-297.
[31] WO2004/092209.
[32] WO2008/061953.
[33] *Research Disclosure,* 453077 (January 2002)
[34] WO2005/000346
[35] EP-A-0372501.
[36] EP-A-0378881.
[37] EP-A-0427347.
[38] WO93/17712
[39] WO94/03208.
[40] WO98/58668.
[41] EP-A-0471177.
[42] WO91/01146
[43] Falugi et al. (2001) *Eur J Immunol* 31:3816-3824.
[44] Baraldo et al. (2004) *Infect Immun* 72(8):4884-7.
[45] EP-A-0594610.
[46] Ruan et al. (1990) *J Immunol* 145:3379-3384.
[47] WO00/56360.
[48] Kuo et al. (1995) *Infect Immun* 63:2706-13.
[49] Michon et al. (1998) *Vaccine.* 16:1732-41.
[50] WO02/091998.
[51] WO01/72337
[52] WO00/61761.
[53] WO00/33882
[54] U.S. Pat. No. 6,699,474
[55] Ravenscroft et al. (1999) *Vaccine* 17:2802-2816.
[56] Costantino et al. (1999) *Vaccine* 17:1251-1263.
[57] WO02/058737.
[58] Frash (1990) p. 123-145 of *Advances in Biotechnological Processes* vol. 13 (eds. Mizrahi & Van Wezel)
[59] WO03/007985.
[60] Inzana (1987) *Infect. Immun.* 55:1573-1579.
[61] WO200/5103230
[62] Kandil et al. (1997) *Glycoconj J*14:13-17.
[63] Berkin et al. (2002) *Chemistry* 8:4424-4433.
[64] Glode et al. (1979) *J Infect Dis* 139:52-56
[65] WO94/05325; U.S. Pat. No. 5,425,946.
[66] WO2005/033148.
[67] WO03/080678.
[68] WO2008/084411
[69] Nilsson & Svensson (1979) *Carbohydrate Research* 69: 292-296)
[70] Tokunaka et al. (1999) *Carbohydr Res* 316:161-172.
[71] WO03/097091
[72] Pang et al. (2005) *Biosci Biotechnol Biochem* 69:553-8.
[73] Read et al. (1996) *Carbohydr Res.* 281:187-201.
[74] Takeo and Tei (1986) *Carbohydr Res.* 145:293-306
[75] Tanaka et al. (2003) *Tetrahedron Letters* 44:3053-3057
[76] Ning et al. (2002) *Tetrahedron Letters* 43:5545-5549
[77] Geurtsen et al. (1999) *Journal of Organic Chemistry* 64 (21):7828-7835
[78] Wu et al. (2003) *Carbohydr Res.* 338:2203-12
[79] Nicolaou et al. (1997) *J. Am. Chem. Soc.* 119:449-450
[80] Yamada et al. (1999) *Tetrahedron Letters* 40:4581-4584
[81] Yamago et al. (2001) *Org. Lett.* 24:3867-3870
[82] Yuguo et al. (2004) *Tetrahedron* 60: 6345-6351
[83] Amaya et al. (2001) *Tetrahedron Letters* 42:9191-9194
[84] Mei et al. (2005) *Carbohydr Res.* 340:2345-2351
[85] Takeo et al. (1993) *Carbohydr Res.* 245:81-96
[86] Jamois et al. (2005) *Glycobiology* 15(4):393-407
[87] Lefeber et al. (2001) *Chem. Eur. J.* 7(20):4411-4421
[88] Huang et al. (2005) *Carbohydr Res.* 340:603-608
[89] U.S. Pat. No. 5,508,191.
[90] MiKyoung et al. (2003) *Biochemical Engineering Journal,* 16:163-8.
[91] Barsanti et al. (2001) *J Appl Phycol* 13:59-65.
[92] Bardotti et al. (2008) Vaccine 26:2284-96
[93] Jones (2005) *An. Acad. Bras. Cienc,* 77(2) 293-324.
[94] Jones (2005) *J Pharm Biomed Anal* 38 840-850.
[95] WO2006/050341
[96] Guttormsen et al. (2008) *Proc Natl Acad Sci USA.* 105(15):5903-8. Epub 2008 Mar. 31.
[97] WO96/40795
[98] Michon et al. (2006) Clin Vaccine Immunol. 2006 August; 13(8):936-43.
[99] Lewis et al. (2004) *PNAS USA* 101:11123-8.
[100] Wessels et al. (1989) *Infect Immun* 57:1089-94.
[101] WO2006/082527.
[102] WO2009/081276.
[103] Moreau et al. (1990) *Carbohydrate Res.* 339(5):285-91
[104] Fournier et al. (1984) *Infect. Immun.* 45(1):87-93.
[105] Jones (2005) *Carbohydrate Res.* 340(6):1097-106.

[106] Fattom et al. (1998) *Infect Immun.* 66(10):4588-92
[107] Lernercinier and Jones (1996) *Carbohydrate Res.* 296:83-96.
[108] Jones and Lernercinier (2002) *J Pharm Biomed Anal.* 30(4): 1233-47.
[109] WO05/033148
[110] WO 00/56357
[111] Hestrin (1949) *J. Biol. Chem.* 180:249-261.
[112] Konadu et al. (1994) *Infect. Immun.* 62:5048-5054.
[113] Fattom et al. (1990) *Infect Immun.* 58(7):2367-74
[114] Gilbert et al. (1994) *J. Microb. Meth.* 20:39-46.
[115] Kreis et al. (1995) *Int J Biol Macromol.* 17(3-4):117-30.
[116] Höög et al. (2002) *Carbohydr Res.* 337(21-23):2023-36
[117] www.polymer.de
[118] Lees et al. (1996) *Vaccine* 14:190-198.
[119] WO95/08348.
[120] U.S. Pat. No. 4,761,283
[121] U.S. Pat. No. 4,356,170
[122] U.S. Pat. No. 4,882,317
[123] U.S. Pat. No. 4,695,624
[124] *Mol. Immunol.*, 1985, 22, 907-919
[125] EP-A-0208375
[126] Bethell G. S. et al., *J. Biol. Chem.*, 1979, 254, 2572-4
[127] Hearn M. T. W., *J. Chromatogr.*, 1981, 218, 509-18
[128] WO00/10599
[129] Gever et al., Med. Microbiol. Immunol, 165: 171-288 (1979).
[130] U.S. Pat. No. 4,057,685.
[131] U.S. Pat. Nos. 4,673,574; 4,761,283; 4,808,700.
[132] U.S. Pat. No. 4,459,286.
[133] U.S. Pat. No. 5,204,098
[134] U.S. Pat. No. 4,965,338
[135] U.S. Pat. No. 4,663,160.
[136] WO2007/000343.
[137] WO96/40242
[138] Lei et al. (2000) *Dev Biol* (*Basel*) 103:259-264
[139] WO00/38711
[140] Wang et al. (2009) *Chem. Biol.* 16:323-336
[141] Floyd et al. (2009) *Angew. Chem.* 48:7798-7802
[142] *Research Disclosure*, 453077 (January 2002)
[143] EP-A-0372501.
[144] EP-A-0378881.
[145] EP-A-0427347.
[146] WO93/17712
[147] WO94/03208.
[148] WO98/58668.
[149] EP-A-0471177.
[150] WO91/01146
[151] Baraldo et al. (2004) *Infect Immun* 72(8):4884-7.
[152] EP-A-0594610.
[153] Ruan et al. (1990) *J Immunol* 145:3379-3384.
[154] WO00/56360.
[155] WO02/091998.
[156] Kuo et al. (1995) *Infect Immun* 63:2706-13.
[157] Michon et al. (1998) *Vaccine.* 16:1732-41.
[158] WO01/72337
[159] WO00/61761.
[160] WO2004/041157.
[161] WO02/34771.
[162] WO99/42130.
[163] WO2004/011027.
[164] WO99/24578.
[165] WO99/36544.
[166] WO99/57280.
[167] WO00/22430.
[168] Tettelin et al. (2000) *Science* 287:1809-1815.
[169] Pizza et al. (2000) *Science* 287:1816-1820.
[170] WO01/52885.
[171] Bjune et al. (1991) *Lancet* 338(8775):1093-1096.
[172] Fukasawa et al. (1999) *Vaccine* 17:2951-2958.
[173] Rosenqvist et al. (1998) *Dev. Biol. Stand.* 92:323-333.
[174] Watson (2000) *Pediatr Infect Dis J* 19:331-332.
[175] Rubin (2000) *Pediatr Clin North Am* 47:269-285, v.
[176] Jedrzejas (2001) *Microbiol Mol Biol Rev* 65:187-207.
[177] Bell (2000) *Pediatr Infect Dis J* 19:1187-1188.
[178] Iwarson (1995) *APMIS* 103:321-326.
[179] Gerlich et al. (1990) *Vaccine* 8 Suppl:S63-68 & 79-80.
[180] Hsu et al. (1999) *Clin Liver Dis* 3:901-915.
[181] Gustafsson et al. (1996) *N. Engl. J. Med.* 334:349-355.
[182] Rappuoli et al. (1991) *TIBTECH* 9:232-238.
[183] Vaccines (2004) eds. Plotkin & Orenstein. ISBN 0-7216-9688-0.
[184] WO02/02606.
[185] Kalman et al. (1999) *Nature Genetics* 21:385-389.
[186] Read et al. (2000) *Nucleic Acids Res* 28:1397-406.
[187] Shirai et al. (2000) *J. Infect. Dis.* 181(Suppl 3):S524-S527.
[188] WO99/27105.
[189] WO00/27994.
[190] WO00/37494.
[191] WO99/28475.
[192] Ross et al. (2001) *Vaccine* 19:4135-4142.
[193] Sutter et al. (2000) *Pediatr Clin North Am* 47:287-308.
[194] Zimmerman & Spann (1999) *Am Fam Physician* 59:113-118, 125-126.
[195] Dreesen (1997) *Vaccine* 15 Suppl:S2-6.
[196] MMWR Morb Mortal Wkly Rep 1998 Jan. 16; 47(1): 12, 19.
[197] McMichael (2000) *Vaccine* 19 Suppl 1:S101-107.
[198] WO02/34771.
[199] Dale (1999) *Infect Dis Clin North Am* 13:227-43, viii.
[200] Ferretti et al. (2001) *PNAS USA* 98: 4658-4663.
[201] WO03/093306.
[202] WO2004/018646.
[203] WO2004/041157.
[204] Ichiman and Yoshida (1981) *J. Appl. Bacteriol.* 51:229.
[205] U.S. Pat. No. 4,197,290
[206] Ichiman et al. (1991) *J. Appl. Bacteriol.* 71:176.
[207] Robinson & Torres (1997) *Seminars in Immunology* 9:271-283.
[208] Donnelly et al. (1997) *Annu Rev Immunol* 15:617-648.
[209] Scott-Taylor & Dalgleish (2000) *Expert Opin Investig Drugs* 9:471-480.
[210] Apostolopoulos & Plebanski (2000) *Curr Opin Mol Ther* 2:441-447.
[211] Ilan (1999) *Curr Opin Mol Ther* 1:116-120.
[212] Dubensky et al. (2000) *Mol Med* 6:723-732.
[213] Robinson & Pertmer (2000) *Adv Virus Res* 55:1-74.
[214] Donnelly et al. (2000) *Am J Respir Crit. Care Med* 162(4 Pt 2):S190-193.
[215] Davis (1999) *Mt. Sinai J. Med.* 66:84-90.
[216] Gennaro (2000) *Remington: The Science and Practice of Pharmacy.* 20th edition, ISBN: 0683306472.
[217] Almeida & Alpar (1996) *J. Drug Targeting* 3:455-467.
[218] U.S. Pat. No. 6,355,271.
[219] WO00/23105.
[220] U.S. Pat. No. 5,057,540.
[221] WO96/33739.
[222] EP-A-0109942.
[223] WO96/11711.
[224] WO00/07621.

[225] Barr et al. (1998) *Advanced Drug Delivery Reviews* 32:247-271.
[226] Sjolanderet et al. (1998) *Advanced Drug Delivery Reviews* 32:321-338.
[227] Pizza et al. (2000) *Int J Med Microbiol* 290:455-461.
[228] WO95/17211.
[229] WO98/42375.
[230] Singh et all (2001) *J Cont Release* 70:267-276.
[231] WO99/27960.
[232] U.S. Pat. No. 6,090,406
[233] U.S. Pat. No. 5,916,588
[234] EP-A-0626169.
[235] Dyakonova et al. (2004) Int Immunopharmacol 4(13): 1615-23.
[236] FR-2859633.
[237] Signorelli & Hadden (2003) *Int Immunopharmacol* 3(8): 1177-86.
[238] WO2004/064715.
[239] De Libero et al, *Nature Reviews Immunology*, 2005, 5: 485-496
[240] U.S. Pat. No. 5,936,076.
[241] Oki et al, *J. Clin. Investig.*, 113: 1631-1640
[242] US2005/0192248
[243] Yang et al, *Angew. Chem. Int. Ed.*, 2004, 43: 3818-3822
[244] WO2005/102049
[245] Goff et al, *J. Am. Chem., Soc.*, 2004, 126: 13602-13603
[246] WO03/105769
[247] Cooper (1995) *Pharm Biotechnol* 6:559-80.
[248] Kandimalla et al. (2003) *Nucleic Acids Research* 31:2393-2400.
[249] WO02/26757.
[250] WO99/62923.
[251] Krieg (2003) *Nature Medicine* 9:831-835.
[252] McCluskie et al. (2002) *FEMS Immunology and Medical Microbiology* 32:179-185.
[253] WO98/40100.
[254] U.S. Pat. No. 6,207,646.
[255] U.S. Pat. No. 6,239,116.
[256] U.S. Pat. No. 6,429,199.
[257] Kandimalla et al. (2003) *Biochemical Society Transactions* 31 (part 3):654-658.
[258] Blackwell et al. (2003) *J Immunol* 170:4061-4068.
[259] Krieg (2002) *Trends Immunol* 23:64-65.
[260] WO01/95935.
[261] Kandimalla et al. (2003) *BBRC* 306:948-953.
[262] Bhagat et al. (2003) *BBRC* 300:853-861.
[263] WO03/035836.
[264] WO01/22972.
[265] Schellack et al. (2006) *Vaccine* 24:5461-72.
[266] Myers et al. (1990) pages 145-156 of *Cellular and molecular aspects of endotoxin reactions*.
[267] Ulrich (2000) Chapter 16 (pages 273-282) of reference 303.
[268] Johnson et al. (1999) *J Med Chem* 42:4640-9.
[269] Baldrick et al. (2002) *Regulatory Toxicol Pharmacol* 35:398-413.
[270] WO 94/21292.
[271] U.S. Pat. No. 4,680,338.
[272] U.S. Pat. No. 4,988,815.
[273] WO92/15582.
[274] Stanley (2002) *Clin Exp Dermatol* 27:571-577.
[275] Wu et al. (2004) *Antiviral Res.* 64(2):79-83.
[276] Vasilakos et al. (2000) *Cell Immunol.* 204(1):64-74.
[277] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[278] Jones (2003) *Curr Opin Investig Drugs* 4:214-218.
[279] WO2004/060308.
[280] WO2004/064759.
[281] U.S. Pat. No. 6,924,271.
[282] US2005/0070556.
[283] U.S. Pat. No. 5,658,731.
[284] U.S. Pat. No. 5,011,828.
[285] WO2004/87153.
[286] U.S. Pat. No. 6,605,617.
[287] WO02/18383.
[288] WO2004/018455.
[289] WO03/082272.
[290] Johnson et al. (1999) *Bioorg Med Chem Lett* 9:2273-2278.
[291] Evans et al. (2003) *Expert Rev Vaccines* 2:219-229.
[292] Andrianov et al. (1998) *Biomaterials* 19:109-115.
[293] Payne et al. (1998) *Adv Drug Delivery Review* 31:185-196.
[294] WO03/011223.
[295] Meraldi et al. (2003) *Vaccine* 21:2485-2491.
[296] Pajak et al. (2003) *Vaccine* 21:836-842.
[297] Wong et al. (2003) *J Clin Pharmacol* 43(7):735-42.
[298] US2005/0215517.
[299] WO90/14837.
[300] Podda & Del Giudice (2003) *Expert Rev Vaccines* 2:197-203.
[301] Podda (2001) *Vaccine* 19: 2673-2680.
[302] *Vaccine Design: The Subunit and Adjuvant Approach* (eds. Powell & Newman) Plenum Press 1995 (ISBN 0-306-44867-X).
[303] *Vaccine Adjuvants: Preparation Methods and Research Protocols* (Volume 42 of *Methods in Molecular Medicine* series). ISBN: 1-59259-083-7. Ed. O'Hagan.
[304] Allison & Byars (1992) *Res Immunol* 143:519-25.
[305] Hariharan et al. (1995) *Cancer Res* 55:3486-9.
[306] WO95/11700.
[307] U.S. Pat. No. 6,080,725.
[308] WO2005/097181.
[309] Wills et al. (2000) *Emerging Therapeutic Targets* 4:1-32.
[310] *Molecular Biology Techniques: An Intensive Laboratory Course*, (Ream et al., eds., 1998, Academic Press).
[311] *Methods In Enzymology* (S. Colowick and N. Kaplan, eds., Academic Press, Inc.)
[312] *Handbook of Experimental Immunology*, Vols. I-IV (D. M. Weir and C. C. Blackwell, eds, 1986, Blackwell Scientific Publications)
[313] Sambrook et al. (2001) *Molecular Cloning: A Laboratory Manual*, 3rd edition (Cold Spring Harbor Laboratory Press).
[314] *Handbook of Surface and Colloidal Chemistry* (Birdi, K. S. ed., CRC Press, 1997)
[315] Ausubel et al. (eds) (2002) *Short protocols in molecular biology*, 5th edition (Current Protocols).
[316] *PCR (Introduction to Biotechniques Series)*, 2nd ed. (Newton & Graham eds., 1997, Springer Verlag)
[317] *Current Protocols in Molecular Biology* (F. M. Ausubel et al., eds., 1987) Supplement 30
[318] Smith & Waterman (1981) *Adv. Appl. Math.* 2: 482-489.
[319] Torosantucci et al. (2005) *J Exp Med* 202:597-606.
[320] WO03/007985
[321] Bromuro et al. (2010) *Vaccine* 28(14):2615-23.

What is claimed is:

1. A conjugate comprising an antigen covalently linked to a carrier molecule, wherein the carrier molecule comprises a spr0096 antigen covalently linked to a spr2021 antigen and the antigen is a bacterial capsular saccharide.

2. The conjugate of claim 1, wherein the carrier molecule comprises the spr0096 antigen and the spr2021 antigen as a single polypeptide chain.

3. The conjugate of claim 2, wherein the spr0096 antigen comprises an amino acid sequence having 50% or more identity to SEQ ID NO: 1 or SEQ ID NO: 2.

4. The conjugate of claim 2, wherein the spr2021 antigen comprises an amino acid sequence having 50% or more identity to SEQ ID NO: 3.

5. The conjugate of claim 3, wherein the spr2021 antigen comprises an amino acid sequence having 50% or more identity to SEQ ID NO: 3.

6. The conjugate of claim 2, wherein the polypeptide chain is of the formula $NH_2$-A-$\{$-X-L-$\}_n$-B—COOH, wherein: A is an optional N-terminal amino acid sequence; B is an optional C-terminal amino acid sequence; n is an integer of 2 or more such that there is at least an $X_1$ and an $X_2$; each X is an amino acid sequence of an spr0096 antigen or an spr2021 antigen, wherein at least one X is an spr0096 antigen and at least one X is an spr2021 antigen; and L is an optional linker amino acid sequence.

7. The conjugate of claim 6, wherein n is 2.

8. The conjugate of claim 7, wherein the $X_1$ is an spr0096 antigen and the $X_2$ is an spr2021 antigen.

9. The conjugate of claim 8, wherein the spr0096 antigen comprises an amino acid sequence having 50% or more identity to SEQ ID NO: 1 or SEQ ID NO: 2, and the spr2021 antigen comprises an amino acid sequence having 50% or more identity to SEQ ID NO: 3.

10. The conjugate of claim 1, wherein the bacterial capsular saccharide is a capsular saccharide from N. meningitidis or a capsular saccharide from S. pneumoniae.

11. The conjugate of claim 1, wherein the bacterial capsular saccharide is a capsular saccharide from N. meningitidis serogroup A, C, W135 or Y.

12. A pharmaceutical composition comprising a conjugate of claim 1 in combination with a pharmaceutically acceptable carrier.

13. A pharmaceutical composition of claim 12 comprising a mixture of conjugates comprising saccharides from N. meningitidis serogroups A, C, W135 and Y.

14. The pharmaceutical composition of claim 13, wherein the conjugates comprising saccharides from N. meningitidis serogroups A, C, W135 and Y are separate conjugates for each saccharide.

15. The pharmaceutical composition of claim 14, wherein the conjugates comprising saccharides from N. meningitidis serogroups A, C, W135 and Y are based on the same carrier.

16. A pharmaceutical composition comprising a conjugate of claim 2 in combination with a pharmaceutically acceptable carrier.

17. A pharmaceutical composition of claim 16 comprising a mixture of conjugates comprising saccharides from N. meningitidis serogroups A, C, W135 and Y.

18. The pharmaceutical composition of claim 17, wherein the conjugates comprising saccharides from N. meningitidis serogroups A, C, W135 and Y are separate conjugates for each saccharide.

19. The pharmaceutical composition of claim 18, wherein the conjugates comprising saccharides from N. meningitidis serogroups A, C, W135 and Y are based on the same carrier.

20. A method for raising an immune response in a mammal, comprising administering a conjugate of claim 1 to the mammal.

21. A method for raising an immune response in a mammal, comprising administering a conjugate of claim 2 to the mammal.

22. A method for raising an immune response in a mammal, comprising administering a pharmaceutical composition of claim 16 to the mammal.

* * * * *